US011396655B2

(12) United States Patent
Marchand et al.

(10) Patent No.: US 11,396,655 B2
(45) Date of Patent: Jul. 26, 2022

(54) **COMPOUNDS FOR DETECTING AND TREATING *MYCOPLASMA HYOPNEUMONIAE***

(71) Applicant: AEROVIRUS TECHNOLOGIES INC., St-Hyacinthe (CA)

(72) Inventors: Norman J Marchand, St Hyacinthe (CA); Thomas G Caltagirone, Jacobus, PA (US); Albert Liao, Jacobus, PA (US)

(73) Assignee: AEROVIRUS TECHNOLOGIES INC.

( * ) Notice: Subject to any disclaimer, the term of this patent is extended or adjusted under 35 U.S.C. 154(b) by 116 days.

(21) Appl. No.: 16/312,207

(22) PCT Filed: Aug. 30, 2017

(86) PCT No.: PCT/CA2017/051021
§ 371 (c)(1),
(2) Date: Dec. 20, 2018

(87) PCT Pub. No.: WO2018/039793
PCT Pub. Date: Mar. 8, 2018

(65) Prior Publication Data
US 2019/0233823 A1      Aug. 1, 2019

(30) Foreign Application Priority Data

Aug. 30, 2016   (CA) .................................... 2940637

(51) Int. Cl.
| | | |
|---|---|---|
| *C12N 15/115* | (2010.01) | |
| *C07H 21/00* | (2006.01) | |
| *C12Q 1/04* | (2006.01) | |
| *A61P 31/04* | (2006.01) | |
| *A61K 31/713* | (2006.01) | |
| *C07K 16/12* | (2006.01) | |
| *C12Q 1/689* | (2018.01) | |
| *C12N 15/10* | (2006.01) | |

(52) U.S. Cl.
CPC .......... *C12N 15/115* (2013.01); *A61K 31/713* (2013.01); *A61P 31/04* (2018.01); *C07H 21/00* (2013.01); *C07K 16/1253* (2013.01); *C12N 15/1048* (2013.01); *C12Q 1/04* (2013.01); *C12Q 1/689* (2013.01); *C12N 2310/16* (2013.01); *G01N 2333/30* (2013.01)

(58) Field of Classification Search
None
See application file for complete search history.

(56) References Cited

FOREIGN PATENT DOCUMENTS

CA   PCT/CA2016/051411 A1      6/2017

OTHER PUBLICATIONS

Jarocki et al. Open Biol., 2015 vol. 5, pp. 140175, p. 1-p. 13.*
Jarocki V.M et al. Open Biol., 2015 vol. 5 pp. 140175, ISSN 2046-2441 "MHJ-0461 is a multifunctional leucine aminopeptidase on the surface of Mycoplasma hyopneumoniae".
International Search Report dated Nov. 6, 2017 for PCT/CA2017/051021.

* cited by examiner

*Primary Examiner* — Oluwatosin A Ogunbiyi
(74) *Attorney, Agent, or Firm* — Fresh IP PLC; Clifford D. Hyra; Aubrey Y. Chen

(57) ABSTRACT

The present invention relates to aptamers, polynucleotides, and nucleic acid molecules, which include a polynucleotide sequence capable of specifically binding polypeptides participating in *M. hyopneumoniae* infection. Also provided are methods of using nucleic acid molecules, polynucleotides and synthetic antibodies directed there against for detection, treating and neutralization of *M. hyopneumoniae* infection.

9 Claims, 8 Drawing Sheets

Specification includes a Sequence Listing.

| Figure 4.A. APT3-Cooc10 | Figure 4.B. APT3-Cooc2 | Figure 4.C. APT3-Cooc3 | Figure 4.D. APT3-Cooc4 | Figure 4.E. APT3-Histo1 |
|---|---|---|---|---|
| ΔG = -14.53 kcal/mol | ΔG = -11.71 kcal/mol | ΔG = -8.63 kcal/mol | ΔG = -13.99 kcal/mol | ΔG = -15.94 kcal/mol |
| Sequence (5'->3'): GCC TGT TGT GAG TAT GAC CCT AAC GGG TAT GAC TAC AGA TGC AGG GCG GCC TGT AGC CTT GCA TTG ACA AGG GCA TGC TTA TTC TTG TCT CCC | Sequence (5'->3'): GCC TGT TGT GAG CCT CCT AAC GCG AGT GGG CCC AAT CTG GAG GGG AGC GAG AGG CAA GTA TGG TTG CCG GGA GCA TGC TTA TTC TTG TCT CCC | Sequence (5'->3'): GCC TGT TGT GAG CCT CCT AAC TAG CTC GTA GAA AAA TAT AGC GTG TGC TGG GAC TGC TCG GGA TTG CGG ACA CAT GCT TAT TCT TGT CTC CC | Sequence (5'->3'): GCC TGT TGT GAG CCT CCT AAC AGT GAT GAA GGG ATC ACG GGC AAA GGA CCG TGA CAA ATC ACG GAG TGT CAT GCT TAT TCT TGT CTC CC | Sequence (5'->3'): GCC TGT TGT GAG CCT CCT AAC CGC ACG TGG GTA TTC TAA GTG CGG TAG CTC AAT GGT GAG CGA TGA GCA TCA TGC TTA TTC TTG TCT CCC |

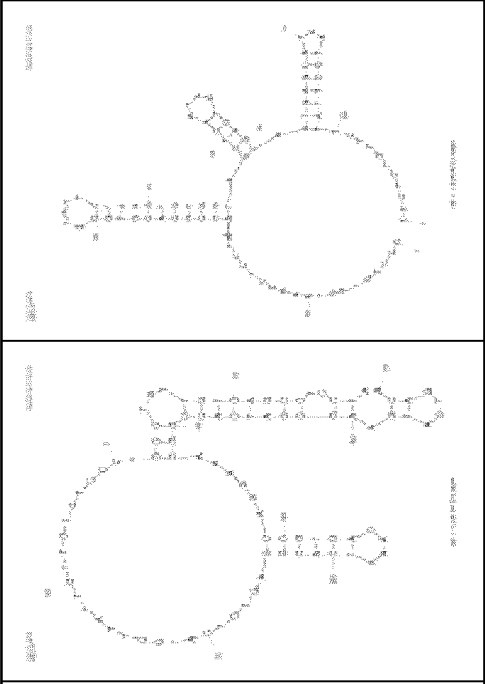

Figure 4

| Figure 4.F.<br>APT3-Histo2<br><br>$\Delta G = -14.42$ kcal/mol<br><br>Sequence (5'->3'):<br>GCC TGT GAA AGT TAC<br>CCT AAC CTG CGC GGA GAG<br>AGG CTG CGC AAG GGA GCT<br>GAG CCC AAG CGA GCT<br>TTG CTG ATG CCA TGC<br>TTA TTC TTG TCT CCC | Figure 4.G.<br>APT3-Histo4<br><br>$\Delta G = -10.01$ kcal/mol<br><br>Sequence (5'->3'):<br>GCC TGT TGT GAG CCT CAT<br>CCT AAC ATA GCA CAT<br>TTG ATG AGG AGG CCT<br>TGA TTA AAG GCC GGC<br>TTG TGA ACG TCA TGC<br>TTA TTC TTG TCT CCC | Figure 4.H.<br>APT3-Histo5<br><br>$\Delta G = -13.36$ kcal/mol<br><br>Sequence (5'->3'):<br>GCC TGT TGT GAG CCT<br>CCT AAC GAC GAT GGA<br>GCG GCC CCA AGT CGC<br>TCT TGC GAT TGA AAC ATG<br>GAT CGC ACG CAC ATC ATG<br>CTT ATT CTT GTC TCC<br>C | Figure 4.I.<br>APT3-Histo9<br><br>$\Delta G = -9.87$ kcal/mol<br><br>Sequence (5'->3'):<br>GCC TGT TGT GTT GAG CCT GCT<br>CCT AAC GTT GCG TCA<br>TAG TGG GCG GCA TCA<br>CTC GAT TGA AAC GAT<br>TAG TGT AGT ACA TGC<br>TTA TTC TTG TCT CCC | Figure 4.J.<br>APT3-Cooc7<br><br>$\Delta G = -12.48$ kcal/mol<br><br>Sequence (5'->3'):<br>GCC TGT TGT GAG CCT<br>CCT AAC ACC ACG GGC<br>CTG GGG CGC GTG TAG<br>CAT AGG CGC GTG GCA<br>ACC TAC GTA CCA TGC<br>TTA TTC TTG TCT CCC |

Figure 4 (continued)

SEQUENCE LISTING

```
<160> NUMBER OF SEQ ID NOS: 23

<210> SEQ ID NO 1
<211> LENGTH: 90
<212> TYPE: DNA
<213> ORGANISM: Artificial Sequence
<220> FEATURE:
<223> OTHER INFORMATION: Aptamer corresponding to the P97 peptide in M.
      Hyopneumoniae

<400> SEQUENCE: 1
gcctgttgtg agcctcctaa cgggtatgac tacagatgca gggcggcctg tagccttgca     60
ttgacaaggg catgcttatt cttgtctccc                                      90

<210> SEQ ID NO 2
<211> LENGTH: 89
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 2
gcctgttgtg agcctcctaa cagtgatgaa gggatcacgg gcaaaggacc gtgacaaatc     60
acggagtgtc atgcttattc ttgtctccc                                       89

<210> SEQ ID NO 3
<211> LENGTH: 90
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 3
gcctgttgtg agcctcctaa cgcgagtccc aatctggagg ggagcgagag gcaagtatgg     60
ttgccgggag catgcttatt cttgtctccc                                      90

<210> SEQ ID NO 4
<211> LENGTH: 90
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 4
gcctgttgtg agcctcctaa ccgcacgtgg gtattctaag tgcggtagct caatggtgag     60
```

```
cgatgagcat catgcttatt cttgtctccc                                       90

<210> SEQ ID NO 5
<211> LENGTH: 95
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 5
gcctgttgtg agcctcctaa ctagctcgta gaaaaaaaat atagcgtgtg ctgggactgc      60
tcgggattgc ggacacatgc ttattcttgt ctccc                                 95

<210> SEQ ID NO 6
<211> LENGTH: 90
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 6
gcctgttgtg agcctcctaa cgaaagttac aggctgcgcg gagaggagcc caagcgagct      60
ttgctgatgc catgcttatt cttgtctccc                                       90

<210> SEQ ID NO 7
<211> LENGTH: 90
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 7
gcctgttgtg agcctcctaa catagcacat tgatgagga ggccttgatt aaaggccggc       60
ttgtgaacgt catgcttatt cttgtctccc                                       90

<210> SEQ ID NO 8
<211> LENGTH: 91
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 8
gcctgttgtg agcctcctaa cgacgatgga gcggccccaa gtcgctcttg catgttaatg      60
gatcgccaca tcatgcttat tcttgtctcc c                                     91

<210> SEQ ID NO 9
<211> LENGTH: 90
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 9
gcctgttgtg agcctcctaa cgttgccgct tagtgggcgg catcactcga ttgaaacgat      60
tagtgtagta catgcttatt cttgtctccc                                       90

<210> SEQ ID NO 10
```

<211> LENGTH: 90
<212> TYPE: DNA
<213> ORGANISM: Artificial Sequence
<220> FEATURE:
<223> OTHER INFORMATION: Aptamer corresponding to P97 peptide in M.
      Hyopneumoniae

<400> SEQUENCE: 10
gcctgttgtg agcctcctaa caccacgggc ctggggcatt tatagcatag gcgcgtggca    60
acctacgtac catgcttatt cttgtctccc 90

<210> SEQ ID NO 11
<211> LENGTH: 1103
<212> TYPE: PRT
<213> ORGANISM: Mycoplasma hyopneumoniae

<400> SEQUENCE: 11

Met Ser Lys Lys Ser Lys Thr Phe Lys Ile Gly Leu Thr Ala Gly Ile
1 5 10 15

Val Gly Leu Gly Val Phe Gly Leu Thr Val Gly Leu Ser Ser Leu Ala
20 25 30

Lys Tyr Arg Ser Glu Ser Pro Arg Lys Ile Ala Asn Asp Phe Ala Ala
35 40 45

Lys Val Ser Thr Leu Ala Phe Ser Pro Tyr Ala Phe Glu Thr Asp Ser
50 55 60

Asp Tyr Lys Ile Val Lys Arg Trp Leu Val Asp Ser Asn Asn Asn Ile
65 70 75 80

Arg Asn Lys Glu Lys Val Ile Asp Ser Phe Ser Phe Phe Thr Lys Asn
85 90 95

Gly Asp Gln Leu Glu Lys Ile Asn Phe Gln Asp Pro Glu Tyr Thr Lys
100 105 110

Ala Lys Ile Thr Phe Glu Ile Leu Glu Ile Ile Pro Asp Asp Val Asn
115 120 125

Gln Asn Phe Lys Val Lys Phe Gln Ala Leu Gln Lys Leu His Asn Gly
130 135 140

Asp Ile Ala Lys Ser Asp Ile Tyr Glu Gln Thr Val Ala Phe Ala Lys
145 150 155 160

Gln Ser Asn Leu Leu Val Ala Glu Phe Asn Phe Ser Leu Lys Lys Ile
165 170 175

Thr Glu Lys Leu Asn Gln Gln Ile Glu Asn Leu Ser Thr Lys Ile Thr
180 185 190

Asn Phe Ala Asp Glu Lys Thr Ser Ser Gln Lys Asp Pro Ser Thr Leu
195 200 205

Arg Ala Ile Asp Phe Gln Tyr Asp Leu Asn Thr Ala Arg Asn Pro Glu
210 215 220

Asp Leu Asp Ile Lys Leu Ala Asn Tyr Phe Pro Val Leu Lys Asn Leu
225 230 235 240

Ile Asn Arg Leu Asn Asn Ala Pro Glu Asn Lys Leu Pro Asn Asn Leu
245 250 255

Gly Asn Ile Phe Glu Phe Ser Phe Ala Lys Asp Ser Ser Thr Asn Gln
260 265 270

Tyr Val Ser Ile Gln Asn Gln Ile Pro Ser Leu Phe Leu Lys Ala Asp
275 280 285

Leu Ser Gln Ser Ala Arg Glu Ile Leu Ala Ser Pro Asp Glu Val Gln
290 295 300

Pro Val Ile Asn Ile Leu Arg Leu Met Lys Asp Asn Ser Ser Tyr Phe

```
                305                 310                 315                 320
Leu Asn Phe Glu Asp Phe Val Asn Asn Leu Thr Leu Lys Asn Met Gln
                    325                 330                 335
Lys Glu Asp Leu Asn Ala Lys Gly Gln Asn Leu Ser Ala Tyr Glu Phe
                    340                 345                 350
Leu Ala Asp Ile Lys Ser Gly Phe Pro Gly Asp Lys Arg Ser Ser
                    355                 360                 365
His Thr Lys Ala Glu Ile Ser Asn Leu Leu Asn Lys Lys Glu Asn Ile
                    370                 375                 380
Tyr Asp Phe Gly Lys Tyr Asn Gly Lys Phe Asn Asp Arg Leu Asn Ser
385                 390                 395                 400
Pro Asn Leu Glu Tyr Ser Leu Asp Ala Ala Ser Ala Ser Leu Asp Lys
                    405                 410                 415
Lys Asp Lys Ser Ile Val Leu Ile Pro Tyr Arg Leu Glu Ile Lys Asp
                    420                 425                 430
Lys Phe Phe Ala Asp Asp Leu Tyr Pro Asp Thr Lys Asp Asn Ile Leu
                    435                 440                 445
Val Lys Glu Gly Ile Leu Lys Leu Thr Gly Phe Lys Lys Gly Ser Lys
                    450                 455                 460
Ile Asp Leu Pro Asn Ile Asn Gln Gln Ile Phe Lys Thr Glu Tyr Leu
465                 470                 475                 480
Pro Phe Phe Glu Lys Gly Lys Glu Glu Gln Ala Lys Leu Asp Tyr Gly
                    485                 490                 495
Asn Ile Leu Asn Pro Tyr Asn Thr Gln Leu Ala Lys Val Glu Val Glu
                    500                 505                 510
Ala Leu Phe Lys Gly Asn Lys Asn Gln Glu Ile Tyr Gln Ala Leu Asp
                    515                 520                 525
Gly Asn Tyr Ala Tyr Glu Phe Gly Ala Phe Lys Ser Val Leu Asn Ser
                    530                 535                 540
Trp Thr Gly Lys Ile Gln His Pro Glu Lys Ala Asp Ile Gln Arg Phe
545                 550                 555                 560
Thr Arg His Leu Glu Gln Val Lys Ile Gly Ser Asn Ser Val Leu Asn
                    565                 570                 575
Gln Pro Gln Thr Thr Lys Glu Gln Val Ile Ser Ser Leu Lys Ser Asn
                    580                 585                 590
Asn Phe Phe Lys Asn Gly His Gln Val Ala Ser Tyr Phe Gln Asp Leu
                    595                 600                 605
Leu Thr Lys Asp Lys Leu Thr Ile Leu Glu Thr Leu Tyr Asp Leu Ala
                    610                 615                 620
Lys Lys Trp Gly Leu Glu Thr Asn Arg Ala Gln Phe Pro Lys Gly Val
625                 630                 635                 640
Phe Gln Tyr Thr Lys Asp Ile Phe Ala Glu Ala Asp Lys Leu Lys Phe
                    645                 650                 655
Leu Glu Leu Lys Lys Lys Asp Pro Tyr Asn Gln Ile Lys Glu Ile His
                    660                 665                 670
Gln Leu Ser Phe Asn Ile Leu Ala Arg Asn Asp Val Ile Lys Ser Asp
                    675                 680                 685
Gly Phe Tyr Gly Val Leu Leu Pro Gln Ser Val Lys Thr Glu Leu
                    690                 695                 700
Glu Gly Lys Asn Glu Ala Gln Ile Phe Glu Ala Leu Lys Lys Tyr Ser
705                 710                 715                 720
Leu Ile Glu Asn Ser Ala Phe Lys Thr Thr Ile Leu Asp Lys Asn Leu
                    725                 730                 735
```

Leu Glu Gly Thr Asp Phe Lys Thr Phe Gly Asp Phe Leu Ala Phe Phe
                740                 745                 750

Leu Lys Ala Ala Gln Phe Asn Asn Phe Ala Pro Trp Ala Lys Leu Asp
                755                 760                 765

Asp Asn Leu Gln Tyr Ser Phe Glu Ala Ile Lys Lys Gly Glu Thr Thr
            770                 775                 780

Lys Glu Gly Lys Arg Glu Val Asp Lys Val Lys Glu Leu Asp
785                 790                 795                 800

Asn Lys Ile Lys Gly Ile Leu Pro Gln Pro Ala Lys Pro Glu Ala
                805                 810                 815

Ala Lys Pro Val Ala Ala Lys Pro Glu Thr Thr Lys Pro Val Ala Ala
                820                 825                 830

Lys Pro Glu Ala Ala Lys Pro Glu Ala Ala Lys Pro Val Ala Ala Lys
                835                 840                 845

Pro Glu Ala Ala Lys Pro Val Ala Ala Lys Pro Glu Ala Ala Lys Pro
            850                 855                 860

Val Ala Ala Lys Glu Ala Ala Lys Pro Val Ala Ala Lys Pro Glu Ala
865                 870                 875                 880

Ala Lys Pro Val Ala Thr Asn Thr Gly Phe Ser Leu Thr Asn Lys Pro
                885                 890                 895

Lys Glu Asp Tyr Phe Pro Met Ala Phe Ser Tyr Lys Leu Glu Tyr Thr
            900                 905                 910

Asp Glu Asn Lys Leu Ser Leu Lys Thr Pro Glu Ile Asn Val Phe Leu
            915                 920                 925

Glu Leu Val His Gln Ser Glu Tyr Glu Gln Glu Ile Ile Lys Glu
                930                 935                 940

Leu Asp Lys Thr Val Leu Asn Leu Gln Tyr Gln Phe Gln Glu Val Lys
945                 950                 955                 960

Val Thr Ser Asp Gln Tyr Gln Lys Leu Ser His Pro Met Met Thr Glu
                965                 970                 975

Gly Ser Ser Asn Gln Gly Lys Lys Ser Glu Gly Thr Pro Asn Gly Lys
            980                 985                 990

Lys Ala Glu Gly Ala Pro Asn Gln Gly Lys Ala Glu Gly Thr Pro
            995                 1000                1005

Asn Gln Gly Lys Lys Ala Glu Gly Ala Pro Ser Gln Gln Ser Pro
            1010                1015                1020

Thr Thr Glu Leu Thr Asn Tyr Leu Pro Asp Leu Gly Lys Lys Ile
            1025                1030                1035

Asp Glu Ile Ile Lys Lys Gln Gly Lys Asn Trp Lys Thr Glu Val
            1040                1045                1050

Glu Leu Ile Glu Asp Asn Ile Ala Gly Asp Ala Lys Leu Leu Tyr
            1055                1060                1065

Phe Ile Leu Arg Asp Asp Ser Lys Ser Gly Asp Pro Lys Lys Ser
            1070                1075                1080

Ser Leu Lys Val Lys Ile Thr Val Lys Gln Ser Asn Asn Asn Gln
            1085                1090                1095

Glu Pro Glu Ser Lys
    1100

<210> SEQ ID NO 12
<211> LENGTH: 316
<212> TYPE: PRT
<213> ORGANISM: Mycoplasma hyopneumoniae

<400> SEQUENCE: 12

Lys Leu Asp Asp Asn Leu Gln Tyr Ser Phe Glu Ala Ile Lys Lys Gly
1               5                   10                  15

Glu Thr Thr Lys Glu Gly Lys Arg Glu Val Asp Lys Lys Val Lys
            20                  25                  30

Glu Leu Asp Asn Lys Ile Lys Gly Ile Leu Pro Gln Pro Pro Ala Ala
            35                  40                  45

Lys Pro Glu Ala Ala Lys Pro Val Ala Ala Lys Pro Glu Thr Thr Lys
        50                  55                  60

Pro Val Ala Ala Lys Pro Glu Ala Ala Lys Pro Glu Ala Ala Lys Pro
65                  70                  75                  80

Val Ala Ala Lys Pro Glu Ala Ala Lys Pro Val Ala Ala Lys Pro Glu
                85                  90                  95

Ala Ala Lys Pro Val Ala Ala Lys Pro Glu Ala Ala Lys Pro Val Ala
            100                 105                 110

Ala Lys Pro Glu Ala Ala Lys Pro Val Ala Thr Asn Thr Gly Phe Ser
        115                 120                 125

Leu Thr Asn Lys Pro Lys Glu Asp Tyr Phe Pro Met Ala Phe Ser Tyr
    130                 135                 140

Lys Leu Glu Tyr Thr Asp Glu Asn Lys Leu Ser Leu Lys Thr Pro Glu
145                 150                 155                 160

Ile Asn Val Phe Leu Glu Leu Val His Gln Ser Glu Tyr Glu Glu Gln
                165                 170                 175

Glu Ile Ile Lys Glu Leu Asp Lys Thr Val Leu Asn Leu Gln Tyr Gln
            180                 185                 190

Phe Gln Glu Val Lys Val Thr Ser Asp Gln Tyr Gln Lys Leu Ser His
        195                 200                 205

Pro Met Met Thr Glu Gly Ser Ser Asn Gln Gly Lys Lys Ser Glu Gly
    210                 215                 220

Thr Pro Asn Gln Gly Lys Lys Ala Glu Gly Ala Pro Asn Gln Gly Lys
225                 230                 235                 240

Lys Ala Glu Gly Thr Pro Asn Gln Gly Lys Lys Ala Glu Gly Ala Pro
                245                 250                 255

Ser Gln Gln Ser Pro Thr Thr Glu Leu Thr Asn Tyr Leu Pro Asp Leu
            260                 265                 270

Gly Lys Lys Ile Asp Glu Ile Ile Lys Lys Gln Gly Lys Asn Trp Lys
        275                 280                 285

Thr Glu Val Glu Leu Ile Glu Asp Asn Ile Ala Gly Asp Ala Lys Leu
    290                 295                 300

Leu Tyr Phe Ile Leu Arg Asp Asp Ser Lys Ser Gly
305                 310                 315

<210> SEQ ID NO 13
<211> LENGTH: 158
<212> TYPE: PRT
<213> ORGANISM: Mycoplasma hyopneumoniae

<400> SEQUENCE: 13

Lys Leu Asp Asp Asn Leu Gln Tyr Ser Phe Glu Ala Ile Lys Lys Gly
1               5                   10                  15

Glu Thr Thr Lys Glu Gly Lys Arg Glu Val Asp Lys Lys Val Lys
            20                  25                  30

Glu Leu Asp Asn Lys Ile Lys Gly Ile Leu Pro Gln Pro Pro Ala Ala
            35                  40                  45

-continued

```
Lys Pro Glu Ala Ala Lys Pro Val Ala Ala Lys Pro Glu Thr Thr Lys
    50                  55                  60

Pro Val Ala Ala Lys Pro Glu Ala Ala Lys Pro Glu Ala Ala Lys Pro
65                  70                  75                  80

Val Ala Ala Lys Pro Glu Ala Ala Lys Pro Val Ala Ala Lys Pro Glu
                85                  90                  95

Ala Ala Lys Pro Val Ala Ala Lys Pro Glu Ala Ala Lys Pro Val Ala
            100                 105                 110

Ala Lys Pro Glu Ala Ala Lys Pro Val Ala Thr Asn Thr Gly Phe Ser
        115                 120                 125

Leu Thr Asn Lys Pro Lys Glu Asp Tyr Phe Pro Met Ala Phe Ser Tyr
    130                 135                 140

Lys Leu Glu Tyr Thr Asp Glu Asn Lys Leu Ser Leu Lys Thr
145                 150                 155

<210> SEQ ID NO 14
<211> LENGTH: 44
<212> TYPE: PRT
<213> ORGANISM: Mycoplasma hyopneumoniae

<400> SEQUENCE: 14

Leu Val Ala Glu Phe Asn Phe Ser Leu Lys Lys Ile Thr Glu Lys Leu
1               5                   10                  15

Asn Gln Gln Ile Glu Asn Leu Ser Thr Lys Ile Thr Asn Phe Ala Asp
            20                  25                  30

Glu Lys Thr Ser Ser Gln Lys Asp Pro Ser Thr Leu
        35                  40

<210> SEQ ID NO 15
<211> LENGTH: 611
<212> TYPE: PRT
<213> ORGANISM: Mycoplasma hyopneumoniae

<400> SEQUENCE: 15

Glu Asp Asn Pro Glu Gly Asp Trp Ile Thr Leu Gly Arg Met Glu Lys
1               5                   10                  15

Leu Val Lys Glu Val Ile Gln Tyr Lys Lys Glu Gly Thr Lys Thr Phe
            20                  25                  30

Leu Asp Asp Glu Val Ala Lys Thr Leu Tyr Tyr Leu Asp Phe His His
        35                  40                  45

Leu Pro Gln Ser Lys Lys Asp Leu Glu Glu Tyr Lys Glu Lys His Lys
    50                  55                  60

Asn Lys Phe Ile Asn Glu Lys Pro Ala Thr Ala Thr Ser Gln Ala Lys
65                  70                  75                  80

Pro Asp Gln Ala Lys Asn Glu Lys Glu Val Lys Pro Glu Ser Ala Gln
                85                  90                  95

Ala Glu Ser Ser Ser Ser Asn Ser Asn Asp Ser Asn Ser Lys Thr Thr
            100                 105                 110

Ser Ser Ser Ser Met Ala Gly Thr Thr Gln Asn Lys Ser Thr Asx Glu
        115                 120                 125

Thr Pro Asn Ser Ser Ser Asn Ser Thr Pro Thr Ser Ser Ala Thr Thr
    130                 135                 140

Ser Thr Thr Ser Ser Thr Gln Ala Ala Ala Thr Ser Ala Ser Ser Ala
145                 150                 155                 160

Lys Val Lys Thr Thr Lys Phe Gln Glu Gln Glu Lys Gln Gln Val Lys
                165                 170                 175
```

```
Glu Gln Lys Gln Lys Gln Glu Lys Thr Lys Glu Thr Asn Gln Leu Leu
                180                 185                 190

Asp Thr Lys Thr Asn Lys Glu Asn Leu Gly Gly Leu Ile Leu Trp Asp
            195                 200                 205

Phe Leu Val Asn Ser Lys Tyr Lys Thr Leu Pro Gly Thr Thr Trp Asp
        210                 215                 220

Phe Leu Val Glu Pro Asp Ser Phe Asn Asp Arg Leu Lys Ile Thr Ala
225                 230                 235                 240

Ile Leu Lys Glu Asn Thr Ser Gln Ala Lys Ser Asn Pro Asp Ser Lys
                245                 250                 255

Asn Leu Thr Ser Leu Thr Arg Asn Leu Ile Ile Lys Gly Val Met Ala
            260                 265                 270

Asn Lys Tyr Ile Asp Tyr Leu Val Gln Glu Asp Pro Val Leu Leu Val
        275                 280                 285

Asp Tyr Thr Arg Arg Asn Gln Ile Lys Thr Glu Arg Glu Gly Gln Leu
        290                 295                 300

Ile Trp Ser Gln Leu Ala Ser Pro Gln Met Ala Ser Pro Glu Pro Glu
305                 310                 315                 320

Lys Thr Lys Leu Glu Ile Thr Glu Gly Leu Arg Val Lys Lys Gly
                325                 330                 335

Gly Thr Lys Ile Lys Glu Gly Ile Lys Asn Gly Ser Ser Arg Gly Asn
            340                 345                 350

Thr Asn Thr Asn Ser Lys Pro Asn Lys Lys Leu Val Leu Leu Lys Gly
        355                 360                 365

Ala Ile Lys Asn Pro Gly Thr Lys Lys Glu Trp Ile Leu Val Gly Ser
        370                 375                 380

Gly Ile Lys Asp Asn Asn Asn Gly Gly Ser Asn Asn Asn Ser Asn Thr
385                 390                 395                 400

Gln Ile Trp Ile Thr Arg Leu Gly Thr Ser Val Gly Ser Leu Lys Thr
                405                 410                 415

Glu Gly Glu Thr Val Leu Gly Ile Ser Asn Asn Asn Ser Gln Glu Val
            420                 425                 430

Leu Trp Thr Thr Ile Lys Ser Lys Leu Glu Asn Glu Asn Pro Ser Asp
        435                 440                 445

Asn Asn Gln Ile Gln Tyr Ser Pro Ser Thr His Ser Leu Thr Thr Asn
450                 455                 460

Ser Arg Ser Asn Thr Gln Gln Ser Gly Arg Asn Gln Ile Lys Ile Thr
465                 470                 475                 480

Asn Thr Gln Arg Lys Thr Thr Thr Ser Pro Ser Gln Asn Leu Ser Gln
                485                 490                 495

Asn Pro Asp Pro Asn Gln Ile Asp Val Arg Leu Gly Leu Leu Val Gln
            500                 505                 510

Asp Lys Lys Leu His Leu Trp Trp Ile Ala Asn Asp Ser Ser Asp Glu
        515                 520                 525

Pro Glu His Ile Thr Ile Asp Phe Ala Glu Gly Thr Phe Asn Tyr Asp
        530                 535                 540

Asp Leu Asn Tyr Val Gly Gly Leu Leu Lys Asn Thr Asn Asn Asn
545                 550                 555                 560

Asn Thr Gln Ala Gln Asp Asp Glu Gly Asp Gly Tyr Leu Ala Leu Lys
                565                 570                 575

Gly Leu Gly Ile Tyr Glu Phe Pro Asp Asp Glu Ser Ile Asp Gln Ala
            580                 585                 590

Ala Thr Val Glu Lys Ala Glu Arg Leu Tyr Lys His Phe Met Gly Leu
```

-continued

```
        595                 600                 605

Phe Arg Glu
    610

<210> SEQ ID NO 16
<211> LENGTH: 241
<212> TYPE: PRT
<213> ORGANISM: Mycoplasma hyopneumoniae

<400> SEQUENCE: 16

Gln Leu Thr Gln Glu Gly Phe Lys Leu Thr Asn Pro Ile Lys Phe Gln
1               5                   10                  15

Gln Asn Gln Ser Lys Thr Lys Glu Asn Ile Ala Arg Thr Val Asn Ile
            20                  25                  30

Ser Tyr Leu Ala Phe Lys Pro Lys Asn Ile Asn Asp Tyr Lys Lys His
        35                  40                  45

Tyr Leu Leu Ala Asp Ser Asp Gly Asn Gly Leu Phe Ile Gln Lys Ile
    50                  55                  60

Lys Asn Thr Glu Lys Thr Thr Gln Asn Ser Asp Ile Thr Phe Ile Lys
65                  70                  75                  80

Pro Glu Asn Leu Asp Gln Lys Asn Lys Asp Glu Thr Gln Gln Lys Gln
                85                  90                  95

Val Asp Gly Ser Tyr Leu Tyr Gln Asn Lys Lys Ser Leu Tyr Ser Leu
            100                 105                 110

Ala Asn Leu Phe Pro Pro Glu Leu Ile Asp Lys Gln Ala Val Ile Leu
        115                 120                 125

Gly Pro Asn Ser Leu Ala Ile Val Glu Leu Ala Asn Arg Ile Gly Glu
    130                 135                 140

Asn Arg Phe Tyr Arg Gln Glu Leu Arg Asn Ser Ser Pro Phe Ser Leu
145                 150                 155                 160

Glu Lys Ser Lys Glu Ser Val Glu Ile Ser Ala Phe Ser Ser Ser Asn
                165                 170                 175

Tyr Gln Leu Asn Ser Lys Thr Ser Leu Asn Leu Asn Gly Lys Thr Ile
            180                 185                 190

Tyr Asn Ile Asn Pro Val Ile Gly Pro Asn Pro Lys Lys Thr Thr Asp
        195                 200                 205

Lys Asn Gly Ser Asn Asn Glu Lys Ile Asn Lys Asn Ser Ser Ile Ile
    210                 215                 220

Leu Lys Gly Ile Ala Val Tyr Arg Asn Ala Phe Ile Lys Ala Tyr Ile
225                 230                 235                 240

Lys

<210> SEQ ID NO 17
<211> LENGTH: 470
<212> TYPE: PRT
<213> ORGANISM: Mycoplasma hyopneumoniae

<400> SEQUENCE: 17

Asn Lys Ile Gly Ile Asp Leu Gly Val Leu Lys Lys Tyr Ile Ser Asn
1               5                   10                  15

Asn Gln Gly Ile Glu Tyr Thr Phe Asp Ile Ala Asn Ala Lys Ile Arg
            20                  25                  30

Asp Ala Gln Gly Asp Gly Ile Thr Ser His Ile Glu Ile Pro Val Thr
        35                  40                  45

Ile Ser Leu Trp Ser Ser Phe Phe Gly Asp Ser Asp Asn Val Leu Leu
    50                  55                  60
```

-continued

```
Lys Ser Lys Thr Glu Thr Phe Ile Ile Pro Tyr Phe Gln Lys Glu Thr
65                  70                  75                  80

Thr Ser Glu Ser Lys Asp Gln Lys Val Gly His Thr Gln Lys Glu Leu
            85                  90                  95

Asp Leu Asn Gln Lys Leu Val Tyr Gln Leu Ser Glu Leu Pro Gly Thr
                100                 105                 110

Ser Thr Gln Gly Ser Ser Gly Ser Ser Thr Gln Thr Glu Gln Ile Lys
                115                 120                 125

Glu Val Lys Leu Pro Thr Leu Thr Ala Phe Ile Ser Lys Gln Glu Leu
    130                 135                 140

Glu Ala Leu Ile Asp Gly Asp Lys Asn Leu Ala Ser Gln Pro Thr Ser
145                 150                 155                 160

Gln Ala Val Ser Val Ser Gln Val Lys Ala Thr Glu Phe Gln Gln Gln
                165                 170                 175

Asp Ala Asn Ser Thr Asn Ser Ser Pro Thr Ser Pro Ser Pro Ser Pro
                180                 185                 190

Thr Ser Pro Ser Pro Ala Ser Pro Ser Ser Pro Ser Pro Thr Ser
            195                 200                 205

Pro Lys Asn Leu Asp Glu Asn Ile Gly Val Pro Asn Pro Arg Phe Glu
    210                 215                 220

Glu Ile Lys Lys Ile Ile Ser Ser Glu Phe Thr Tyr Lys Tyr Asn Phe
225                 230                 235                 240

Arg Ala Asn Glu Ala Leu Leu Asp Ala Trp Val Gly Lys Gln Asn Phe
                245                 250                 255

Pro Ser Leu Lys Asp Ile Ser Gln Phe Arg Ser Asp Gln Arg Leu Ala
                260                 265                 270

Lys Asp Tyr Lys Leu Val Asn Leu Lys Ser Asn Lys Phe Leu Glu Asp
                275                 280                 285

Tyr Asp Val Leu Ala Phe Tyr Ala Asn Leu Val Gln Lys Asp Pro Arg
    290                 295                 300

Glu Val Leu Gln Tyr Leu Phe Glu Ile Ala Arg Ala Asn Asn Leu Ile
305                 310                 315                 320

Gly Pro Glu Glu Lys Leu Asp Leu Asn Gln Ile Glu Glu Asp Gly Ile
                325                 330                 335

Phe Arg Arg Ala Lys Ala Ile Lys Leu Ile Asp Lys Ser Ser Asn Asn
                340                 345                 350

Gln Gly Ile Tyr Gly Phe Ser Phe Asn Asn Gln Phe Leu Lys Phe His
                355                 360                 365

Glu Arg Gly Trp Met Ser Thr Leu Tyr Leu Pro Asn Glu Ala Lys Thr
            370                 375                 380

Lys Leu Ala Asp Tyr Gln Asn Leu Leu Ser Ala Gly Ile Ser Asp Thr
385                 390                 395                 400

Lys Ile Phe Ser Glu Leu Asn Lys Ile Gln Pro Leu Asp Leu Asn Ile
                405                 410                 415

Lys Thr Gln Ser Ser Asp Ser Ser Lys Ser Asp Ser Ser Asp Ser
            420                 425                 430

Asp Asp Ala Lys Thr Thr Ser Thr Lys Gln Asp Leu Leu Lys Leu Thr
                435                 440                 445

Ser Leu Lys Ser Gln Ile Glu Ala Ile Val Lys Lys Tyr Glu Thr Glu
    450                 455                 460

Ser Lys Lys Tyr Leu Gly
465             470
```

<210> SEQ ID NO 18
<211> LENGTH: 546
<212> TYPE: PRT
<213> ORGANISM: Mycoplasma hyopneumoniae

<400> SEQUENCE: 18

```
Ser Gly Ala Lys Ser Thr Ile Ile Phe Glu Glu Ile Ala Glu Leu Asp
1               5                   10                  15

Pro Lys Val Lys Glu Lys Val Gly Ala Asp Val Tyr Gln Leu Lys Phe
            20                  25                  30

His Tyr Ala Ile Gly Phe Asp Asp Asn Ala Gly Lys Phe Asn Gln Glu
        35                  40                  45

Val Ile Arg Ser Ser Ser Arg Thr Ile Tyr Leu Lys Thr Ser Gly Lys
    50                  55                  60

Ser Lys Leu Glu Ala Asp Thr Ile Asp Gln Leu Asn Gln Ala Val Lys
65                  70                  75                  80

Asn Ala Pro Leu Gly Leu Gln Ser Phe Tyr Leu Asp Thr Glu Arg Phe
                85                  90                  95

Gly Val Phe Gln Lys Leu Ala Thr Ser Leu Ala Val Gln His Lys Gln
            100                 105                 110

Lys Glu Lys Thr Leu Pro Lys Lys Leu Asn Asn Asp Gly Tyr Thr Leu
        115                 120                 125

Ile His Asp Lys Leu Lys Lys Pro Val Ile Pro Gln Ile Ser Ser Ser
    130                 135                 140

Pro Glu Lys Asp Trp Phe Glu Gly Lys Leu Asn Gln Asn Gly Gln Ser
145                 150                 155                 160

Gln Asn Val Asn Val Ser Thr Phe Gly Ser Ile Ile Glu Ser Pro Tyr
                165                 170                 175

Phe Ser Thr Asn Phe Gln Glu Asp Ala Asp Leu Asp Gln Asp Gly Gln
            180                 185                 190

Asp Asp Ser Arg Gln Gly Asn Asn Ser Leu Asp Asn Gln Glu Ala Gly
        195                 200                 205

Leu Leu Lys Lys Leu Ala Ile Leu Leu Gly Asn Gln Phe Ile Gln Tyr
    210                 215                 220

Tyr Gln Gln Asn Asp Lys Glu Ile Glu Phe Glu Ile Ile Asn Val Glu
225                 230                 235                 240

Lys Val Ser Glu Leu Ser Phe Arg Val Glu Phe Lys Leu Ala Lys Thr
                245                 250                 255

Leu Glu Asp Asn Gly Lys Thr Ile Arg Val Leu Ser Asp Glu Thr Met
            260                 265                 270

Ser Leu Ile Val Asn Thr Thr Ile Glu Lys Thr Pro Glu Met Ser Ala
        275                 280                 285

Val Pro Glu Val Phe Asp Thr Lys Trp Val Glu Gln Tyr Asp Pro Arg
    290                 295                 300

Thr Pro Leu Ala Ala Lys Thr Lys Phe Val Leu Lys Phe Lys Asp Gln
305                 310                 315                 320

Ile Pro Val Asp Gly Ser Gly Asn Ile Ser Asp Lys Trp Leu Ala Ser
                325                 330                 335

Ile Pro Leu Val Ile His Gln Gln Met Leu Arg Leu Ser Pro Val Val
            340                 345                 350

Lys Thr Ile Arg Glu Leu Gly Leu Lys Thr Glu Gln Gln Gln Gln Gln
        355                 360                 365

Gln Gln Gln Gln Gln Gln Gln Gln Pro Gln Lys Lys Ala Val Arg Lys
    370                 375                 380
```

```
Glu Glu Glu Leu Glu Thr Tyr Asn Pro Lys Asp Glu Phe Asn Ile Leu
385                 390                 395                 400

Asn Pro Leu Thr Lys Ala His Arg Leu Thr Leu Ser Asn Leu Val Asn
                405                 410                 415

Asn Asp Pro Asn Tyr Lys Ile Glu Asp Leu Lys Val Ile Lys Asn Glu
            420                 425                 430

Ala Gly Asp His Gln Leu Ala Phe Ser Leu Arg Ala Asn Asn Ile Lys
        435                 440                 445

Arg Leu Met Asn Thr Pro Ile Thr Phe Ala Asp Tyr Asn Pro Phe Phe
    450                 455                 460

Tyr Tyr Asn Glu Asp Trp Arg Ser Ile Asp Lys Tyr Leu Asn Asn Lys
465                 470                 475                 480

Gly Asn Val Ser Ser His Gln Gln Gln Ala Ala Gly Gly Asn Gln Gly
                485                 490                 495

Ser Gly Leu Ile Gln Arg Leu Asn Lys Asn Ile Lys Pro Glu Thr Phe
            500                 505                 510

Thr Pro Ala Leu Ile Ala Leu Lys Arg Asp Asn Asn Thr Asn Leu Ser
        515                 520                 525

Asn Tyr Ser Asp Lys Ile Ile Met Ile Lys Pro Lys Tyr Leu Val Glu
    530                 535                 540

Arg Ser
545

<210> SEQ ID NO 19
<211> LENGTH: 20
<212> TYPE: PRT
<213> ORGANISM: Mycoplasma hyopneumoniae

<400> SEQUENCE: 19

Ala Ala Lys Pro Glu Ala Ala Lys Pro Val Ala Ala Lys Pro Glu Thr
1               5                   10                  15

Thr Lys Pro Val
            20

<210> SEQ ID NO 20
<211> LENGTH: 7
<212> TYPE: PRT
<213> ORGANISM: Artificial Sequence
<220> FEATURE:
<223> OTHER INFORMATION: Synthesized Histidine tag

<400> SEQUENCE: 20

Met  His  His  His  His  His  His
1                    5

<210> SEQ ID NO 21
<211> LENGTH: 20
<212> TYPE: DNA
<213> ORGANISM: Artificial Sequence
<220> FEATURE:
<223> OTHER INFORMATION: 5 prime Tag

<400> SEQUENCE: 21 aat taa ccc tca cta aag gg                                            20

<210> SEQ ID NO 22
<211> LENGTH: 18
<212> TYPE: DNA
<213> ORGANISM: Artificial Sequence
<220> FEATURE:
<223> OTHER INFORMATION: 3 prime Tag
```

```
<400> SEQUENCE: 22 tat ggt cga ata agt taa                                              18

<210> SEQ ID NO 23
<211> LENGTH: 18
<212> TYPE: DNA
<213> ORGANISM: Artificial Sequence
<220> FEATURE:
<223> OTHER INFORMATION: 3 prime Tag

<400> SEQUENCE: 23 tta act tat tcg acc ata                                              18
```

COMPOUNDS FOR DETECTING AND TREATING *MYCOPLASMA HYOPNEUMONIAE*

CROSS-REFERENCE TO RELATED APPLICATION

This application claims priority to Canadian Application No. 2,940,637 filed Aug. 30, 2016, which hereby is incorporated by reference in its entirety.

FIELD

The present invention relates to aptamers, nucleic acid molecules, synthetic antibodies binding to *M. hyopneumoniae*, which can be utilized for detecting and treating *M. Hyopneumoniae* infection, particularly in swines, and pharmaceutical composition containing same.

BACKGROUND

*M. hyopneumoniae* are bacteria known to cause the Porcine Enzootic Pneumonia (PEP), a highly contagious and chronic disease affecting pigs[1]. As with other mollicutes, *M. Hyopneumoniae* bacterium is small in size, (400-1200 nm), has a small genome (893-920 kilo-base pairs (kb)) and lacks a cell wall[1-2]. It is considered to be difficult to grow in laboratories due to its complex nutritional requirements. This bacterium is a major concern in the livestock industry as it causes a significant reduction in the growing weight of pigs, and is a known potentiation vector for SIV[3], and *M. hyopneumoniae*[4] Losses in the U.S.A. have been previously estimated at 400 million to 1 billion dollars per annum[5]. Porcine enzootic pneumonia is endemic worldwide and *M. Hyopneumoniae* is present in almost every pig herd, and lesions of enzootic pneumonia are consistently observed in >50% of swine at slaughter[6]. Although reported prevalence varies according to different researchers, inspections carried out in several countries show that typical lesions of *M. hyopneumoniae* is observed in 50-95% of slaughtered pigs, whilst 60-99% of herds may be positive to *M. hyopneumoniae*[1].

To date, vaccination strategies, which constitute the basis of *M. hyopneumoniae* control, have been directed at preventing morbidity and mortality. Control of *M. hyopneumoniae* infections, apart from improvements in husbandry and the environment, is primarily with the use of antimicrobial products, but they have limitations. Medicated protection only lasted during treatment and for a short period afterwards such that *M. hyopneumoniae* is not completely eliminated and the herd have not necessarily developed much immunity (Haesebrouck,[8]). This has led to the development of pulse medication and strategic medication programs to prolong the medicinal protection or to target the stress periods when disease was likely to flare up.

Most antibiotics only treat *M. hyopneumoniae* and not the secondary bacteria so a variety of combinations of antibiotics are used to broaden the control effect. In the case of outbreaks, antibiotics such as tetracyclines, lincomycin or tiamulin, show low minimum inhibitory concentration (MIC) (i.e. the lowest concentration of an antimicrobial that will inhibit the visible growth of a microorganism). Fluoroquinolones are also effective but, owing to current concerns regarding antimicrobial resistance, their use in pigs should be limited[7, 8]. The efficacy of doxycycline has been demonstrated in the treatment of porcine enzootic pneumonia (PEP).

Although the current antimicrobial medication and vaccination confers beneficial effects in most infected herds, the effects are variable between herds. The variable results may be due to different factors such as improper medication/vaccine storage conditions, different injection techniques, antigenic differences between field strains and vaccine strains, presence of other diseases at the time of treatment/vaccination, interferences of vaccine-induced immune responses by maternally derived (colostral) antibodies, etc. Hence there is plenty of space to develop much better anti-microbial drugs.

Treatment of this disease is limited to antibiotics, which are currently ineffective, as they do not completely remove the infection[7]. At best, vaccines are found to reduce the severity of the disease but do not prevent the disease from occurring in non-infected pigs[8].

Strictly speaking, *M. hyopneumoniae* is a pathogen of swine and alternate hosts or intermediary vectors have not been found. All electron microscopy studies of infected lung tissues have shown that *M. hyopneumoniae* interacts almost exclusively with (i) cilia on the epithelial surfaces that lines the trachea, the bronchi and the bronchioles in the porcine upper respiratory tract, and with (ii) pulmonary alveolar macrophages (PAM)[1,9]. More specifically, this bacterium is found attached along the entire length of the cilia but rarely to the epithelial cell body[1-2].

To survive and proliferate as an infectious agent, *M. hyopneumoniae* must (a) enter the respiratory tract of its host, (b) traverse mucous layers, (c) resist the mucociliary escalator, (d) adhere and colonize the epithelial cilia, (d) secure essential nutrients for growth and replication, (f) evade immune response, and (g) repeat the cycle of infection by transmission to new hosts via airborne mucosal droplets. The colonization of the upper respiratory track results in the destruction of the mucociliary escalator via ciliostasis (they cause cilia to stop beating), loss of cilia and eventually epithelial cell death; which is the source of the lesions found in the lungs of pigs with porcine enzootic pneumonia[1]. The analysis of the literature shows that the mechanisms being utilized by *M. hyopneumoniae* to colonize respiratory cilia requires multiple adhesins and strategies to avoid immune detection. For example, heparin effectively blocks the binding of *M. Hyopneumoniae* to porcine cilia indicating that *M. hyopneumoniae* is reliant on the presentation of heparin-binding proteins on its cell surface. This is consistent with the fact that proteoglycans with highly sulphated glycosaminoglycan (GAG) side chains are prominently displayed on the surface of ciliated epithelium lining the porcine respiratory tract[10]. This might also explain why the immune response to the presence of *M. Hyopneumoniae* is slow and ineffective[7-8].

As of April 2012, five separate strains (232, 7448, 7422, Perdue Master Seed (PMS), and J) of this *mycoplasma* have had their genomes sequenced, making it the most sequenced *mycoplasma*[11]; the first three being virulent, the forth one mildly virulent, and the last one with no virulence. Current research is mainly focused on identifying the "right adhesins" with a final goal of developing an effective vaccine that prevents *Mycoplasma Hyopneumoniae* from attaching to lung cilia.

SUMMARY

It would be advantageous to have improved compositions, which can diagnose and treat *M. hyopneumoniae* infection. Here, we describe ssDNA aptamers for *M. Hyopneumoniae*. These were developed using SELEX method and the binding domain of the P97 surface protein as the target rather than the entire *mycoplasma* organism. The characterization of the aptamers and their use as an analytical tool for the detection of *M. Hyopneumoniae* were evaluated using various enzyme-linked antibody-aptamer assays (ELISA). According to one aspect, the aptamers were then further modified to permit binding on various biosensors surfaces for a more rapid and convenient detection of *M. Hyopneumoniae*.

We disclose herein nucleic acid molecules comprising at least one polynucleotide sequence capable of specifically binding various peptidic complexes participating in the *M. hyopneumoniae* infection, including a *M. hyopneumoniae* polypeptide or a host cell polypeptide.

According to an embodiment, we disclose a nucleic acid molecule comprising at least one polynucleotide sequence capable of specifically binding to: (i) a polypeptide expressed by *M. hyopneumoniae*; or (ii) a host molecule expressed by a host organism; wherein the polypeptide or the host molecule is involved in binding *M. hyopneumoniae* to the host organism.

The polynucleotide sequences are capable of:

a) binding a region of the $P97_{\{768-1082\}}$, $P97_{\{768-1050\}}$, $P97_{\{768-925\}}$, $P116_{\{700-1010\}}$, $P102_{\{1-324\}}$, or $P102_{\{1-529\}}$ surface proteins of *M. hyopneumoniae* or a fragment thereof having at least 80%, 85%, 90% or 95 identity with $P97_{\{768-1082\}}$, $P97_{\{768-1050\}}$, $P97_{\{768-925\}}$, $P116_{\{700-1010\}}$, $P102_{\{1-324\}}$, or $P102_{\{1-529\}}$ that control binding of the *Mycoplasma* onto the cilia and/or pulmonary alveolar macrophages (PAM);

b) binding to a surface protein of *M. hyopneumoniae* carrying a motif| AAKPE| AAKPV| AAKPE| TTKPV| or a motif that has at least an 80%, 85%, 90%, or 95% identity with said motif; or c) binding to P97, P102, P116, P146, P216, or P159 surface proteins of *M. Hyopneumoniae* or a fragment having at least 80%, 85%, 90%, or 95% sequence identity with the P97, P102, P116, P146, P216, and P159 surface proteins, that control binding of *M. hyopneumoniae* onto the cilia and/or pulmonary alveolar macrophages (PAM).

According to further features, the polynucleotide sequence is APT3Cooc10 (SEQ ID NO:1), APT3Cooc4 (SEQ ID NO:2), APT3Cooc2 (SEQ ID NO:3), APT3Histo1 (SEQ ID NO:4), APT3Cooc3 (SEQ ID NO:5), APT3Histo2 (SEQ ID NO:6), APT3Histo4 (SEQ ID NO:7), APT3Histo5 (SEQ ID NO:8), APT3Histo9 (SEQ ID NO:9), or APT3Cooc7 (SEQ ID NO:10) or is a sequence having at least 60%, 65%, 75%, 80%, 85%, 90%, or 95% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

According to further features, the polynucleotide sequence is APT3Cooc10 (SEQ ID NO:1), APT3Histo1 (SEQ ID NO:4), or APT3Cooc3 (SEQ ID NO:5).

According to still further features in the described embodiments the host cell molecule are glycolipids found on the cilia of porcine pulmonary epithelium cells, such as GM3, La, Lb, or Lc. (Q. Zhang et al., Glycolipid receptors for attachment of *Mycoplasma Hyopneumoniae* to porcine respiratory ciliated cells. *Infection & Immunity*, 1994, vol. 62, pp. 4367-4373. Also C. Hermans & A. Bernard, Lung epithelium-specific proteins: Characteristics and potential applications as markers. *Am. J. of Respi. Crit. Care Med.*, 1999, vol. 159, pp 646-678).

According to still further features in the described embodiments the polynucleotide sequence is single stranded.

According to still further features in the described embodiments the polynucleotide sequence is ssDNA.

According to still further features in the described embodiments the nucleic acid molecule further comprising a detectable label.

According to still further features in the described embodiments the polynucleotide sequence include FDG ([$^{18}$F]-2-fluoro-2-deoxy-D-glucose) and/or PEG modified nucleotides.

According to still further features in the described embodiments the polynucleotide sequence have a length of 10 to 45 nucleotides.

According to still further features in the described embodiments the host molecule is a monosialoganglioside-like receptor at the surface of cilia of porcine pulmonary epithelium cells.

According to another aspect of the present invention there is provided a method of isolating a molecule capable of inhibiting *M. hyopneumoniae* infection, the method comprising: (a) contacting a plurality of nucleic acid molecules with a polypeptide consisting of $P97_{\{768-1082\}}$, $P97_{\{768-1050\}}$, $P97_{\{768-925\}}$, $P116_{\{700-1010\}}$, $P102_{\{1-324\}}$, or $P102_{\{1-529\}}$, or with a polypeptide having at least 80%, 85%, 90% or 95 identity with $P97_{\{768-1082\}}$ $P97_{\{768-1050\}}$, $P97_{\{768-925\}}$, $P116_{\{700-1010\}}$, $P102_{\{1-324\}}$, or $P102_{\{1-529\}}$ (b) identifying at least one nucleic acid molecule from the plurality of nucleic acid molecules capable of specifically binding the polypeptide; and (c) isolating the at least one nucleic acid molecule capable of binding the polypeptide.

According to still further features in the described embodiments the method further comprising generating the plurality of nucleic acid molecules using a combinatorial synthesis approach prior to step (a).

According to still further features in the described embodiments the method further comprising modifying the plurality of nucleic acid molecules prior to step (a) or following step (c).

According to still further features in the described embodiments the method further comprising repeating steps (a) to (c).

According to yet another aspect of the present invention there is provided a pharmaceutical composition comprising a nucleic acid molecule including a polynucleotide sequence capable of specifically binding a peptidic complex participating in *M. hyopneumoniae* infection of cells, in particular a nucleic acid molecule as described hereinbefore, and a physiologically acceptable carrier.

According to a further aspect of the present invention there is provided a composition of matter, preferably a pharmaceutical composition, comprising an anti-microbial agent conjugated to a nucleic acid molecule including a polynucleotide sequence capable of specifically binding a polypeptide participating in *M. hyopneumoniae* infection of cells.

According to still another aspect of the present invention there is provided an article-of-manufacture comprising packaging material and a pharmaceutical composition identified for treating or preventing *M. hyopneumoniae* infection being contained within the packaging material, the pharmaceutical composition including, as an active ingredient, a nucleic acid molecule including a polynucleotide sequence capable of specifically binding a peptide participating in *M. hyopneumoniae* infection of cells, in particular a pharmaceutical composition as described hereinbefore.

According to still further features in the described embodiments the pharmaceutical composition further includes an agent, which may be an immunomodulatory agent, an anti-microbial agent, an antisense molecule, or a ribozyme.

According to yet an additional aspect of the present invention there is provided a method of identifying *M. hyopneumoniae* in a biological sample, the method comprising: (a) contacting the biological sample with a nucleic acid molecule including a polynucleotide sequence capable of specifically binding an *M. hyopneumoniae* peptide; and (b) detecting the nucleic acid molecule bound to the *M. hyopneumoniae* polypeptide in the biological sample, to thereby identify the *M. hyopneumoniae* infection.

According to an additional aspect of the present invention there is provided a method of treating or preventing *M. hyopneumoniae* infection comprising providing to a subject in need thereof, a therapeutically effective amount of a nucleic acid molecule including a polynucleotide sequence capable of specifically binding a polypeptide participating in *M. Hyopneumoniae* infection of cells, thereby treating or preventing the *M. hyopneumoniae* infection.

According to still further features in the described embodiments the providing is implemented by: (i) administering of the nucleic acid molecule; and/or (ii) administering a polynucleotide expressing the nucleic acid molecule.

According to still an additional aspect of the present invention there is provided a method of targeting an anti-microbial agent to *M. hyopneumoniae* infected tissues, the method comprising administering to a subject in need thereof a therapeutic effective amount of the anti-microbial agent conjugated to a nucleic acid molecule including a polynucleotide sequence capable of specifically binding a *M. hyopneumoniae* polypeptide, thereby targeting the anti-microbial agent to the *M. hyopneumoniae* infected tissue.

According to still further features in the described embodiments the polypeptide is selected from the group consisting of $P97_{\{768\text{-}1082\}}$, a RNA-directed RNA polymerase core proteins (structural matrix proteins).

According to still further features in the described embodiments the polynucleotide sequence of APT3-Cooc10 is capable of binding a region of P97 surface protein complex defined by amino acid coordinates $\{768\text{-}1082\}$.

According to still a further aspect of the present invention there is provided a synthetic antibody or antibody fragment comprising an antigen binding site specifically recognizing a polypeptide including an amino acid sequence being at least 60% homologous to P97 as determined using the BestFit software of the Wisconsin sequence analysis package, utilizing the Smith and Waterman algorithm, where gap creation penalty equals 8 and gap extension penalty equals 2, wherein the polypeptide does not include the $P97_{\{768\text{-}1082\}}$ domain of *M. hyopneumoniae*.

According to still a further aspect of the present invention there is provided a method of treating or preventing *M. hyopneumoniae* infection comprising providing to a subject in need thereof, a therapeutically effective amount of a synthetic antibody or antibody fragment including an antigen binding site specifically recognizing a polypeptide including an amino acid sequence being at least 60% homologous to P97 as determined using the BestFit software of the Wisconsin sequence analysis package, utilizing the Smith and Waterman algorithm, where gap creation penalty equals 8 and gap extension penalty equals 2, wherein the polypeptide does not include the $P97_{\{768\text{-}1082\}}$ domain of *M. Hyopneumoniae*.

According to still a further aspect of the present invention there is provided a method of identifying *M. hyopneumoniae* in a biological sample (i.e. diagnostic purposes), the method comprising: (a) contacting the biological sample with a synthetic antibody or antibody fragment including an antigen binding site specifically recognizing a polypeptide including an amino acid sequence being at least 60% homologous to P97 as determined using the BestFit software of the Wisconsin sequence analysis package, utilizing the Smith and Waterman algorithm, where gap creation penalty equals 8 and gap extension penalty equals 2, wherein the polypeptide does not include the $P97_{\{768\text{-}1082\}}$ domain of *M. hyopneumoniae*; and (b) detecting immuno complexes including the synthetic antibody or antibody fragment in the biological sample, to thereby identify *M. Hyopneumoniae* in the biological sample.

According to still further features in the described embodiments the polynucleotide is as set forth in APT3Cooc10, APT3Cooc3, APT3Cooc2, APT3Cooc4, and APT3Histo1.

According to still further features in the described embodiments the nucleic acid sequence is as set forth in APT3Cooc10, APT3Cooc3, APT3Cooc2, APT3Cooc4, and APT3Histo1.

According to still further features in the described embodiments the targeted amino acid sequence is defined by amino acid coordinates $\{768\text{-}1082\}$ of the P97 protein for APT3Cooc10, APT3Cooc3, APT3Cooc2, APT3Cooc4, and APT3Histo1.

According to still further features in the described embodiments the targeted amino acid sequence is defined by amino acid coordinates $\{768\text{-}1050\}$ of the P97 protein for APT3Cooc10, APT3Cooc3, and APT3Histo1.

According to still further features in the described embodiments the targeted amino acid sequence is defined by amino acid coordinates $\{768\text{-}925\}$ of the P97 protein for APT3-Cooc3, APT3Cooc3, APT3Cooc2, APT3Cooc4, and APT3Histo1.

According to still further features in the described embodiments the detecting the immuno complexes is implemented by quantifying intensity of the label following (b).

According to still a further aspect of the present invention there is provided a nucleic acid molecule as set forth in APT3Cooc10, APT3Cooc4, APT3-Cooc3, APT3Cooc2, and APT3Histo1.

According to an additional aspect of the present invention there is provided a nucleic acid molecule comprising at least one polynucleotide sequence capable of specifically binding a peptidic complex, wherein the peptidic complex comprises a polypeptide expressed by *M. hyopneumoniae* and involved in binding to a host organism or a host molecule expressed by the host organism which is a target of *M. hyopneumoniae* for treating or preventing *M. hyopneumoniae* infection in a subject in need thereof.

According to an additional aspect of the present invention there is provided a nucleic acid molecule comprising at least one polynucleotide sequence capable of specifically binding a peptidic complex, wherein the peptidic complex comprises a polypeptide expressed by *M. hyopneumoniae* and involved in binding to a host organism or a host molecule expressed by the host organism which is a target of *M. hyopneumoniae* for the manufacture of a medicament for treating or preventing *M. hyopneumoniae* infection in a subject in need thereof.

According to an additional aspect of the present invention there is provided an antiviral agent for treating or preventing *M. hyopneumoniae* infection in a subject in need thereof.

According to an additional aspect of the present invention, the subject is a pig.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 4a-j show schematic illustrations of proposed secondary structures as generated by QuickFold 3.0 software (OM. Zuker, MFold web server for nucleic acid folding and hybridization prediction. Nucleic Acid Research, 2003, vol. 31, pp. 3409-3415) of the APT3Cooc10 aptamer (FIG. 4a), the APT3Cooc2 aptamer (FIG. 4b), the APT3Cooc3 (FIG. 4c), the APT3Cooc4 (FIG. 4d), APT3Histo1 (FIG. 4e), 5 the APT3Histo2 (FIG. 4f), the APT3Histo4 (FIG. 4g), the APT3Histo5 (FIG. 4h), the APT3Histo9 (FIG. 4i) and the APT3Cooc7 (FIG. 4j).

FIG. 5a shows 2'-deoxyuridines and uridines modified at position 5. FIG. 5b shows 2'-deoxyadenines, adenines and guanosines modified at position 8. FIG. 5c shows 2'-modified uridines.

Figure 1:
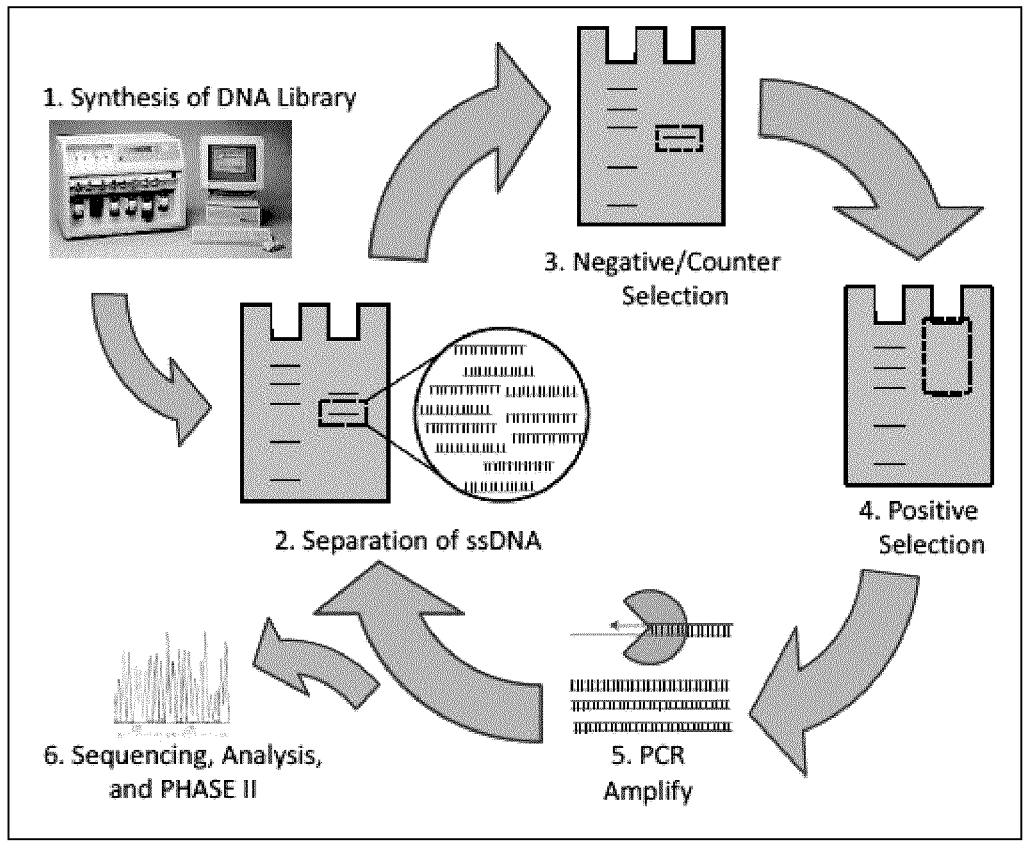
FIG. 1 is a schematic illustration of the aptamer selection strategy.

DESCRIP should prevent the adherence of the P97 and the P102 onto the epithelium cells. In other words, the therapeutic must neutralize both the P97 and the P102 binding sequences and their paralogs. To that end, two therapeutics can be used, one to neutralize the P97 and its paralogs, and one for P102 and its paralogs. As such the therapeutic medication is a combination of two neutralizing agents. According to another embodiment, a compound for diagnostic/detection binds to a recognizes the P97 and/or its paralogs.

P97 and its paralogs (Mh483, Mhp271, Mhp107), and Mhp683 (a paralog of P102) bind cilia and heparin. Also, GAGs sensitive to heparinase are found at the surface of porcine respiratory "cilia". From these observations it can be inferred the following hypothesis that (i) P97 binds directly to the cilia, and (ii) the paralogs of P97, as well as P102 and all its paralogs bind cilia during the early stages of colonization by targeting proteoglycans decorated with highly sulphated heparin-like GAGs. In other words, there are two primary "redundant" mechanisms to insure that binding onto the cilia of the pulmonary epithelium takes place. One pertains to direct and fast attachment to the cilia, while the second mechanism involves the attachment via binding to extra cellular matrix (ECM) components of the hosts (here the "hosts" are the cilia not the epithelium cell membrane per se). By binding to ECM proteins such as fibronectin, plasminogen[16], vitronectin, collagen, etc, the pathogenic microbes are able to mediate interactions with the host cells and, in many cases, increase their invasive capabilities. So far, the published data shows that there are two sub-mechanisms for binding via ECM complex; one triggered by a specific protease that cleaves the proteins at the S/T-X-F↓X-D/E sites, and another mechanism that involves another protease and another type of cleavage site (i.e. L-N-V↓A-V-S or ATNT↓NTNTGFS).

Note that the complete P97 surface protein amino acids sequence (SEQ ID NO:11) is[17].

$^{0001}$MSKKSKTFKIGLTAGIVGLGVFGLTVGLSSLAKYRSESPRKIANDF

AAKVSTLAFSPYAFETDSDYKIVKRWLVDSNNNIRNKEKVIDSFSFFTKN

GDQLEKINFQDPEYTKAKITFEILEIIPDDVNQNFKVKFQALQKLHNGDI

AKSDIYEQTVAFAKQSNLLVAEFNFSLKKITEKLNQQIENLSTKITNFAD

EKTSSQKDPSTLRAIDFQYDLNTARNPEDLDIKLANYFPVLKNLINRLNN

APENKLPNNLGNIFEFSFAKDSSTNQYVSIQNQIPSLFLKADLSQSAREI

LASPDEVQPVINILRLMKDNSSYFLNFEDFVNNLTLKNMQKEDLNAKGQN

LSAYEFLADIKSGFFPGDKRSSHTKAEISNLLNKKENIYDFGKYNGKFND

RLNSPNLEYSLDAASASLDKKDKSIVLIPYRLEIKDKFFADDLYPDTKDN

ILVKEGILKLTGFKKGSKIDLPNINQQIFKTEYLPFFEKGKEEQAKLDYG

NILNPYNTQLAKVEVEALFKGNKNQEIYQALDGNYAYEFGAFKSVLNSWT

GKIQHPEKADIQRFTRHLEQVKIGSNSVLNQPQTTKEQVISSLKSNNFFI

CNGHQVASYFQDLLTKDKLTILETLYDLAKKWGLETNRAQFPKGVFQYTK

DIFAEADKLKFLELKKKDPYNQIKEIHQLSFNILARNDVIKSDGFYGVLL

LPQSVKTELEGKNEAQIFEALKKYSLIENSAFKTTILDKNLLEGTDFKTF

GDFLAFFLKAAQFNNFAPWAKLDDNLQYSFEAIKKGETTKEGKREEVDKK

VKELDNKIKGILPQPPAKPEAAKPVAAKPETTKPVAAKPEAAKPEAAKPV

AAKPEAAKPVAAKPEAAKPVAAKEAAKPVAAKPEAAKPVATNTGFSLTNK

PKEDYFPMAFSYKLEYTDENKLSLKTPEINVFLELVHQSEYEEQEIIKEL

DKTVLNLQYQFQEVKVTSDQYQKLSHPMMTEGSSNQGKKSEGTPNGKKAE

GAPNQGKKAEGTPNQGKKAEGAPSQQSPTTELTNYLPDLGKKIDEIIKKQ

GKNWKTEVELIEDNIAGDAKLLYFILRDDSKSGDPKKSSLKVKITVKQSN

NNQEPESK$^{1108}$

This sequence includes both the endo- and the ecto-domains of the protein.

For therapeutic purposes the amino acid sequence for the F2$_{P97}$ segment of *Mycoplasma Hyopneumoniae* 232A (SEQ ID NO:12) is:

$^{768}$KLDDNLQYSFEAIKKG$^{784}$ETTKEGKREEVDKKVKELD

NKIKGILPQPP| AAKPE|AAKPV|AAKPE|TTKPV|AAKP

E|AAKPE|AAKPV|AAKPE|AAKPV|AAKPE|AAKPV|AA

KPE|AAKPV|AAKPE|AAKPV| ATNTGFSLTNKPKEDYFP

MAFSYKLEYTDENKLSLKTPEINVFLELVHQSEYEEQE

IIKELDKTVLNLQYQFQEVKVTSDQYQKLSHPMMTE|G

SSNQGKKSEGTPNQGKKAE|GAPNQGKKAEGTPNQGK

KAE| GAPSQQSPTTELTNYLPDLGKKIDEIIKKQ$^{1050}$GKN

WKTEVELIEDNIAGDAKLLYFILRDDSKSG$^{1082}$

Underlined are the R1 motifs; twice underlined are the R2 motifs. Note that F2$_{P97}$ of *Mycoplasma Hyopneumoniae* strain J is 301 amino acids long, while the F2$_{P97}$ of stain 232A is 314 amino acids long. This is because there are only 9 repeats in strain J while there are 15 repeats for strain 232A.

For detection purposes, published data suggests that only a subsection of F2$_{P97}$ can be used, in particular, the section that contains the R1 repeats sequences. Thus, the target section (SEQ ID NO:13) for the SELEX process is:

$^{768}$KLDDNLQYSFEAIKKGETTKEGKREEVDKKVKE$^{801}$LD

NKIKGILPQPP| AAKPE|AAKPV|AAKPE|TTKPV|AAKP

E|AAKPE|AAKPV|AAKPE|AAKPV|AAKPE|AAKPV|AA

KPE|AAKPV|AAKPEIAAKPV|ATNTGFSLTNKPKEDYFP

MAFSYKLE$^{914}$YTDENKLSLKT$^{925}$

The amino acids length of the target section thus varies from 113 to 157 amino acids, depending on the start (in italic-underlined) and finish (in bold black double-underlined) amino acids.

To produce critical segments of various surface proteins involved (or responsible) for binding onto cilia of pulmonary epithelium cells, detailed procedures are described[18]. The exact proteases responsible for the cleavage (i.e. the endoproteases processing of P97, P102, and their paralogs) of the surface proteins still remain unknown (see F. C. Minion,[11] for few possible proteases). The prevailing hypothesis is that a single protease is responsible for cleavage at all the S/T-X-F↓X-D/E sites while another protease is responsible for cleavage at all the other sites (see[13], A. T. Deutscher et al., *J. of Proteome Res.*, 2012, vol. 11, pp. 1924-1936), and a third one involves in the formation of complex ECM. While the three endoproteases that are operating in-vivo are not known, trypsin has been used with success in-vitro to induce cleavage of the P97 surface proteins[13, 19]. In all previous studies of *Mycoplasma Hyopneumoniae*, trypsin was added to cell suspensions at concentrations of trypsin of 0, 0.3, 0.5, 1, 3, 10, 50, and 300 µg/ml and incubated at 37° C. for 15 min. It is obvious that high concentrations of trypsin will digest the whole bacteria while the intent here is to cleave the surface protein as fast as possible (<1 min) for detection purposes. Thus, it is suggested to use ~1 µg/ml of trypsin but for one minute of exposure before entering the VDC. Nevertheless, the combination of [trypsin] and time of exposure at 37° C. needs to be optimized.

For detection purposes, it is also important to account for the fact that the binding of *Mycoplasma Hyopneumoniae* onto the porcine lung epithelium cilia is temperature dependent. This conclusion applies to both the direct binding of P97 to the cilia and to the indirect-binding via the ECM-GAGs complexes. Hence binding is maximal at 37° C., weak at 25° C. and minimal or in existent at 4° C.[20]. This stems from the fact that the biochemical reactions (i.e. the endoproteolytic processes) that are needed to cleave the various surface proteins are also T-dependent. This implies that *Mycoplasma Hyopneumoniae* can survive for long periods of time at low temperature (T≤20° C.), with the "uncleaved" surface proteins acting as camouflage (they mimic collagen and other typical lung tissue-forming molecules). When inhaled and exposed to the optimal temperature (i.e. T 37° C.), cleavage of the surface proteins (e.g. P97) takes place, follow by binding to cilia. From the point-of-view of detection, this implies that the "pre-activation" of the surface proteins (i.e. the cleavage of P97, P102, and their paralogs with trypsin) may be carried-out at 37° C. to increase the probability of detection.

As an alternative to the $F2_{p97}$ segment being 114 amino acids long, there may be few repeated amino acid sequences that pertain to the splitting of the P97, P102, and P146 surface proteins. Although different, there are similarities between these cleavage motifs. In fact, the identified cleavage motifs may have similar features such as "F or V" amino acid at the "right place", as well as first and second neighbours that lead to similar polarity (i.e. Isoelectric point, 3d-configuration, etc.). This stems from the fact that this sequence includes a short sequence (TTKF↓QE) that defines proteolytic cleavage in these surface proteins which control the binding of myco on the pilis of the pulmonary epithelium. For P97 there is a coiled-coil domain directly associated with the cleavage site at 195. If all the cleavage motifs have similar features (a given sequence preceded by a coiled-coil domain), they can thus be recognized by the available endoproteases (the endoproteases are needed to make the cleavage). This results in P50 (or F1, F2) segments that are very efficient in binding to cilia and heparan sulfate. It thus appears that the coiled-coil+short sequence associated with cleavage is the specific target for aptamer determination. In that case the aptamers need to bind to the cleavage sites before the cleavage process starts; thus preventing the formation of the P50 or F1, F2, etc segments that initiate direct binding and the formation of ecm-complex. The target for this case is LVAEFNFSLKKITEKLNQQIENLST<u>KITNF↓A</u>DEKTSSQKDPST
L The underlined segment corresponds to the coiled-coil domain while the twice underlined domain defines the cleavage site.

Recalling that pneumonia due to direct viral infection or due to secondary bacterial or viral invasion is the most frequent complication[21], and given the impact of *M. Hyopneumoniae* on the porcine industry, the challenge at present is to detect airborne *M. Hyopneumoniae* or to generate highly potent prophylactic tools that can be used to prevent *M. hyopneumoniae* infection in subjects that are at considerable risk of infection such as pregnant sows and young piglets. Unfortunately, measures to regulate the disease have been complicated by the pattern of persistent, subclinical infection with occasional epidemic outbreaks as well as the high heterogeneity of the virus and the failure of the antibody response to completely protect against re-infection and re-emergence[2-3].

The terms "sequence identity" or "% identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987).

One example of an algorithm that is suitable for determining percent sequence identity is the algorithm used in the basic local alignment search tool (hereinafter "BLAST"), see, e.g. Altschul et al., J Mol. Biol. 215: 403-410 (1990) and Altschul et al., Nucleic Acids Res., 15: 3389-3402 (1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al., Nucleic Acids Res., 32: W20-W25 (2004).

Detecting/Diagnosing *Mycoplasma hyopneumoniae*

The control of infectious disease is critically dependent on the availability of appropriate diagnostic tools. Several diagnostic methodologies are used to monitor *Mycoplasma Hyopneumoniae* infection. These include (i) following clinical signs and abattoir surveillance, (ii) the used of bacteriological cultures, (iii) serological detection such as ELISA, (iv) detection of *M. hyopneumoniae* antigen, (v) In situ hybridisation, (vii) and Polymerase Chain Reaction (PCR) methods[22]. As of today, the isolation of *M. Hyopneumoniae* from affected lungs by bacteriological culture is considered the "gold standard" diagnostic technique but isolation of the pathogen requires specialised Friis medium. When the detection of *M. hyopneumoniae* by culture is compared to the detection via immunofluorescence assay (IFA) or Enzyme-Linked Immuno-Sorbent Assay (ELISA), or by a polymerase chain reaction (PCR) method, bacteriological culture method is found the most sensitive technique particularly at the later stages of PEP when fewer *mycoplasma* organisms are present[23]. However, because the culture of *M. Hyopneumoniae* is laborious and time-consuming (isolation from field samples requires 4 to 8 weeks), several PCR techniques for *M. hyopneumoniae* DNA detection in different sample types have been developed (see table 2 in M. Sibila et al[22]). These PCR methods are more rapid than bacteriological culture and are relatively inexpensive to perform. However the confounding significance of sample contamination is much higher with PCR. Given that *M. hyopneumoniae* DNA from both live and dead organisms is amplified, the identification of PCR positive animals raises the question of whether such pigs have active infection or not.

Because *M. hyopneumoniae* attaches to the ciliated epithelium of the airways, the best samples to detect *M. hyopneumoniae* by PCR are tracheobronchial swabs or the bronchoalveolar lavage fluid (BALF). Interestingly, the use of PCR to detect *M. Hyopneumoniae* in lung tissue has produced variable results. Hence, for moderate to severe cases of PEP, the use of lung samples was found more appropriate than the use of BALF[24], while providing misleading information for mild cases of PEP[25].

Ideally, a test to detect the presence of a pathogen in a living animal should be easy to perform, rapid, inexpensive and should provide data of use in the implementation of control measures. Although the detection of *M. hyopneumoniae* in the nasal cavities of living pigs by PCR might theoretically fit these criteria, pigs inoculated with *M. Hyopneumoniae* intratracheally were found to have low numbers of organisms in their upper respiratory tract and only shed the organism intermittently[22-26]. However, the use of PCR to diagnose natural infection from nasal swabs was found reliable and an association was found between the detection of *M. hyopneumoniae* in the nasal cavities and bronchi with lesions of PEP. Although the potential use of nasal swabs for nested PCR (nPCR) testing for *M. hyopneumoniae* in live pigs has been demonstrated[25-26] the procedure is currently considered more useful for the monitoring of infection at a herd rather than at an individual animal level.

As an alternative to the current methodologies to detect viral and bacterial pathogens, the use of aptamers has been extensively implemented in last ten years. This is clearly reflected in the publication statistics. Since their discovery in 1990, there have been ~11,000 publications indexed to DNA or RNA aptamers in SciFinder, and more than 1,600 of these publications are patents[27]. Aptamers are specific oligonucleotides composed of single stranded DNA (ssDNA) or RNA that bind to a wide range of targets specifically. Aptamers can be obtained using an in vitro selection procedure called Systematic Evolution of Ligands by EXponential enrichment (SELEX), that starts with the incubation of random oligonucleotide libraries with the desired target molecules, followed by the separation and amplification of bound oligonucleotides[28]. By repeating this process, an enriched pool is obtained, which can be used as a starting library for the next round of selection to attain high specificity and affinity to the target molecules. FIG. 1 illustrates the continuous enrichment and selection of the binding aptamers to a given (specific) peptide sequence.

The production of aptamers is not costly, and they are very low in batch-to-batch variation compared to the antibodies produced in vivo. In addition, aptamers can be chemically synthesized, are thermally stable, and are suitable for long-term storage[29]. With these advantages, aptamers with high specificity and affinity have been developed for a variety of targets, including proteins, small molecules, whole cells, and viruses. Aptamers have now been widely used in diverse fields, such as diagnostics[30], therapeutics[31], and biosensors[32], as an alternative to antibodies.

Development of Therapeutics for *Mycoplasma Hyopneumoniae*

Several approaches have been undertaken to uncover novel therapeutics and vaccines against *M. hyopneumoniae*[1, 4-5, 8-9, 33]. Now, there are few killed-virus and modified-live vaccines (MLV) are on market[34]. Killed-virus vaccines are generally of limited efficacy at best[1, 35] while modified live *M. hyopneumoniae* vaccines (MLV) are the most effective option currently available for the control of the disease. Modified live *M. Hyopneumoniae* vaccines can confer solid protection against homologous reinfection and have significant effects in reducing viral shedding[1,8]. But the vaccine efficacy varies upon heterologous challenge. None of the current vaccines is able to completely prevent respiratory infection, transplacental transmission, as well as pig-to-pig transmission of the virus[1, 8, 33, 35-36]. Furthermore, the fact that the number of seropositive animals gradually increases towards the end of the fattening period in both vaccinated and non-vaccinated herds suggests that antibodies induced by either natural infection or vaccination do not prevent further infection[1, 4-5, 8-9, 35-36].

Since *M. hyopneumoniae* is an immunosuppressive disease, i.e. it confuses the immune defence system in the lung to stop it destroying them, it takes up to 4 weeks for the lesions to develop; they then consolidate for a further 4 weeks and then progressively heal from 10 weeks, as the pig's own immunity/resistance develops[9, 23, 37] (normally a respiratory infection such as the common cold, is cleared within 14 days). This immuno-suppression allows the secondary bacteria and other primary bacteria such as *Actinobacillus pleuropneumoniae*, to gain easier access to the lung and, accompanied by the virus damage also to the immune defences, can lead to the overwhelming infections.

Control of *Mycoplasma Hyopneumoniae* Infections

Optimizing management and housing conditions is primordial in the control of *M. Hyopneumoniae* infections and should be the first to be accomplished. Instituting management changes that reduce the possibilities of spreading *M. hyopneumoniae* or result in decreased lung damage by other pathogens do significantly improve the control of porcine enzootic pneumonia (PEP). Additional factors different from housing and management conditions, such as strain differences, may determine the infection pattern and clinical course of the disease. Overviews of control measures for *M. hyopneumoniae* infections related to environmental and management factors have been published by Maes et al.[13, 36].

To control and treat respiratory disease including *M. hyopneumoniae* infections in pigs, tetracyclines and macrolides are most frequently used. Also, other potentially active antimicrobials against *M. hyopneumoniae* include lincosamides, pleuromutilins, fluoroquinolones, florfenicol, aminoglycosides and aminocyclitols. Fluoroquinolones and aminoglycosides have mycoplasmacidal effects. Since the organism lacks a cell wall, it is insensitive to β-lactamic antibiotics such as penicillins and cephalosporins. Antimicrobial resistance of *M. hyopneumoniae* has been reported to tetracyclines, macrolides, lincosamides, and fluoroquinoles[7, 22, 40, 37]. This does not seem to constitute a major problem for treatment of *M. hyopneumoniae* infections to date[1, 22, 33].

While for most antimicrobials tested, the performance parameters are improved and lung lesions as well as clinical signs are decreased in treated animals, the treatment and control of enzootic pneumonia outbreaks is disappointing because the symptoms often reappear after cessation of the therapy. Pulse medication in which medication is provided intermittently during critical production stages of the pigs, can also be used. However, pulse medication during extended periods of time as well as continuous medication during one or more production stages is discouraged because of both the increased risk of spread of antimicrobial resistance and the possible risk for antimicrobial residues in the pig carcasses at slaughter[1, 22, 33].

Commercial vaccines, consisting of inactivated, adjuvanted whole-cell preparations, are widely applied worldwide[34]. The major advantages of vaccination include improvement of daily weight gain, feed conversion ratio and sometimes mortality rate. Additionally, shorter time to reach slaughter weight, reduced clinical signs, lung lesions, and lower treatment costs are observed[9, 22, 33]. Although protection against clinical pneumonia is often incomplete and vaccines do not prevent colonization, some studies indicate that the currently used vaccines may reduce the number of organisms in the respiratory tract[1, 22, 33, 38] and may decrease the infection level in a herd[22, 39]. On the other hand, transmission studies under experimental and field conditions[8, 38, 40] showed that vaccination against *M. hyopneumoniae* with the current commercial vaccines induced only a limited and non-significant reduction in the spread of *M. Hyopneumoniae*. Consequently, vaccination alone with the current vaccines is not sufficient to eliminate *M. hyopneumoniae* from infected pig herds. In the following sections we describe the development of novel anti-microbial therapeutics.

Preparation of Target for the SELEX Process

The nucleic acid molecules of the present disclosure are selected to specifically bind to molecules which participate in *M. hyopneumoniae* infection of a host organism. In some embodiments, the molecules are *M. hyopneumoniae* derived polypeptides. These *M. Hyopneumoniae* derived polypeptides may be various surface proteins or fragments thereof expressed by *M. hyopneumoniae* and which are used by *M. hyopneumoniae* to bind to the host organism's epithelium cilia. In other embodiments, the molecules are those expressed by the host organism which is the target of the *M. hyopneumoniae*.

In one aspect, the nucleic acid molecules of the present disclosure are generated to specifically bind to a polypeptidic complex comprising surface proteins expressed by *M. Hyopneumoniae* and/or molecules are those expressed by the host organism which is the target *M. hyopneumoniae*. To produce the "targeted binding site" that is needed for producing an aptamer by SELEX specific for a P97 surface protein, we first proceed with synthesizing the {768-1082} and the {768-925} segment of the P97 surface protein[17].

Hence, the optimal amino acids "binding sequence" of P97 protein (the ecto domain, SEQ ID NO:12) is:

$^{768}$KLDDNLQYSFEAIKKGETTKEGKREEVDKKVKELDNKIKGILPQPP| AAKPE| AA

KPV| AAKPE| TTKPV| AAKPE| AAKPE| AAKPV| AAKPE| AAICPV| AAKPE| AAKV| AA

KPE| AAKPV| AAKPE| AAKPV| ATNTGFSLTNKPKEDYFPMAFSYKLEYTDENKLSL

KTPEINVFLELVHQSEYEEQEIIKELDKTVLNLQYQFQEVKVTSDQYQKLSHPMMT

E| GSSNQGKKSEGTPNQGKKAE| GAPNQGKKAEGTPNQGKKAE| GAPSQQSPTTEL

TNYLPDLGKKIDEIIKKQGKNWKTEVELIEDNIAGDAKLLYFILRDDSKSG$^{1082}$ while the minimal domain ("binding sequence", SEQ ID NO:13) for diagnostic purposes is $^{768}$KLDDNLQYSFEAIKKGETTKEGKREEVDKKVKELDNKIKGILPQPP| AAKPE| AA
KPV| AAKPE| TTKPV| AAKPE| AAKPE| AAKPV| AAKPE| AAKPV| AAKPE| AAKPV| AA
KPE| AAKP| AAKPE| AAKPV| ATNTGFSLTNKPKEDYFPMAFSYKLEYTDENKLSLKT$^{925}$ Various technologies are currently available to produce these two peptides. The procedure that was used to produce P97 and N97 is described below.

First, the DNA sequence encoding 315 amino acid (aa) sequence of P97 was synthesized and cloned into a regular cloning vector. The DNA sequence encoding MHHHHHH (SEQ ID NO: 20) was added before K768 at the 5'. The sequence had 322×3=966 bp ORF plus two STOP codons at the end plus 5' and 3' cloning sites (total=984 bp), and was confirmed by sequencing. The ~984 bp fragment was cloned into an *E-Coli* expression vector. The N-terminal 157 aa (plus MHHHHHH plus STOPs plus cloning sites) was PCR amplified and cloned into *E. coli* expression vector to obtain the second expression plasmid. Both plasmids were confirmed by sequencing (the sequence has many repeats and this made it difficult to synthesize and make expression plasmids).

Then the expression was optimized by introducing into *E. coli* and by trying many different conditions.

Since the proteins were partially insoluble, they were purified under denaturing conditions (1 L culture each) and were refolded.

The following genes were cloned into pET expression vectors. The sequence was confirmed by sequencing the genes, and was introduced into the *E. Coli* expression host BL21. We analyzed several colonies for expression at 18° C. and 37° C. by SDS-PAGE and Western with anti-His antibody. The results are summarized below.

Approximately 40% of the His-P97 protein (323aa (His tag and 316aa)=35.47 kDa, pI 8.56) is soluble at 18° C. with high expression levels.

The His-NP97 protein (165aa (His tag and N-terminal 158aa)=17.82 kDa, pI 9.76) is soluble at 18° C. with high expression levels.

The His-R97 protein (His-R97, 323aa (His-tag and randomized P97 control)=35.44 kDa, pI 8.50) is soluble both at 18° C. and 37° C. but with very low expression levels.

The His-RBP protein (257aa (His-tag and mouse RBP control)=26.40 kDa, pI 9.95) showed no expression both at 18° C. and 37° C.

The His-GFP protein (245aa (His-tag and GFP control)=27.76 kDa, pI 5.99) is soluble both at 18° C. and 37° C. with high expression levels.

Approximately 50% of the experimental control GST-His protein (256 aa=29.79 kDa, pI 7.19) is soluble at 18° with high expression levels.

Afterward, large scaled cultures of His-P97, His-NP97, His-GFP, and His-RP97 were grown and purified.

Determination of the ssDNA Aptamers for *M. hyopneumoniae*

Using the $P97_{\{768-1082\}}$ and the $P97_{\{768-925\}}$ peptides, the corresponding binding aptamers were identified using the SELEX procedure. FIG. 1 shows the overall procedures that were used to identify the aptamers for the targeted peptides.

Figure 2:
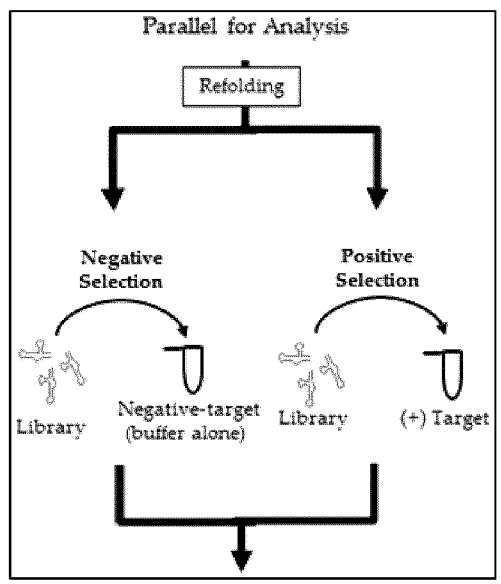
FIG. 2 is a schematic drawing showing parallel assessment of an enriched aptamer library.

Electrophoretic Mobility Shift Assays (EMSAs) were used to separate portions of the aptamer library that bind to a given target (NP97) and fail to bind to a counter target (RP97) in a buffer consisting of 1×DPBS (26.67 mM KCl, 14.71 mM $KH_2PO_4$, 1.38 M NaCl, and 80.60 mM $Na_2HPO_4$-$7H_2O$) with 10 mM $MgCl_2$ (pH 7.4). One round of selection consisted of enriching for unbound, non-shifted DNA material in the presence of the counter target followed by the isolation of bound and shifted DNA after exposure to the target molecule. Each selection round was followed by library amplification through PCR and purification of the DNA Sense strand. After subjecting the initial library of diverse random sequences to three consecutive rounds of selection, the enriched library was divided into two fractions to perform the parallel assessment as shown in FIG. 2.

Aptamers enriched after three rounds of positive and negative selections are subjected to a parallel assessment, which involves simultaneously exposing half of the enriched library of aptamer to the target and the other half of the library to the counter target. The parallel assessment is designed to identify DNA molecules that bind indiscriminately to both target and counter target molecules. These promiscuous aptamers were discarded during the bioinformatics analysis portion of the project.

After parallel assessment PAGE purifications of bound libraries were performed, 15 pmoles of enriched library was exposed separately to either the target (NP97) or counter target (RP97) in selection buffer. After a 60-minute incubation at 37° C., bound DNA material was separated from unbound material using 10% non-denaturing PAGE.

Figure 3:
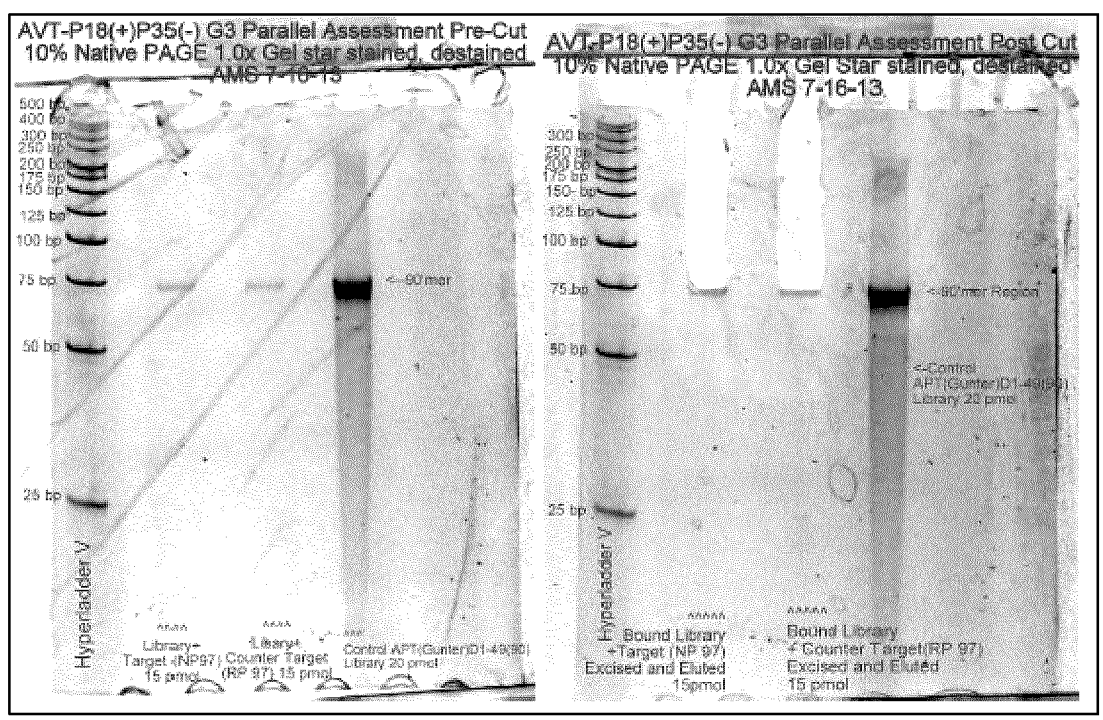
FIG. 3 is a gel electrophoresis showing typical results from the PAGE purification process of bound libraries.

Presumably bound material was excised, eluted from the gel, and used as template in PCR amplification in preparation for sequencing. Gel images were taken before and after excision. Hyperladder V (Bioline; Randolph, Mass.) was used as a molecular weight standard. The gels were stained with GelStar Nucleic Acid Stain (Lonza; Walkersville, Md.). Typical results are shown in FIG. 3.

Predicted secondary structures (top panels) and sequence data (bottom panels) are displayed in FIG. 4 for the five of the ten most promising aptamer candidates. The first four candidates (FIGS. 4a to 4d) and the last candidate (FIG. 4j) were determined using motif analysis, while the remaining five (FIGS. 4e to 4i) were determined on the basis on sequence frequency in the candidate library dataset. The secondary structure and free energy for each aptamer was computed with Quickkfold 3.0 (OM. Zuker, MFold web server for nucleic acid folding and hybridization prediction. Nucleic Acid Research, 2003, vol. 31, pp. 3406-3415). Sequences displayed below each structure were identified using proprietary algorithms of Aptagen. The underlined region in each sequence is the PCR prime annealing region.

The initial library containing a large number of random sequences was subjected to three rounds of polyacrylamide gel-based SELEX. The SELEX process is designed to enrich for sequences that bind to the target molecule and eliminate sequences that bind to the counter target molecule over multiple rounds of selection (FIG. 1). As a result, the population to be sequenced is expected to contain multiple copies of potential aptamer candidates; largely homologous sequences representing a library of aptamer candidates[41]. The selection strategy employed in the present project was designed to identify aptamers that bind to NP97, what has been determine to be a region of protein vital for the pathogenicity of *M. hyopneumoniae*, but fail to bind to RP97, a randomized version of that same region. Three rounds of positive and negative selections were conducted. The resultant enriched library was PCR amplified and then divided into two samples, with one exposed to the target in binding buffer and the other exposed to the counter-target (negative-target) in binding buffer (FIG. 2). After partitioning through non-denaturing polyacrylamide gel electrophoresis (non-denaturing PAGE), the regions of gel containing presumably bound material were excised for nucleic acid elution (FIG. 3). DNA collected from the elution was PCR amplified in preparation for sequencing.

Illumina-based technology was implemented to sequence the aptamers after the selections. Subsequent bioinformatics analysis of the sequencing data identified candidate aptamer molecules. Deep sequencing and subsequent data analysis eliminated the traditional approach of performing a large number of selections, which may introduce error and bias due to the screening process.

A "good sequence" was assessed as one that contained the full forward and reverse primers (or their complements), as well as a variable region between 44 and 54 nucleotides long to account for minor insertions or deletions of bases. The data was analyzed using proprietary algorithms to identify candidate sequences.

For the aptamer candidate selection the analysis ranked sequences according to a variety of categories, including frequency of homologous sequences, frequency based on motif presence, and presence of multiple motifs. A motif is a smaller segment of bases conserved between sequences, most likely because the segment contributes to the aptamer's binding ability. For the selection of ten candidate sequences to test, the presence of multiple motifs in a sequence was weighted more heavily than the frequency of homologous sequences. However, the relative complexity of a candidate's secondary structure weighed heavily in its ranking. This was primarily determined by the number of stems on the predicted secondary structure (as described below) that are coming-out of the central junction. Thus, while APT3Cooc7 (FIG. 4.j) was determined through the co-occurrence method[41], the fact that there is only 1 stem coming from the central junction makes it one of the less likely candidates. Despite this, there is no large difference in the rankings of the candidates, and they are all worth examining for further characterization.

In addition to sequence and motif analysis, secondary structure prediction of the candidate sequences was carried out using the Mfold Web Server (OM. Zuker, MFold web server for nucleic acid folding and hybridization prediction. Nucleic Acid Research, 2003, vol. 31, pp. 3406-3415). By inputting the full sequence as well as folding temperature and salt conditions, it is possible to make an informed prediction about what structures an aptamer candidate may take (FIG. 4). The parameters used for the analysis of the selected sequences were matched as closely to selection parameters as possible (e.g. 1.5 M NaCl, 0.01 M $MgCl_2$).

The selected aptamer candidates were then synthesized using phosphoramidite chemistry, and used for affinity binding studies and $K_d$ measurements.

From FIG. 4 the ten (10) aptamers corresponding to the P97 peptidic complex targets of *M. hyopneumoniae* are:

```
APT3Cooc10 (SEQ ID NO: 1):
5'-GCC-TGT-TGT-GAG-CCT-CCT-AAC-GGG-TAT-GAC-TAC-AGA-TGC-AGG-
GCG-GCC-TGT-AGC-CTT-GCA-TTG-ACA-AGG-GCA-TGC-TTA-TTC-TTG-TCT-
CCC-3'

APT3Cooc2 (SEQ ID NO: 3):
5'-GCC-TGT-TGT-GAG-CCT-CCT-AAC-GCG-AGT-CCC-AAT-CTG-GAG-GGG-
AGC-GAG-AGG-CAA-GTA-TGG-TTG-CCG-GGA-GCA-TGC-TTA-TTC-TTG-TCT-
CCC-3'

APT3Cooc3 (SEQ ID NO: 5):
5'-GCC-TGT-TGT-GAG-CCT-CCT-AAC-TAG-CTC-GTA-GAA-AAA-AAA-TAT-
AGC-GTG-TGC-TGG-GAC-TGC-TCG-GGA-TTG-CGG-ACA-CAT-GCT-TAT-TCT-
TGT-CTC-CC-3'

APT3Cooc4 (SEQ ID NO: 2):
5'-GCC-TGT-TGT-GAG-CCT-CCT-AAC-AGT-GAT-GAA-GGG-ATC-ACG-GGC-AAA-
GGA-CCG-TGA-CAA-ATC-ACG-GAG-TGT-CAT-GCT-TAT-TCT-TGT-CTC-CC-3'

APT3Histo1 (SEQ ID NO: 4):
5'-GCC-TGT-TGT-GAG-CCT-CCT-AAC-CGC-ACG-TGG-GTA-TTC-TAA-GTG-
CGG-TAG-CTC-AAT-GGT-GAG-CGA-TGA-GCA-TCA-TGC-TTA-TTC-TTG-TCT-
CCC-3'

APT3Histo2 (SEQ ID NO: 6):
5'-GCC-TGT-TGT-GAG-CCT-CCT-AAC-GAA-AGT-TAC-AGG-CTG-CGC-GGA-
GAG-GAG-CCC-AAG-CGA-GCT-TTG-CTG-ATG-CCA-TGC-TTA-TTC-TTG-TCT-
CCC-3'

APT3Histo4 (SEQ ID NO: 7):
5'-GCC-TGT-TGT-GAG-CCT-CCT-AAC-ATA-GCA-CAT-TTG-ATG-AGG-AGG-
CCT-TGA-TTA-AAG-GCC-GGC-TTG-TGA-ACG-TCA-TGC-TTA-TTC-TTG-TCT-
CCC-3'

APT3Histo5 (SEQ ID NO: 8):
5'-GCC-TGT-TGT-GAG-CCT-CCT-AAC-GAC-GAT-GGA-GCG-GCC-CCA-AGT-
CGC-TCT-TGC-ATG-TTA-ATG-GAT-CGC-CAC-ATC-ATG-CTT-ATT-CTT-GTC-
TCC-C-3'

APT3Histo9 (SEQ ID NO: 9):
5'-GCC-TGT-TGT-GAG-CCT-CCT-AAC-GTT-GCC-GCT-TAG-TGG-GCG-GCA-
TCA-CTC-GAT-TGA-AAC-GAT-TAG-TGT-AGT-ACA-TGC-TTA-TTC-TTG-TCT-
CCC-3'

APT3Cooc7 (SEQ ID NO: 10):
5'-GCC-TGT-TGT-GAG-CCT-CCT-AAC-ACC-ACG-GGC-CTG-GGG-CAT-TTA-
TAG-CAT-AGG-CGC-GTG-GCA-ACC-TAC-GTA-CCA-TGC-TTA-TTC-TTG-TCT-
CCC-3'
```

Using the most appropriate cilia binding procedure these aptamers have been "screened" to identify the ones having the highest and fastest binding capabilities for detection and therapeutics purposes. Hence, we used a tissue culture system[42] to study the binding of our aptamers onto the ciliary epithelial. The differentiated epithelial cell model that was used has distinct advantages for the study of the interactions between M. Hyopneumoniae, the aptamers, and the tracheal epithelial cells. This is because the morphology of the cultured cells shares many of the features found on the intact epithelium. Most prominent feature of the culture system is the presence of tight junctions and the differentiation of the apical and basolateral cell membranes. The apical membrane contained cilia and microvilli while the basolateral membrane is showing interdigitations. The presence of mitochondria, endoplasmic reticulum, secretory granules, and basal bodies of cilia are similar to that observed in intact epithelium. The cells grown with the air interface as described here differentiated as demonstrated by the formation of cilia. Under the culture conditions described, approximately 10 to 50% of the cells are covered by cilia in contrast to normal swine epithelium, which has at least 70% of the surface cells ciliated[43].

Preparation of Cilia Model

Previous work has provided information relative to the attachment of M. hyopneumoniae to and effect on, the cilia in several different swine cell systems. These systems have included single ciliated cells from swine tracheas[43], newborn piglet tracheal organ cultures[44] and a microtiter plate adherence assay using purified swine tracheal cilia (Zhang,[20]). None of these systems allowed close simulation of the epithelial cell/mycoplasma relationship that is thought to be such a dynamic aspect of the infection in the living pig[45]. This is why we used a tissue culture system consisting of confluent monolayers of tracheal epithelial cells on microporous membranes. The cells retain most of the morphologic characteristics of intact tracheobronchial epithelium including apical microvilli and cilia, apical tight junctions, moderately interdigitated lateral intercellular space and mucin secretion Epithelial cells were isolated from the tracheas of twelve-weeks old SPF pigs (SIV, PRRSV, and M. hyopneumoniae-free). The pigs were euthanized by percussion followed by exsanguination. The tracheas were aseptically removed and rinsed in cold sterile phosphate buffered saline solution, pH 7.2 (PBS) to remove mucus and debris. All muscle tissues were trimmed off the tracheas, which were then placed in 50 ml polypropylene tubes containing sterile 0.15% pronase and 0.01% DNAse in $Ca^{2+}$- and $Mg^{2+}$-free minimum essential medium (MEM) and incubated at 4° C. for 24 h. The enzymes were inactivated after 24 h with the addition of foetal bovine serum (FBS) to a final concentration of 10%.

The tubes were inverted several times to loosen cells from the tracheas, and cells were pelleted by centrifugation at 125 g for 5 min. The pelleted cells were re-suspended in a mixture of Dulbecco's MEM (high glucose) (DMEM) and Ham's F-12 (1:1) containing 5% FBS, 0.12 U/ml insulin, and 100 U/ml of penicillin-streptomycin. Cell suspensions were transferred to tissue culture dishes and incubated in 5% $CO_2$ for at least 1 h to remove fibroblasts. The non-attached epithelial cells were then collected. A portion of the cell suspension was diluted in 0.04% trypan blue for counting and assessing viability.

Millicell-PCF inserts (0.45 μm pore size, 0.6 $cm^2$ area, Millipore, Bedford, Mass., USA) were coated with human placental collagen (HPC; Type IV, Sigma) and placed in 24-well culture plates. A stock solution of 0.05% HPC in 0.2% glacial acetic acid was prepared. Each Millicell-PCF insert was coated with 200 μl of a 1:10 dilution of the stock HPC solution and incubated overnight at room temperature. On the day the tracheal cells were added to the inserts, the collagen was removed and the inserts air-dried. The inserts were then washed once with PBS and once with medium to remove any residual collagen.

The tracheal cells were plated at a concentration of 3.75-5×$10^5$ cells/$cm^2$ onto the prepared Millicell-PCF inserts and grown on the air-liquid interface[20, 46]. To create an air-liquid interface feeding system, the apical side of the membrane containing the tracheal epithelial cells was left exposed to the air. The cells were nourished from underneath with serum-free DMEM/F-12 (1:1) containing 2% ultroser G serum substitute (USG medium) supplemented with penicillin and streptomycin.

Mucin secreted by the cell cultures was measured by a mucin dot blot assay while cell secretions were collected by washing the surface of cultures with 200 μl of PBS. 2 μl of the cell secretions in PBS, along with various concentrations of mucin as controls, were pipetted onto nitrocellulose membrane sheets. The membrane sheets were soaked in tris(hydroxymethyl)aminomethane (THAM)-saline-polyoxyethylene sorbitan/Tween 20 (TST) for 30 min and incubated with diluted rabbit serum produced against porcine mucin type III from porcine stomach (Sigma, St. Louis, Mo., USA) at room temperature for 1 hour. The sheets were then reacted with goat anti-rabbit horseradish peroxidase conjugate for 1 h at room temperature. After washing with TST, color was developed with the addition of $H_2O_2$ and 4-chloro-1-naphthol. The intensity of color was used to estimate the quantity of mucin. The image of the dots was captured using a Molecular Device flatbed scanner (model Emax). Intensity of each dot on the sheet was analyzed using the NIH image analysis software (see http://rsb.info.nih.gov/nih-image/).

Procedure for Binding Tests

All strains of M. hyopneumoniae were prepared from stock cultures inoculated into Friis medium at a 1:10 dilution followed by incubation at 36° C. in a shaking water bath. Cells were harvested when culture pH was lowered to approximately 6.8 after 1-2 days' incubation. Cells were washed once in PBS or Friis medium with no antibiotics and re-suspended at $\frac{1}{20}$ of the original culture volume in PBS or Friis medium. The organisms were then passed three times through a 25-gauge needle to disperse aggregates. The M. Hyopneumoniae suspensions were used for the adherence study.

50 μl (5×$10^8$–1×$10^9$) of M. hyopneumoniae 232 was added to duplicate inserts containing the differentiated tracheal cell cultures after 12-22 days of growth. The cells were then incubated at 37° C., 5.2% $CO_2$, for either 90 min or 2 days. After incubation, the inserts were gently washed three times with PBS to remove the unattached mycoplasmas.

Cell numbers on the inserts were determined as described by Clark et al.[47] Briefly, tracheal cells were released from the collagen-coated membranes by incubation in a solution of 0.05% trypsin-0.53 mM EDTA at 37° C. for 10 min. The solution was added to the top and bottom compartments. At the end of incubation, the trypsin-EDTA solution was carefully removed without dislodging the cell layer. 100 μl of PBS was then added to the insert and pipetted up and down extensively to dislodge and disperse the cells. After removing the cell suspension, membranes were washed with another 100 μl of PBS that was later pooled with the cell suspension. A portion of the pooled cell suspension was then stained by trypan blue for counting in a haemocytometer.

Note that with the procedure that was used the confluent monolayers of pseudo-stratified epithelium containing morphologically identifiable ciliated, secretory and basal cells were formed on HPC-coated Millicell membrane inserts. The cells began to differentiate 4-5 days after plating at a density of $3.5\text{-}5\times10^5$ cells/cm² (approximately $3\times10^5$ per insert) and culturing in serum replacement medium with air-liquid interface feeding. Also, the ciliated cells are distributed throughout the inserts. The majority of the cells have microvilli covering the surface of the cultured cells. The cilia on the inserts in the cultures were healthy after 22 days in culture. The percentage of ciliated cells on the inserts varied between 10 and 50%. The number of viable epithelial cells is in the range of $6.8\times10^5$ (15 days post plating) and $5\times10^5$ (23 days post plating) per insert.

In PBS, *M. hyopneumoniae* strain 232 are attached to the cilia, inducing tangling, clumping and longitudinal splitting within 90 min of the addition of mycoplasmas to the cells. Cilia remained damaged 2 days after *M. hyopneumoniae* infection even if no organisms are present. In Friis medium, cilia were bundled together and large numbers of *M. hyopneumoniae* are found predominately to adhere to the top of the cilia at 90 min and 2 days post infection. No damage to cilia was observed at either 90 min or 2 days post infection with the 232 strain.

In PBS and with the proper (sufficient) concentrations of the binding aptamers, *M. Hyopneumoniae* 232 did not attach to cilia and the cilia remained undamaged even after 22 days. In fact, after screening is was found that APT3Cooc10, APT3Histo1, and APT3Cooc3 have the highest binding capabilities from a biosensing and therapeutic perspectives.

While reducing the present invention to practice, the present inventors have uncovered that oligonucleotides (e.g., aptamers) designed to bind conserved sequences in the P97 polypeptidic complex can be utilized to prevent binding to the cilia of the pulmonary epithelium cells. As is illustrated in the examples section that follows, the present inventors, have provided, aptamer nucleic acid molecules, which can be used to diagnose and treat *M. hyopneumoniae* infection. Such aptamer molecules exhibit viral cross-reactivity and as such can be used as therapeutics and/or vaccines against the *M. Hyopneumoniae*.

Assessing the Binding Capabilities of the Selected Aptamers

Aptamers are nucleic acid sequences of tertiary structures, which are selected to specifically bind a polypeptide of interest and inhibit a specified function thereof. Detailed description of aptamers and mechanism of action thereof is provided by Wilson & Szostak, and others[28]. Thus, according to one aspect of the present invention there is provided a nucleic acid molecule including a polynucleotide sequence that is capable of specifically binding a polypeptidic complex participating in the *M. hyopneumoniae* infection of cells.

The ability of the nucleic acid molecules of this aspect of the present invention to specifically bind a polypeptidic complex that participates in the *M. hyopneumoniae* infection of cells allows the use thereof in *M. hyopneumoniae* infection therapy and diagnostics.

As used herein "a polypeptide which participates in *M. hyopneumoniae* infection of cells" refers to a polypeptide that is encoded by various virulent *M. hyopneumoniae* strains, a host cell polypeptide or a peptide fragment thereof.

Examples of *M. hyopneumoniae* polypeptides that participate in infection of pulmonary epithelium cells include $P97_{\{768\text{-}1082\}}$, $P97_{\{768\text{-}1050\}}$, $P97_{\{768\text{-}925\}}$, $P116_{\{700\text{-}1010\}}$, $P102_{\{1\text{-}324\}}$, and $P102_{\{1\text{-}529\}}$. It is important to emphasize that all these peptides carry the repetitive motifl AAKPE| AAKPV| AAKPE| TTKPV| (or a motif being more than 80% similar).

Examples of host cell polypeptides that participate in *M. hyopneumoniae* infection include but are not limited to P97, P102, P116, P146, P216, and P159 It will be appreciated that polypeptide targets of this aspect of the present invention are preferably microbial, to maximize specificity of the nucleic acid molecules of the present invention and reduce cytotoxicity thereof. Accordingly, preferred polypeptide target sequences include if nucleic acid molecules generated to bind such sequences can be used as universal *M. hyopneumoniae* vaccines.

Few examples of conserved microbial peptide targets for *M. hyopneumoniae* are provided in the following Table 1.

TABLE 1

| Microbial peptide targets of M. Hyopneumoniae <SEQ ID NO:> | Peptide sequence | Identifier | Ref. |
|---|---|---|---|
| P97 <12> | ⁷⁶⁸KLDDNLQYSFEAIKKG⁷⁸⁴ETTKEGKREEVDKKVKE LDNKIKGILPQPP\| AAKPE\|AAKPV\|AAKPE\|TTKPV\| AAKPE\|AAKPE\|AAKPV\|AAKPE\|AAKPV\|AAKPE\|A AKPV\|AAKPE\|AAKPV\|AAKPE\|AAKPV\| ATNTGFSLT NKPKEDYFPMAFSYKLEYTDENKLSLKTPEINVFLE LVHQSEYEEQEIIKELDKTVLNLQYQFQEVKVTSDQ YQKLSHPMMTE\| GSSNQGKKSEGTPNQGKKAE\|GA PNOGKKAEGTPNQGKKAE\| GAPSQQSPTTELTNYL PDLGKKIDEIIKKQ¹⁰⁵⁰GKNWKTEVELIEDNIAGDAK LLYFILRDDSKSG¹⁰⁸² | AAB47806.1 and MHP0198 MHP183 | [17] |
| P102 <15> | ⁶⁸³EDNPEGDWITLGRMEKLVKEVIQYKKEGTKTFLD DEVAKTLYYLDFHHLPQSKKDLEEYKEKHKNKFIN EKPATATSQAKPDQAKNEKEVKPESAQAESSSSNSN DSNSKTTSSSSMAGTTQNKSTBETPNSSSNSTPTSSA TTSTTSSTQAAATSASSAKVKTTKFQEQEKQQVKEQ KQKQEKTKETNQLLDTKTNKENLGGLILWDFLVNS KYKTLPGTTWDELVEPDSENDRLKITAILKENTSQA KSNPDSKNLTSLTRNLIIKGVMANKYIDYLVQEDPV | MHP0182 | L. Seymour et al, 2012[16] |

TABLE 1-continued

Microbial peptide targets of *M. Hyopneumoniae*

| <SEQ ID NO:> | Peptide sequence | Identifier | Ref. |
|---|---|---|---|
| | LLVDYTRRNQIKTEREGQLIWSQLASPQMASPEPEK TKLEITEEGLRVKKGGTKIKEGIKNGSSRGNTNTNS KPNKKLVLLKGAIKNPGTKKEWILVGSGIKDNNNG GSNNNSNTQIWITRLGTSVGSLKTEGETVLGISNNN SQEVLWTTIKSKLENENPSDNNQIQYSPSTHSLTTNS RSNTQQSGRNQIKITNTQRKTTTSPSQNLSQNPDPN QIDVRLGLLVQDKKLHLWWIANDSSDEPEHITIDFA EGTFNYDDLNYVGGLLKNTTNNNNTQAQDDEGDGY LALKGLGIYEEPDDESIDQAATVEKAERLYKHFMG LFRE$^{1201}$ | | |
| P116 <16> | $^{651}$QLTQEGFKLTNPIKFQQNQSKTKENIARTVNISYL AFKPKNINDYKKHYLLADSDGNGLFIQKIKNTEKTT QNSDITFIKPENLDQKNKDETQQKQVDGSYLYQNK KSLYSLANLFPPELIDKQAVILGPNSLAIVELANRIG ENRFYRQELRNSSPFSLEKSKESVEISAFSSSNYQLN SKTSLNLNGKTIYNINPVIGPNPKKTTDKNGSNNEKI NKNSSIILKGIAVYRNAFIKAYIK$^{1010}$ | MHP0108 | L. Seymour et al, 2010[13] |
| P146 <17> | $^{504}$STKIGIDLGVLKKYISNNQGIEYTEDIANAKIRDAQ GDGITSHIEIPVTISLWSSFFGDSDNVLLKSKTETFII PYFQKETTSESKDQKVGHTQKELDLNQKLVYQLSE LPGTSTQGSSGSSTQTEQIKEVKLPTLTAFISKQELE ALIDGDKNLASQPTSQAVSVSQVKATEFQQQDANST NSSPTSPSPSPTSPSPASPSSSPSPTSPKNLDENIGVP NPRFEEIKKIISSEFTYKYNFRANEALLDAWVGKQN FPSLKDISQFRSDQRLAKDYKLVNLKSNKFLEDYDV LAFYANLVQKDPREVLQYLFEIARANNLIGPEEKLD LNQIEEDGIFRRAKAIKLIDKSSNNQGIYGESENNQF LKFHERGWMSTLYLPNEAKTKLADYQNLLSAGISD TKIFSELNKIQPLDLNIKTQSSDSSDKSDSSDSDDAK TTSTKQDLLKLTSLKSQIEAIVKKYETESKKYLG$^{1025}$ | MHP0663 and MHP684 | D. Bogema et al., 2012[13] |
| P216 <18> | $^{903}$SGAKSTIIFEEIAELDPKVKEKVGADVYQLKEHYA IGFDDNAGKENQEVIRSSSRTIYLKTSGKSKLEADTI DQLNQAVKNAPLGLQSFYLDTERFGVFQKLATSLA VQHKQKEKTLPKKLNNDGYTLIHDKLKKPVIPQISS SPEKDWEEGKLNQNGQSQNVNVSTEGSIIESPYFST NFQEDADLDQDGQDDSRQGNNSLDNQEAGLLKKLA ILLGNQFIQYYQQNDKEIEFEIINVEKVSELSFRVEF KLAKTLEDNGKTIRVLSDETMSLIVNTTIEKTPEMS AVPEVEDTKWVEQYDPRTPLAAKTKEVLKEKDQIP VDGSGNISDKWLASIPLVIHQQMLRLSPVVKTIREL GLKTEQQQQQQQQQQQQQPQKKAVRKEEELETYN PKDEFNILNPLTKAHRLTLSNLVNNDPNYKIEDLKV IKNEAGDHQLAFSLRANNIKRLMNTPITFADYNPFF YYNEDWRSIDKYLNNKGNVSSHQQQAAGGNQGSGL IQRLNKNIKPETFTPALIALKRDNNTNLSNYSDKIIM IKPKYLVERS$^{1444}$ | MHP0496 and MHP493 | J. Wilton et al.[13] |

The nucleic acid molecules of this aspect of the present invention refer to single stranded or double stranded DNA or any modifications thereof, which are capable of specifically binding the polypeptide-targets described hereinabove. The nucleic acid molecules of this aspect of the present invention are interchangeably referred to as "aptamers".

Typically, the nucleic acid molecules according to this aspect of the present are of varying length, such as 10-100 bases. It will be appreciated, though, that short nucleic acid molecules (e.g., 10-40 bases) are preferably used for economical, manufacturing and therapeutic considerations, such as bioavailability (i.e., resistance to degradation and increased cellular uptake).

According to embodiments of this aspect of the present invention, the nucleic acid molecules are preferably those set forth in APT3Cooc10, APT3Histo1 and APT3CooSeq3.

Modification of Nucleic Acid Sequences

As mentioned hereinabove, the nucleic acid molecules of this aspect of the present invention are preferably modified to obtain enhanced bioavailability and improved efficacy to the target polypeptide. Modifications include but are not limited to chemical groups that incorporate additional charge, polarizability, hydrogen bonding, electrostatic interaction and fluxionality to the nucleic acid bases or to the entire molecule. Added or modified chemical groups are selected to include conformationally flexible linkages, which conform to the topology of the polypeptide target. Additionally, measures are taken that the chemistry for the modification of the nucleic acid molecules of this aspect of the present invention allows for either trisphosphate (NTP) or phosphoramidite synthesis.

Thus, for example, nucleic acid molecules of this aspect of the present invention preferably include modifications that allow specific cross-linking to the target polypeptide to thereby form high affinity compounds.

Appended cross-linking groups can contain hydrophobic, hydrophilic or charged functionality. Cross-linking may be accomplished by the formation of imine, acetal, ester and disulfide linkages as well as by conjugate addition to α, β-unsaturated carbonyl linkers. Examples of 3'-deoxyuridine nucleosides which are suitable for phosphoramidite synthesis are shown in FIG. 5a including small hydrophobic functional groups such as vinyl (group 1, FIG. 5a), large hydrophobic functional groups such as pyrenyl (groups 13-14, FIG. 5a) and carbonyl compounds with varying degrees of side chain hydrophobicity (groups 3, 6-11, FIG. 5a).

Figure 5:
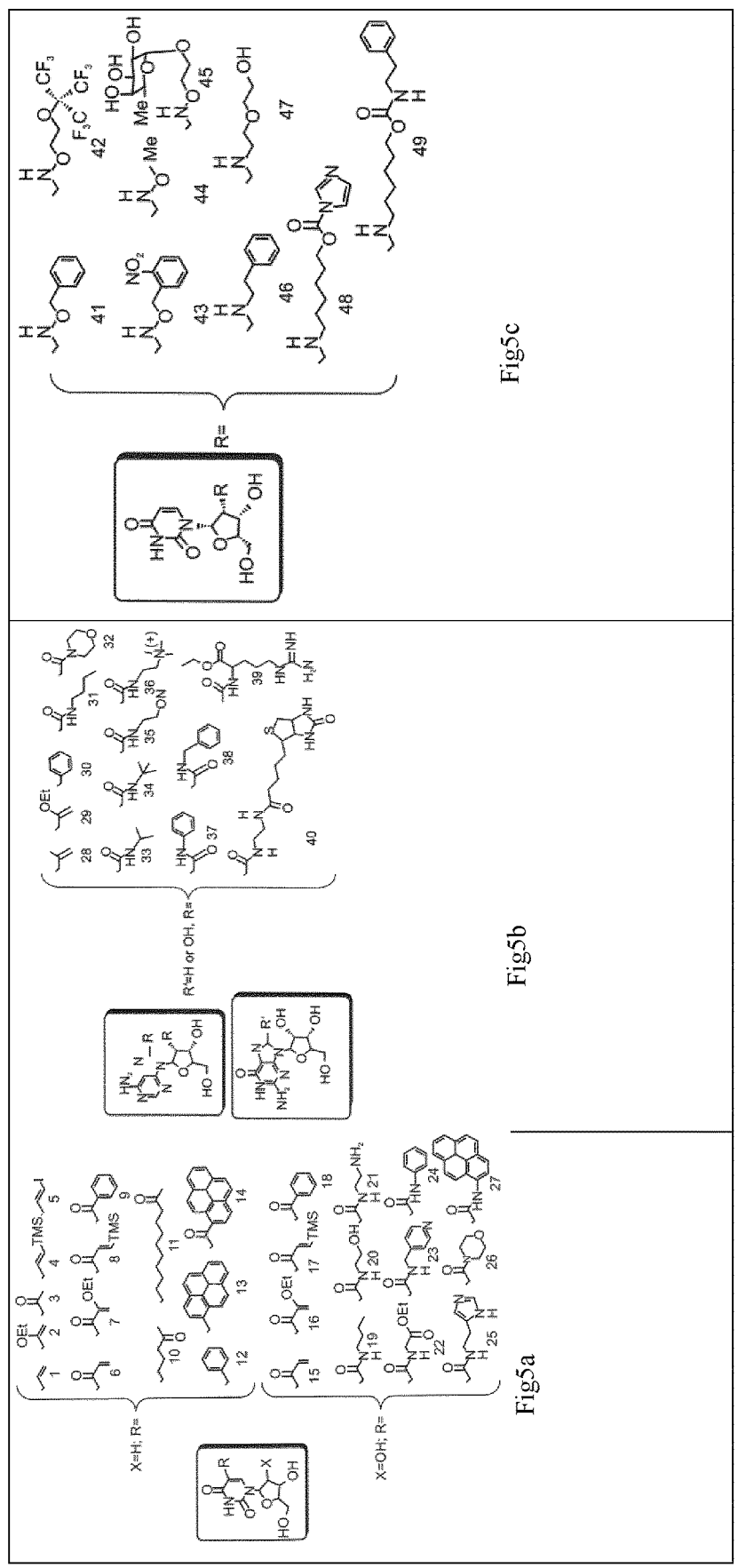
FIGS. 5 a-c are schematic illustrations depicting nucleic acid modifications.

Pyrimidine base modifications, such as DNA uridine nucleoside modifications at position 5, can include hydrophobic groups which can be conjugated in the form of ketones (ex. groups 17, 18 FIG. 5a], amides (groups, 24, 27, FIG. 5a) and the like, which can be attached to either DNA or RNA nucleic acid molecules[48]. It will be appreciated that amides can impart hydrogen-bonding capabilities to the aptamer. In any case, as described hereinabove, cross-linking carbonyl groups can be attached to the 5-position of uridine (groups 15-18, FIG. 5a). It will be appreciated, though, that the expected reactivity of carbonyl linkers can differ significantly depending on the interface of the target polypeptide.

Examples of purine modifications are shown in FIG. 5b. For example hydrophobic substituents can be attached at the 8-position of DNA purine nucleosides (groups 28-30, FIG. 5b). The degree of steric hindrance can be varied via amide linkages (groups 31, 33, 34, 37 and 38, FIG. 5b). Hydrophilic (group 35, FIG. 5b) and charged (groups 36 and 39, FIG. 5b) groups may be appended to the 8 position of purine nucleosides. It will be appreciated that functional groups with known affinity to the target polypeptide can be attached to the 8 position of the purine base, such as a biotinylated nucleoside (group 40, FIG. 5b).

Additional sites for modifications include but are not limited to the 3'-position of DNA. A 3'-position pyrimidine nucleoside modification can be implemented. Essentially, amine linkers, such as hydroxyl amine linkers can be used to attach hydrophobic groups with different topologies (groups 41-43, 46 and 49, FIG. 5c), hydrophilic groups (45 and 47, FIG. 5c) and groups exhibiting specific affinity to the target polypeptide (group 45, FIG. 5c).

As mentioned hereinabove, the nucleic acid molecules of this aspect of the present invention can also be modified to increase bioavailability thereof. The following illustrates non-limiting examples for such modifications.

The nucleic acid molecules of this aspect of the present invention may comprise heterocyclic nucleosides consisting of purines and the pyrimidines bases, bonded in a 3' to 5' phosphodiester linkage.

Preferably used nucleic acid molecules are those modified in either backbone, internucleoside linkages or bases, as is broadly described hereinunder. Such modifications can oftentimes facilitate oligonucleotide uptake and resistance to intracellular conditions.

Specific examples of nucleic acid molecules useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050, each of which are incorporated by reference in their entirety.

Preferred modified nucleic acid backbones include, for example, phosphorothioates, chiral phosphorothioates, phosphorodithioates, phosphotriesters, amino alkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,677,439, each of which are incorporated by reference in their entirety.

Other nucleic acid molecules which can be used according to the present invention, are those modified in both sugar and the internucleoside linkage, i.e., the backbone, of the nucleotide units are replaced with novel groups. The base units are maintained for complementation with the appropriate polynucleotide target. An example for such a nucleic acid sequence mimetic includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374, which is incorporated by reference in its entirety.

Nucleic acid molecules of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in the opened literature[49]. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C.[50] and are presently preferred base substitutions, even more particularly when combined with 2'-O-methoxyethyl sugar modifications.

Another modification of the nucleic acid molecules of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-racglycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety[51].

It is not necessary for all positions in a given oligonucleotide molecule to be uniformly modified, and in fact more than one of the aforementioned modifications may be incorporated in a single compound or even at a single nucleoside within an oligonucleotide.

As is illustrated in the following examples, the present inventors have conclusively shown that the nucleic acid molecules of the present invention are capable of preventing M. hyopneumoniae infection of cells in vitro and in vivo. Furthermore, the ability of the nucleic acid molecules of the present invention to inhibit viral spread following viral challenging, suggests the use of the nucleic acid molecules of the present invention in anti-M. hyopneumoniae prophylactic and therapeutic applications.

Method of Treating Infection

Thus, according to another aspect of the present invention there is provided a method of treating M. hyopneumoniae infection.

As used herein the term "treating" refers to preventing M. hyopneumoniae infection or substantially reducing (i.e., alleviating or diminishing) symptoms associated with M. Hyopneumoniae infection.

The method is implemented by providing to a subject in need thereof, a therapeutically effective amount of the nucleic acid molecule of the present invention described hereinabove.

As used herein "a subject in need thereof" refers to a subject suffering from M. Hyopneumoniae infection associated symptoms or at risk of contracting M. Hyopneumoniae infection. Examples of such subjects include but are not limited to piglets aged 6 weeks or less; mature pigs 12 weeks or more, pigs suffering from chronic diseases such as PRRSV infection, pregnant sows, and pigs in close or frequent contact with anyone at high risk.

Preferably, the nucleic acid molecules of the present invention are provided at a concentration of between, 0.1-150 µg/Kg body weight, preferably 1-100 µg/Kg body weight, more preferably 1-50 µg/Kg body weight and even more preferably 1-15 µg/Kg body weight.

Prior to, concomitant with or following providing the nucleic acid molecule of the present invention an agent can be provided to the subject. An agent can be a molecule that facilitates prevention or treatment of M. hyopneumoniae infection or clinical conditions associated with PRRS infection such as pneumonia. Examples of agents, according to this aspect of the present invention include, but are not limited to, immunomodulatory agents (e.g., synthetic antibodies), antibiotics, antiviral agent (e.g., amantidine), antisense molecules, ribozymes and the like.

The Pharmaceutical Composition

The nucleic acid molecule (i.e., active ingredient) of the present invention can be provided to the subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. The term "adjuvant" is included under these phrases.

Since activity of aptamers is directly correlated with a molecular weight thereof, measures are taken to conjugate the nucleic acid molecules of the present invention to high molecular weight carriers. Such high molecular weight carriers include, but are not limited to, polyalkylene glycol and polyethylene glycol (PEG), which are biocompatible polymers with a wide range of solubility in both organic and aqueous media[see J. Wang et al., [48]].

Alternatively, microparticles such as microcapsules or cationic lipids can serve as the pharmaceutically acceptable carriers of this aspect of the present invention. As used herein, microparticles include liposomes, virosomes, microspheres and microcapsules formed of synthetic and/or natural polymers. Methods for making microcapsules and microspheres are known to the skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be generated by methods well known in the art[52]. Alternatively, the nucleic acid molecules of this aspect of the present invention can be incorporated within microparticles, or bound to the outside of the microparticles, either ionically or covalently Cationic liposomes or microcapsules are microparticles that are particularly useful for delivering negatively charged compounds such as the nucleic acid molecules of this aspect of the present invention, which can bind ionically to the positively charged outer surface of these liposomes. Various cationic liposomes are known to be very effective at delivering nucleic acids or nucleic acid-protein complexes to cells both in vitro and in vivo, as reported[53].

Cationic liposomes or microcapsules can be generated using mixtures including one or more lipids containing a cationic side group in a sufficient quantity such that the liposomes or microcapsules formed from the mixture possess a net positive charge which will ionically bind negatively charged compounds. Examples of positively charged lipids which may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium (DOTMA).

As mentioned hereinabove the pharmaceutical compositions of this aspect of the present invention may further include excipients. The term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Various techniques for formulation and administration of drugs may be found in the opened literature[54]. Suitable routes of administration may, for example, include oral, transmucosal, especially transnasal, parenteral delivery, including intramuscular, subcutaneous and intramedullary injections as well as intranasal, or intraocular injections. Alternately, one may administer a preparation in a local rather than systemic manner, for example, via injection of the preparation directly into the lungs.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. The "proper" formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion. Pharmacological preparations for oral use can also be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatine as well as soft, sealed capsules made of gelatine and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., carbon dioxide, or dichlorodifluoromethane, trichlorofluoromethane, or dichloro-tetrafluoroethane[55]. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents[55].

Pharmaceutical compositions for parenteral administration include aqueous solutions of the active preparation in water-soluble form[55]. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents that increase the solubility of the active ingredients to allow for the preparation of highly concentrated solutions[55].

Alternatively, the active ingredient may be in powder form for constitution with a suitable vehicle, e.g., sterile, pyrogen-free water based solution, before use[55].

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art. For any preparation used in the methods of the invention, the therapeutically effective amount or dose can be estimated initially from in vitro assays. For example, a dose can be formulated in small animal models and such information can be used to more accurately determine useful doses in herds.

Toxicity and therapeutic efficacy of the active ingredients described herein can be verified by standard pharmaceutical procedures in vitro, in cell cultures or experimental animals[56]. The data obtained from these in vitro and cell culture assays and animal studies can be used in formulating a range of dosage for use in herds. The dosage may vary depending upon the dosage form employed and the route of administration utilized.

Depending on the severity and responsiveness of the condition to be treated, dosing can be of a single or a plurality of administrations, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing veterinarian, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be a labeling approved by the U.S. Food and Drug Administration for veterinary prescription drugs or of an approved product insert.

To enable cellular expression of DNA nucleic acid molecules of the present invention, the nucleic acid construct of the present invention further includes at least one "cis acting regulatory element". As used herein, the phrase "cis acting regulatory element" refers to a polynucleotide sequence, preferably a promoter, which binds a trans-acting regulator and regulates the transcription of a coding sequence located downstream thereto.

Any available promoter can be used by the present methodology. Preferred promoters for use in aptamer expression vectors include the pol III promoters such as the human small nuclear U6 gene promoter and tRNA gene promoters[57]. It will be appreciated that many pol III promoters are internal and are located within the transcription unit such that pol III transcripts include promoter sequences. To be useful for expression of aptamer molecules, these promoter sequences should not interfere with the structure or function of the aptamer. Therefore a preferred RNA pol III RNA promoter is the U6 gene promoter that is not internal[58]. Suitable pol III promoter systems useful for expression of aptamer molecules are well described in the opened literature[59]. It will be appreciated that promoters from the host cell or related species also can also be used.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a tissue of choice. The construct according to the present invention can be, for example, a plasmid, a bacmid, a phagemid, a cosmid, a phage, a virus or an artificial chromosome.

Preferably, cationic lipids are used in combination with a neutral lipid in equimolar amounts as described hereinabove. Neutral lipids of use in transfection complexes include, for example, dioleoyl phosphatidylethanolamine (DOPE) or cholesterol.

Typically a lipid mixture is prepared in chloroform, dried, and rehydrated in, e.g., 5% dextrose in water or a physiologic buffer to form liposomes. The resulting liposomes are mixed with a nucleic acid solution with constant agitation to form the cationic lipid-nucleic acid transfection complexes[56-57].

Prior to, concomitant with or following providing the nucleic acid molecule of the present invention an agent can be provided to the subject. An agent can be a molecule that facilitates prevention or treatment of M. hyopneumoniae infection or clinical conditions associated with PRRS infection such as pneumonia. Examples of agents, according to this aspect of the present invention include, but are not limited to, immunomodulatory agents (e.g., synthetic antibodies), antibiotics, antiviral agent (e.g., amantidine), antisense molecules, ribozymes and the like.

The antibody-like nature (i.e., specific binding to a polypeptide target) of the nucleic acid molecules of the present invention, allows the agents described hereinabove to be specifically targeted to an infectious tissue upon attachment to the administered nucleic acid molecule. For example an antisense molecule directed at a M. hyopneumoniae polypeptide (further described in the background section) can be targeted using the aptameric sequences of the present invention. "Chimeric" antisense molecules" are oligonucleotides that contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids.

Chimeric antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; each of which is herein fully incorporated by reference.

Alternatively a ribozyme sequence can be targeted using the nucleic acid molecules of the present invention. Ribozymes are being used for the sequence-specific inhibition of gene expression by the cleavage of mRNAs. Several ribozyme sequences can be fused to the oligonucleotides of the present invention.

Optionally, "DNAzymes" can be targeted using the methodology of the present invention. DNAzymes are single-stranded, and cleave both RNA. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions[60].

Examples of construction and amplification of synthetic, engineered DNAzymes recognizing single and double-stranded target cleavage sites have been disclosed in U.S. Pat. No. 6,326,174.

Methods of nucleic acid-lipid coupling are well known in the art and described in U.S. Pat. No. 5,756,291. For example, patent application WO 2004076621 A2 describes a variety of methods for formation of conjugates between nucleotide sequences and chelating agents; the chelating agent is joined to the nucleotides sequence by either a covalent bond or a linking unit derived from a polyvalent functional group. Thus, the aptamers or modified aptamers of the invention may be used alone in therapeutic applications or may be used for targeting agents to deliver pharmaceuticals or toxins to desired targets.

Detection of M. hyopneumoniae in Biological Samples

The ability of the nucleic acid molecules of the present invention to specifically bind polypeptides of the M. hyopneumoniae allows the use thereof in diagnostic applications. To date, a number of tests are available for the diagnosis of M. hyopneumoniae infection. A traditional approach for identifying M. hyopneumoniae in biological samples involves cell culturing, thereby providing highly sensitive and specific detection of viral infection. However, this approach is significantly limited by the time required for cell culturing and identification of M. hyopneumoniae can range between 2 and 8 weeks, thus making it ineffective in guiding the physician to an appropriate therapy. Since M. Hyopneumoniae infection is normally self-limited, diagnosis must be rapid if therapy is to be effective. Thus, cell culture methods are used only for providing retrospective epidemiological information.

Other Mycoplasma Hyopneumoniae diagnostic methods include the use of monoclonal immunofluorescence assays and enzyme-linked immunoassay. However, not only are these methods limited to the identification of type A M. hyopneumoniae infection, but they require considerable technical expertise, and result in high levels of false-negatives[22]. While accurate detection of MH by PCR has been reported[22-26], it was found that the ability to detect various MH field isolates differed significantly, and this was attributed to genetic differences among the isolates. This observation suggests that further research is required to determine the accuracy of detection of MH by PCR under field conditions.

Thus, according to yet another aspect of the present invention there is provided a method of identifying M. hyopneumoniae in a biological sample.

As used herein a biological sample refers to any body sample such as blood, pleural fluid, respiratory fluids and nasal aspirates. Methods of obtaining body fluids from vertebrates are well known in the art.

The method is implemented by contacting the biological sample with a nucleic acid molecule including a polynucleotide sequence capable of specifically binding an M. Hyopneumoniae polypeptide, described hereinabove.

The nucleic acid molecules of the present invention can be attached to a solid substrate, such as described here in below.

Contacting is carried-out under conditions that allow the formation of a polypeptide-nucleic acid molecule duplex. Duplexes are preferably washed to remove any non-specifically bound polypeptides allowing only those nucleic acid molecules specifically bound within the complexes to be detected.

Polypeptide-bound nucleic acid molecules in the biological sample are detected to thereby identify the Mycoplasma Hyopneumoniae infection.

In general monitoring of polypeptide-nucleic acid molecule complexes is well known in the art and may be carried-out as described hereinabove. These approaches are generally based on the detection of a label or marker, such as described here in below. Preferably, detection of an infected sample is effected by comparison to a normal sample, which is not infected with the M. hyopneumoniae.

The Method of Generating the Nucleic Acid Sequence

To generate the nucleic acid molecules of the present invention, a robust selection approach is preferably employed.

Thus, according to an additional aspect of the present invention there is provided a description of the method used to generate nucleic acid molecules capable of inhibiting M. hyopneumoniae infection.

The method is implemented as follows. First, a plurality of nucleic acid molecules are contacted with a polypeptide target, which participates in M. hyopneumoniae infection of cells as described hereinabove. Following duplex formation (i.e., a non-Watson Crick complementation between the polypeptide target and the nucleic acid molecules), at least one nucleic acid molecule of the plurality of nucleic acid molecules that is capable of specifically binding the polypeptide is identified. Finally, polypeptide bound nucleic acid molecules are isolated to thereby generate the molecule that is capable of inhibiting M. Hyopneumoniae infection.

Double stranded DNA molecules can be generated from a library of oligonucleotide sequences including a randomized polynucleotide sequence flanked by two defined nucleotide sequences that can be used for polymerase chain reaction (PCR) primer binding. The library is amplified to yield double-stranded PCR products. The randomized sequences can be completely randomized (i.e., the probability of finding a base at any position being 1:4) or partially randomized (i.e., the probability of finding a base at any position is selected at any level between 0-100%).

For preparation of single stranded aptamers, the downstream primer is biotinylated at the 5' end and PCR products are applied to an avidin agarose column. Single stranded DNA sequences are recovered by elution with a weakly basic buffer. Single stranded RNA molecules can be generated from an oligonucleotide sequence library, which is amplified to yield double-stranded PCR products containing a T7 bacteriophage polymerase promoter site. RNA molecules can then be produced by in vitro transcription using T7 RNA polymerase.

The nucleic acid molecules of this aspect of the present invention can be generated from naturally-occurring nucleic acids or fragments thereof, chemically synthesized nucleic acids, enzymatically synthesized nucleic acids or nucleic acid molecules made by a combination of the foregoing techniques The library of this aspect of the present invention is generated sufficiently large to provide structural and chemical coverage of selected nucleic acid modifications described hereinabove.

Typically, a randomized nucleic acid sequence library according to this aspect of the present invention includes at least $10^{14}$ sequence variants.

Nucleic acid modifications can be effected prior to incubation with the target polypeptide. In this case, although screening is implemented on the final modified aptamer, modification is restricted not to interfere with any process, such as an enzymatic process (e.g., transcription), which takes place during the screening.

Alternatively, a nucleic acid molecule can be modified following selection (i.e., isolation of a polypeptide bound nucleic acid molecule). Thus, a wide range of functional groups can be used simultaneously. In this case, electrospray ionization mass spectrometry (ESI-MS) can be used to elucidate the right functional group.

In any case, once nucleic acid molecules are obtained they are contacted with the polypeptide target, as mentioned hereinabove.

Incubation of the nucleic acid molecules with the target polypeptide of this aspect of the present invention is preferably implemented under physiological conditions. As used herein the phrase "physiological conditions" refers to salt concentration and ionic strength in an aqueous solution, which characterize fluids found in the metabolism of vertebrate animal subjects which can be infected with *M. hyopneumoniae*, also referred to as physiological buffer or physiological saline. For example physiological fluids of swine are represented by an intracellular pH of 7.1 and salt concentrations (in mM) of sodium 3-15; potassium 140; magnesium 6.3; Calcium 10-4; Chloride 3-15, and an extracellular pH of 7.4 and salt concentrations (in mM) of sodium 145; potassium 3; Magnesium 1-2; Calcium 1-2; and Chloride 110.

The nucleic acid molecules can be incubated with the target polypeptide either in solution or when bound to a solid substrate.

It will be appreciated that some of the above-described base modifications can be used as intermediates for attaching the nucleic acid molecule to a solid substrate. For example, the modified uridine shown in group 48 of FIG. 5c, can serve as a common intermediate which may be further modified by substitution of the imidazole with a wide variety of hydrophobic, hydrophilic, charged and cross linking groups, prior to activation as the phosphoramidite reagent used in solid phase synthesis Methods for attaching nucleic acid molecules to solid substrates are known in the art including but not limited to glass printing, photolithographic techniques, inkjet printing, masking and the like.

Typically, a control sample is included to select against nucleic acid molecules that bind to non-target substances such as the solid support and/or non-target peptides/proteins.

Separation of unbound nucleic acid sequences and identification of bound nucleic acid sequences can be effected using methods well known in the art. Examples include, but are not limited to, selective elution, filtration, electrophoresis and the like.

Alternatively, imaging can identify bound aptameric molecules. For example, optical microscopy using bright field, epifluorescence or confocal methods, or scanning probe microscopy can be used to identify a polypeptide bound nucleic acid molecule. To facilitate visualization, nucleic acid molecules or polypeptides are preferably labeled using any radioactive, fluorescent, biological or enzymatic tags or labels of standard use in the art[61].

The following illustrates a number of labeling methods suitable for use in the present invention. For example, nucleic acid molecules of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, fluorescent moieties are used, including but not limited to fluorescein, lissarine, phycoerythrin, rhodamine, Cy2, Cy3, Cy3.5, Cy5, Cy5.5, Cy7, FluorX and others.

It will be appreciated that the intensity of signal produced in any of the detection methods described hereinabove may be analyzed manually or using a software application and hardware suited for such purposes.

Isolation of an aptamer sequence (i.e., polypeptide-bound nucleic acid) typically involves sequence amplification such as by PCR. Amplification may be conducted prior to, concomitant with or following separation from the target polypeptide. The PCR method is well known in the art[62]. It will be appreciated that if RNA molecules are used, the amplified DNA sequences are transcribed into RNA.

The recovered nucleic acid molecule, in the original single-stranded or duplex form, can then be used for iterative rounds of selection and amplification (i.e., target polypeptide binding). Typically, following three to six rounds of selection/amplification, nucleic acid molecules that bind with a preferred affinity of nM to M range can be obtained.

It will be appreciated that methods for identifying nucleic acid molecules capable of specifically binding polypeptide targets are known in the art[27]. For example, U.S. Pat. No. 5,270,163, incorporated by reference in its entirety, discloses the SELEX method for the identification of nucleic acid ligands as follows. A candidate mixture of single-stranded nucleic acids having regions of randomized sequence is contacted with a target compound and those nucleic acids having an increased affinity to the target are partitioned from the remainder of the candidate mixture. The partitioned nucleic acids are amplified to yield a ligand-enriched mixture. The target-oligonucleotide complexes are then separated from the support and the uncomplexed oligonucleotides, and the complexed oligonucleotides are recovered and subsequently amplified using PCR. The recovered oligonucleotides may be sequenced and subjected to successive rounds of selection using complexation, separation, amplification and recovery.

Alternatively, the nucleic acid sequences of the present invention can be generated by rational drug design. Rational drug design is the inventive process of finding new medications based on the knowledge of a biological target[63]. The drug is most commonly an organic small molecule that activates or inhibits the function of a biomolecule such as a protein, which in turn results in a therapeutic benefit. Thus, rational drug design is a potent means of identifying small molecules that are complementary in shape and charge to the biomolecular target with which they interact and therefore will bind to it.

Alternatively, a refined aptamer sequence can be elucidated by modifying a known aptamer structure (e.g., APT3Cooc10)) using a software comprising "builder" type algorithms which utilizes a set of atomic coordinates defining a three dimensional structure of the binding pocket and the three-dimensional structures of the basic aptamer to computationally assemble a refined aptamer. Ample guidance for performing rational drug design via software employing such "scanner" and "builder" type algorithms is available in the literature of the art[64].

Criteria employed by software programs used in rational drug design to qualify the binding of screened aptamer structures with binding pockets include gap space, hydrogen bonding, electrostatic interactions, van der Waals forces, hydrophilicity/hydrophobicity, etc[65]. Generally, the greater the contact area between the screened molecule and the polypeptide binding region, the lower the steric hindrance, the lower the "gap space", the greater the number of hydrogen bonds, and the greater the sum total of the van der Waals forces between the screened molecule and the polypeptide binding region of, the greater will be the capacity of the screened molecule to bind with the target polypeptide. The "gap space" refers to unoccupied space between the van der Waals surface of a screened molecule positioned within a binding pocket and the surface of the binding pocket defined by amino acid residues in the binding pocket. Gap space may be identified, for example, using an algorithm based on a series of cubic grids surrounding the docked molecule, with a user-defined grid spacing, and represents volume that could advantageously be occupied by a modifying the docked aptamer positioned within the binding region of the polypeptide target. Contact area between compounds may be directly calculated from the coordinates of the compounds in docked conformation using various commercially available Molecular Structure (MS) software packages.

In any case, once putative aptamer sequences are identified they are examined for specific binding to the target polypeptide, which can be implemented using a number of biochemical methods known in the art[66].

Alternatively or additionally, the nucleic acid sequences of the present invention are tested for inhibiting *M. hyopneumoniae* infection in vitro such as with pulmonary ciliated epithelial cell line, or in vivo as further described in Example 2 (in vitro) and Example 3 (in vivo) of the Examples section.

As mentioned hereinabove, the nucleic acid sequences of the present invention can be used for treating *M. hyopneumoniae* infection.

Thus according to yet a further aspect of the present invention there is provided a method of treating *M. hyopneumoniae* infection.

The method is implemented by providing to a subject in need thereof, a therapeutically effective amount of the polynucleotide and/or synthetic antibody of the present invention, described hereinabove.

Preferred administration routes and pharmaceutical compositions are described hereinabove.

It will be appreciated that synthetic antibodies generated according to the teachings of the present invention can be used also for identifying *M. hyopneumoniae* in a biological sample.

The method can be implemented by contacting a biological sample such as described hereinabove, with the synthetic antibody of the present invention. Thereafter, immunocomplexes including the synthetic antibody in the biological sample are detected, to thereby identify the *M. hyopneumoniae* strain in the biological sample.

The nucleic acid molecules, conjugates thereof, polynucleotides, and synthetic antibodies generated according to the teachings of the present invention can be included in a bio-detection device or a diagnostic kit or therapeutic kit. These reagents can be packaged in one or more containers with appropriate buffers and preservatives and used for diagnosis or for directing therapeutic treatment.

Thus, nucleic acid molecules and conjugates thereof can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added. The nucleic acid molecules and conjugates thereof of such kits can also be attached to a solid support, as described and used for diagnostic purposes.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature[67]. The procedures therein are believed to be well known in the art and are provided for the convenience of the reader. All the information contained therein is incorporated herein by reference.

Example 1 the Peptidic P97 Complex Specific Aptamers Rationale and Design

Systematic Evolution of Ligands by Exponential Enrichment (SELEX) was implemented in order to identify aptamer oligonucleotides that bind the *M. hyopneumoniae*.

Materials and Experimental Procedures

Library Generation—

The aptamer library containing a central randomized sequence of 40 nucleotides flanked by a common 5' sequence—AAT TAA CCC TCA CTAAAG GG, denoted as T3 (SEQ ID NO: 21) and a common 3' sequence—5'-TAT GGT CGA ATA AGT TAA-3' (SEQ ID NO. 22) was synthesized in a 380B DNA synthesizer. The library included a 30 nucleotides random segment, over all $10^{16}$ molecules and generated according to manufacturer's instructions.

SELEX— ssDNA aptamers were denatured at 80° C. for 10 min and then cooled on ice for 10 min. Aptamers 30 nmole were mixed with 25 µg of P97 peptidic complex (further described herein below) in 500 pl selection buffer (50 mM Tris-HCl; pH 7.4, 5 mM KCl, 100 mM NaCl, 1 mM MgCl$_2$ tRNA, 0.2% BSA) at 37° C. for 30 min. Aptamer-peptide complex was purified by adding the 25 µl Ni-NTA superflow (Qiagen) and amplified by PCR using primers directed to the common sequences in the aptamer library, i.e., 5'-AAT TAA CCC TCA CTA AAG GG-3', (T3) and 3' primer 5' TTA ACT TAT TCG ACC ATA-3' (SEQ ID NO: 23). SELEX was repeated 3 times, following which amplified nucleotides were transformed into *E. coli*. PCR conditions for SELEX included 5 min 95° C./1 min 95° C./1 min 55° C./1 min 72° C./10 min 72° C. and 100 pmole of each primer.

Reverse Screening of Aptamer—

Selected ssDNA molecules from each individual clone were biotinylated using the B-T3 which is same sequence with 5' primer (T3 primer), and Klenow fragment (2 unit/ml). To prepare single stranded biotin conjugated APT3Cooc10 aptamer for the reverse screening. T3 Primer was Biotin labelled. A 96-well flat bottom ELISA plate was prepared by coating each well with 100 μl of streptavidin (100 μg/ml) diluted in 0.1 M NaHCO$_3$ following by a 37° C. overnight incubation. Following several washings with PBS, wells were blocked with 200 μl of PBS containing 1% BSA for 2 hours at room temperature and subsequent washing three times with PBS-T (10 mM PBS containing 0.05% (v/v) Tween-20). Thereafter, 100 μl of 2.5 pmole/100 μl biotinylated-ssDNA were added to the wells and incubated at 37° C. for 2 hours followed by washing four times with PBS-T. T3 primer was used as negative control. Following washing, 100 μl of fluid containing 2 μg histidine labelled P97 peptidic complex were added to the indicated wells and incubated at 37° C. for 2 hours. The wells were then washed for 4 times with PBS-T. The reverse screening assay was completed using the DAKO *Mycoplasma Hyopneumoniae* ELISA tests (K004311-9 kit, Oxoid Ltd, UK).

Enzyme-Linked Immunosorbent Assay (ELISA)—

The ELISA tests were carried-out following all the guidelines provided with the DAKO kit. Reaction was terminated with 100 μl of 0.5M H$_2$SO$_4$, and the plates were read with a multichannel spectrophotometer at 450 nm.

Results—

Figure 6:
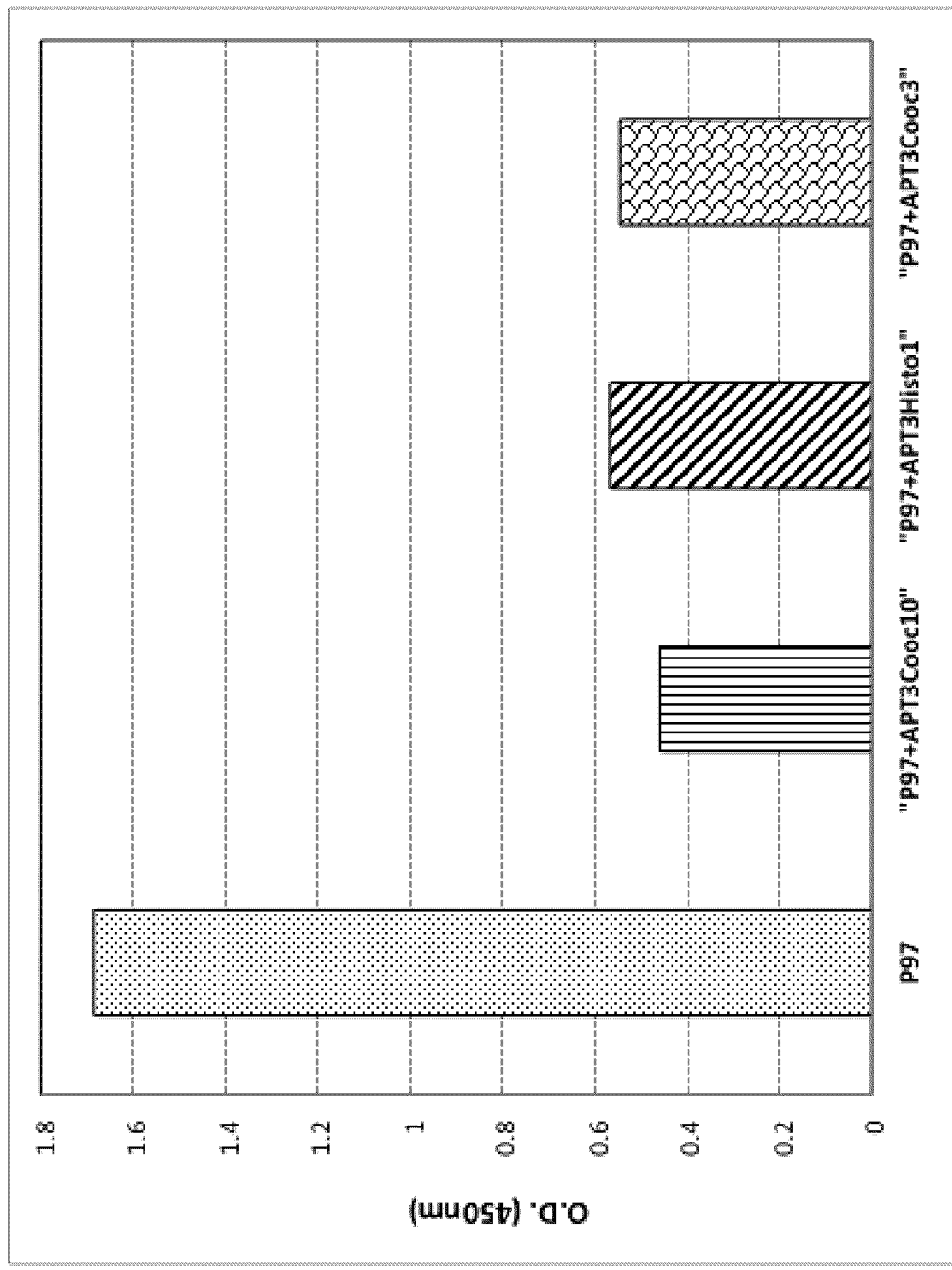
FIG. 6 is a histogram depicting binding levels of M. hyopneumoniae specific aptamers generated according to the teachings of the present invention (APT3Cooc10, APT3Histo1, and APT3Cooc3) and control single stranded aptamer to an intact M. Hyopneumoniae as determined by ELISA.

In order to identify oligonucleotides that bind to the peptidic complex P97, a nucleotide library containing random 30 nucleotides between conserved linkers, was synthesized. The library included $10^{16}$ types of different ssDNA, which were hybridized to the P97 peptidic complex and purified by Ni-NTA resin. Following purification, ssDNAs were amplified by PCR using the linker sequences. The process was repeated 4 times and re-screening of the P97 complex was implemented by ELISA. This reverse-screening process resulted in three oligonucleotide aptamers denoted as "APT3Cooc10", "APT3Histo1", and "APT3Cooc3". All three aptamers showed similar binding capacity to the P97 complex (FIG. 6). Note a significant protection of APT3-Cooc10 and APT3cooc3 against the intact virus as compared to control nucleic acid is notable (p=0.042 and p=0.0008, respectively), and a significant reduction in APT3-Cooc10 binding to the intact virus as compared to the APT3-Cooc3 aptamer (p=0.017). Therefore, structural and functional analysis of the APT3Cooc10 and APT3Cooc3 oligonucleotides only was further implemented. Proposed secondary structures using DNAdraw program for APT3Cooc10, APT3Histo1, and APT3Cooc3, as well as a control oligonucleotide are shown in FIGS. 4*a, e, c*, respectively.

Example 2. In-Vitro Aptamer Protection from *M. hyopneumoniae* Infection

The protective effect of the APT3Cooc10 aptamer against two virulent strains of *M. Hyopneumoniae* was investigated in vitro using cilia of pulmonary epithelium cells (PEC).

Materials and Experimental Procedures

*Mycoplasma Hyopneumoniae*—

*M. hyopneumoniae* 232 (GenBank accession AE017332) and *M. hyopneumoniae* 7448 (GenBank accession AE017244) were obtained from the faculty of Veterinary Microbiology and Preventive Medicine, Iowa State University, Ames, Iowa 50111, USA (Prof. F. C. Minion). The cells were grown in modified Friis medium at 37° C. and harvested during the exponential phase when the medium became honey coloured and pH was in the range 6.9-7.2. Mycoplasma cells were harvested by centrifugation at 10 000 g for 20 min and the pellets were washed twice with Tris-buffered saline (TBS: 10 mM Tris/HCl, 150 mM NaCl; pH 7.5) and the final pellets were frozen a −20° C. until use. When used, the pellet of Mycoplasmas was re-suspended to 1/10 of the original volume in an adherence buffer (AB) that consisted of a RPMI 1640 medium containing 1% gelatin.

Cells, and Cilia Extraction—

Pulmonary Epithelium Cells (PEC) were obtained from RTI LLC (Brookings, S. Dak.) and maintained in Dulbecco's modified Eagle's medium (DMEM) supplemented with heat inactivated 10% fetal calf serum (FCS). The cilia were extracted and purified from the harvested PEC using the method described by Zhang et al.[20]. In brief, ciliated cells were suspended in 40 ml of buffer containing 20 mM Tris, 10 mM EDTA, and 125 mM sucrose (TES buffer [pH 7.2]). Two washings with TES buffer were conducted by centrifugation at 300×g for 5 min. The cell pellet was re-suspended in 6 ml of AES buffer (80 mM acetate, 10 mM EDTA, 125 mM sucrose [pH 6.8]) and incubated for 5 min at 25° C. Then, 0.2 M CaCl was added to a final concentration of 10 mM. The mixture was vortexed for 10 min, diluted with 20 ml of TES buffer, and then centrifuged at 500×g for 10 min. The sediment, which contained mainly cell bodies, was discarded, and the supernatant, containing cilia, was harvested by centrifugation at 18,000×g for 15 min at 40° C. The ciliary pellet was washed twice with phosphate buffered saline (PBS) and stored at −80° C. The purity of the cilia was ascertained by light microscopy. Protein concentrations were determined with the bicinchoninic acid protein assay reagent (Pierce™ BCA Protein Assay Kit 23225, Thermo Scientific, Rockford, Ill.) according to the instructions provided with the product. Porcine albumin (fatty acid free; 10 g/ml) and gelatin (10 μg/ml) were used to coat plates as negative controls under the conditions used for cilia.

Coating of Plates, and Cilia Binding Assay—

Purified cilia (2 mg/ml in PBS) were solubilized with sodium dodecyl sulfate (SDS; 1 mg/mg of protein) at 37° C. for 45 min. This preparation was further diluted with sodium carbonate buffer (0.1 M; pH 9.5) to a final concentration of 10 μg of protein per ml. To each well of flat-bottom microtiter plates (Sarstedt, model 83.3824) was added 100 μl of this solution (1 μg of cilia per well) and incubated for 3 h at 37° C. Note that the cilia-coated plates can be stored at −80° C. for a long period (>6 months) without the loss of adherence[20].

After four washings with PBS (pH 7.4), the cilia-coated plates were blocked with 200 μl of AB per well for 2 h at 37° C. Then, 100 μl of *Mycoplasma Hyopneumoniae* cells re-suspended in AB was added to each well, and the plates were incubated at 37° C. for 90 min. Non-adherent Mycoplasmas were removed by four washings with PBS. Subsequently, 100 μl of rabbit antibodies to *M. hyopneumoniae* (Biorbyt, CA) was added and incubated at 37° C. for 60 min. The wells were washed four times with PBS and then incubated with 100 μl of goat anti-rabbit peroxidase conjugate (Abcam, MA) for 60 min at 37° C. After four washings with PBS, 100 μl of peroxidase substrate [2,2'-azinobis(3-ethylbenzthiazoline-6-sulfonic acid) (ABTS)] (from KPL Inc, Gaithersburg, Md.) was added to each well and incubated at 25° C. for 10 min. Optical densities (OD) at 405 nm were measured with an automated microplate reader (model ELx808IU; Bio-Tek Instruments, Inc., VT).

For the aptaneutralization assays, various aptamers diluted to appropriate concentrations in AB were mixed with Mycoplasmas and added to the cilium-coated plates. After incubation and washings, the binding of Mycoplasmas to the plates was detected with rabbit anti-*M. hyopneumoniae* antibodies and goat anti-rabbit conjugates as described above. To optimize the sensitivity to the neutralization, as suggested by Zhang et al.[20], $2.5 \times 10^8$ CCU of Mycoplasmas was used in each well so that the OD of the controls was about 0.5~0.6.

Two approaches were used to study neutralization/inhibition.
(i) The aptamers were pre-incubated with Mycoplasmas at 37° C. for 1 hr, and the incubated Mycoplasmas+aptamers were applied to the cilium-coated plates.
(ii) Cilium-coated plates were pre-incubated with the aptamers at 37° C. for 1 h, unbound aptamers were removed by four washings, and the Mycoplasmas were added to the plates.

Thereafter, procedures for both approaches were identical, including the sequential addition of antibodies to Mycoplasmas, secondary antibody conjugates, and peroxidase substrates. The percent neutralization was calculated as follows:

Percent neutralization=(OD from AB−OD from an aptamer)/OD value from AB.

The $IC_{50}$, representing the concentration of an aptamer that resulted in 50% inhibition, was determined from the neutralization kinetics obtained with multiple concentrations of the aptamer.

Results—

The aptamer ability to prevent the adhesion of *M. hyopneumoniae* onto the cilia of the pulmonary cells was tested. Typical results are shown in FIG. 7, where cells treated with aptamer APT3Cooc10 prior to *M. hyopneumoniae* infection demonstrated a significant reduction in *Mycoplasma* binding to the cilia.

Figure 7:
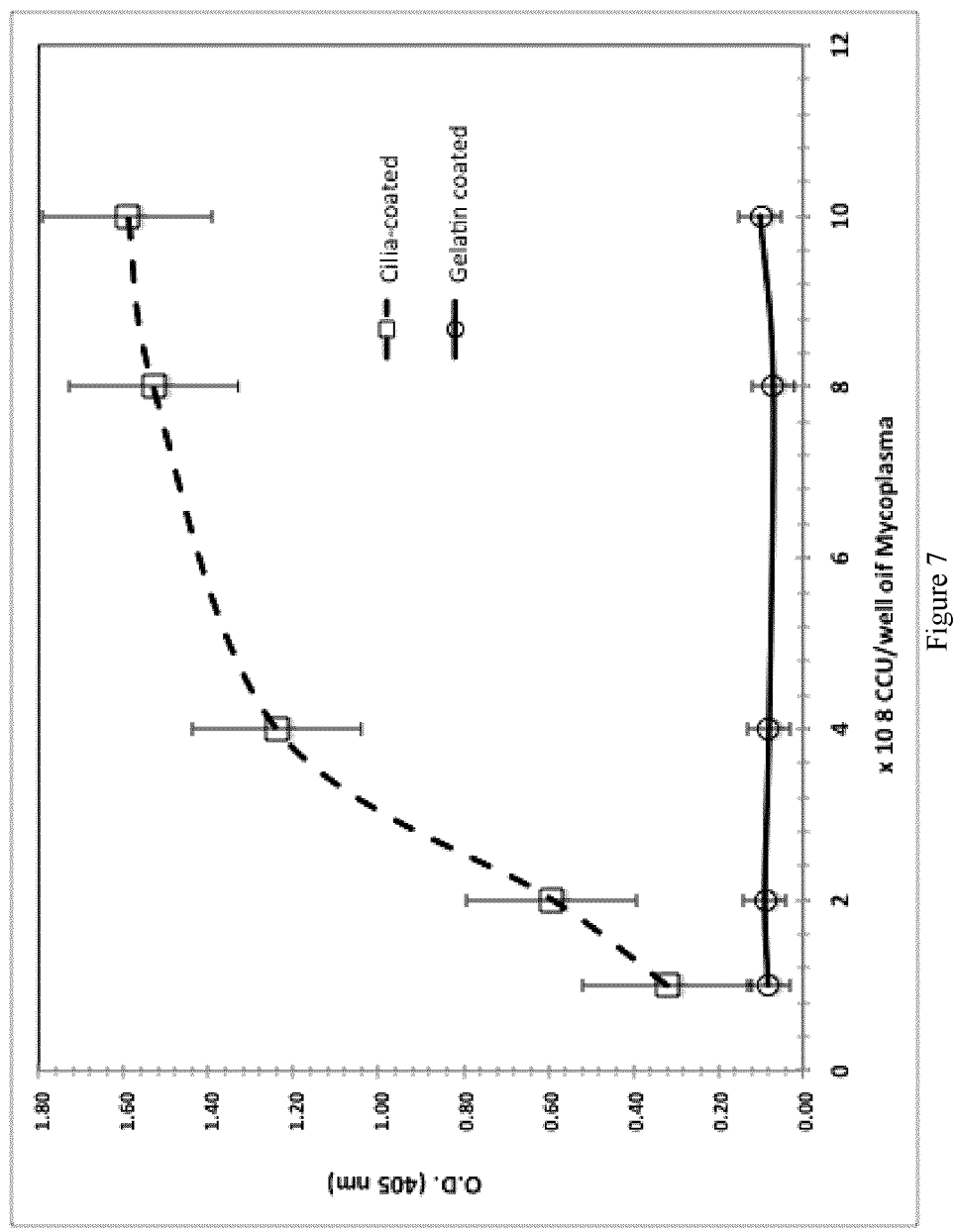
FIG. 7. is a graph showing the effects of Mycoplasma concentration on the binding to the cilia-coated plates and on the gelatin-coated plates.

*Mycoplasma Hyopneumoniae* bound specifically to cilium-coated wells but not to control wells coated with gelatin or porcine albumin (FIG. 7). Note that *mycoplasma* only binds to the cilia-coated plates and that the gelatin-coated plates are a very effective control for the binding assays. ODs obtained with the control wells (gelatin-coated) were always less than 0.10. As expected, the number of Mycoplasmas influenced the degree of binding. The concentration of cilia for coating the plates was 1 ug of protein per well. About $4 \times 10^8$ CCU of Mycoplasmas was required for half-maximal binding at 37° C. while about $10^9$ CCU of Mycoplasmas per well was required to reach saturated binding.

Figure 8:
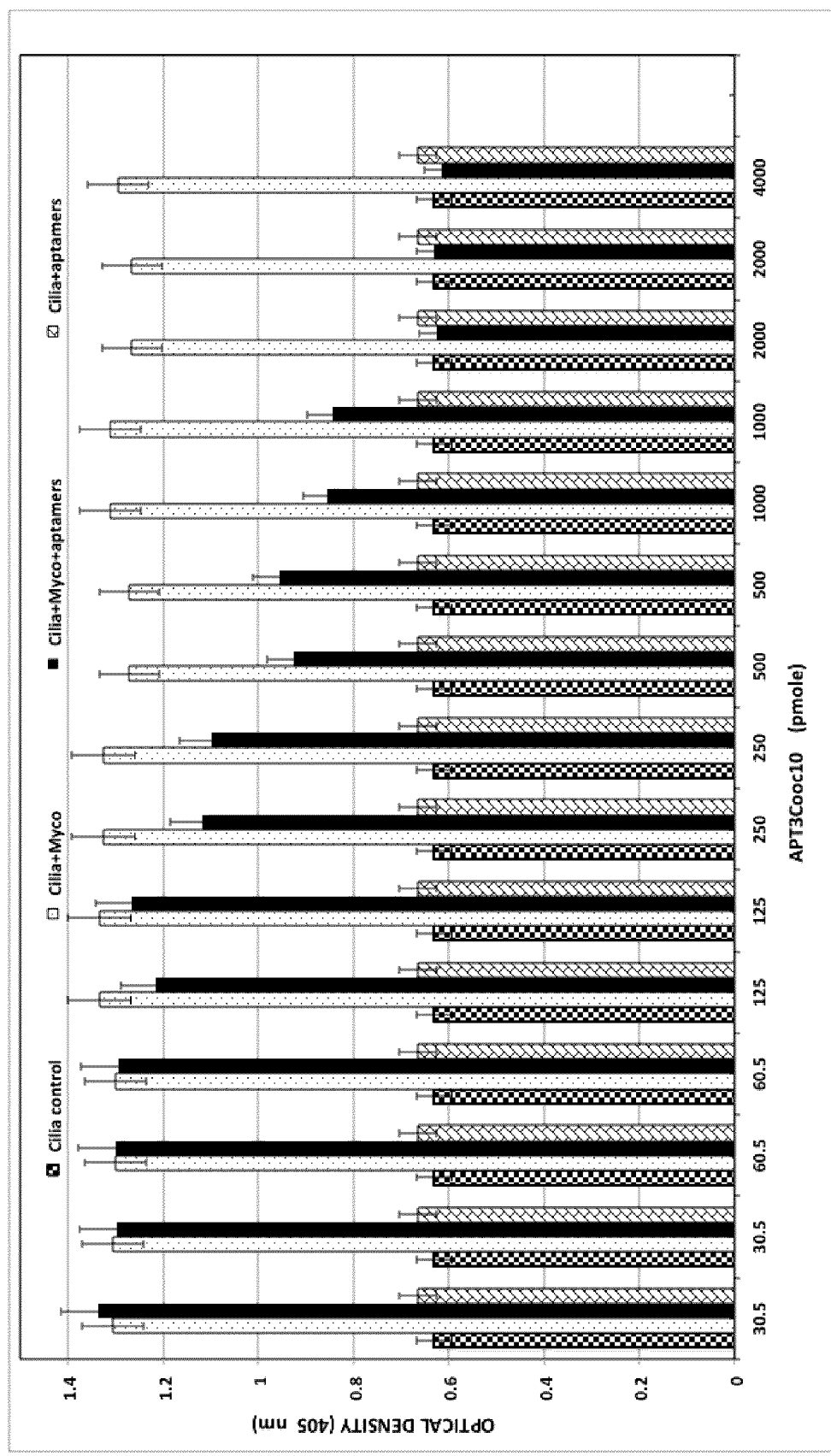
FIG. 8 is a graph showing dose response curve showing the effect of APT3Cooc10 aptamer of the present invention on viability of M. hyopneumoniae treated ciliated pulmonary cells as determined using the binding cilia assays.

Ten aptamers that bind to the P97 peptide have been identified. Three of them, APT3Cooc3, APT3Cooc10, and APT3Histo1, bound to the ligands on the surface of Mycoplasmas and therefore are receptor analogs. Since the binding of *Mycoplasma* onto the ciliated-plate is dependent on the concentration of *Mycoplasma* that is added to the wells (see FIG. 7), the quantity of aptamers that is needed to neutralize a given concentration of *Mycoplasma* is also concentration-dependent. FIG. 8 shows that about 2000 pmole of APT3Coo10 are required to prevent the adhesion of $4 \times 10^8$ CCU/well of *Mycoplasma* onto 1 μg/well of cilia. FIG. 8 also demonstrates that the aptamers do not bind, or modify the cilia and the ciliated cells.

The ability of APT3Cooc10 to prevent the adhesion of *Mycoplasma* onto the pulmonary ciliated cells is evident (see FIG. 8) and shows that APT3Cooc10, APT3Cooc3, and APT3Histo1 can be used to prevent or stop the propagation of *Mycoplasma* into the luminal surface of tracheas, bronchi, and bronchioles of swine. Furthermore, swine being exposed to nebulized particles containing any of these three aptamers will not have any detrimental or negative effects. As shown in FIG. 8, the highest protective effect was achieved using APT3-Cooc10 at the concentration range of 1000 to 4000 pmole.

Example 3 In-Vivo Aptamer Protection from *M. hyopneumoniae* Infection

The protective effect of the APT3Cooc10 aptamer against *M. hyopneumoniae* infection (the 232 strain) was determined using an experimental protocol similar to the one used by D. A. Murphy et al[68] for comparison purposes. In this older study, it was found that aerosolized commercial vaccine did not offer any protection against *Mycoplasma Hyopneumoniae* infection and only limited protection with the conventional intramuscular injection. The main difference between the two studies being that the commercial aerosolized vaccine was replaced by nebulized APT3Cooc10 aptamers.

Materials and Experimental Methods.

Swine—

Twenty-one American Yorkshire swine 8 weeks-old castrated male pigs were obtained from a closed commercial farm (*M.-Hyopneumoniae*-free as determined by repeated slaughter examination and serologic testing) and were randomly selected from 7 litters. The pigs were fed a normal grower ration that did not contain antibiotics.

Experimental Design—

The pigs were randomly assigned by litter and body weight to 1 of 3 treatment groups. The first group (PBS group) served as the negative-control, and was exposed to nebulized PBS. The second group (APT3 group) was exposed to nebulized aptamer solutions. The third group (commercial vaccine/CV group) was vaccinated using a commercially available injectable vaccine according to the manufacturer's label directions. Two weeks after the last aerosol vaccination, all pigs were challenge-exposed by intra-tracheal inoculation. Four (4) weeks after the challenge exposure, all pigs were necropsied and examined. In particular, pre-vaccination and post-vaccination serum were assayed for *M. hyopneumoniae* specific antibodies.

Vaccine

A commercially available injectable *M. hyopneumoniae* vaccine was obtained (Suvaxyn®MH One, Zoetis Canada Incorporated). The vaccine contains a proprietary water-soluble adjuvant. Pigs in the CV-group each received the recommended dose of 2 ml administered intramuscularly in the neck. A total of 2 doses were given at 2-weeks intervals. Pigs in the APT3-group each received 4000 pmole of APT3Cooc10, which was mixed with 10 ml of PBS and administered by nebulization. A total of 3 doses were given at two-week intervals.

Nebulizing Procedure—

The aptamers and the PBS for the first two groups were nebulized by use of a commercial nebulizer (PARI LC® Star nebulizer) that is producing 0.5-0 to 5 μm diameter aerosol particles (3.1 μm median size). Pure medical air was used with the nebulizer. Sterile re-usable chambers were used for nebulizing the APT3 and the PBS. The aerosol passed through a one-way valve from the nebulization chamber into a flexible 1 meter long tube, and was delivered to the pigs through an anaesthetic veterinary mask (SurgiVet, model 32393B1). The APT3 aerosol was not irritating to the pigs and tranquilization was not required. Pigs were restrained in a padded sling during the aerosol procedure. It tool 15 to 30 minutes for a pig to inhale its full dose of APT3 or PBS.

Challenge-Exposure Procedure—

The pigs were challenged with *M. hyopneumoniae* 232 (GenBank accession AE017332) that was obtained from the faculty of Veterinary Microbiology and Preventive Medicine, Iowa State University, Ames, Iowa 50111, USA (Prof. F. C. Minion). The cells were grown in modified Friis medium at 37° C. and harvested during the exponential phase when the medium became honey coloured and pH was in the range 6.9-7.2. *Mycoplasma* cells were harvested by centrifugation at 10,000 g for 20 min and the pellets were washed twice with Tris-buffered saline (TBS: 10 mM Tris/HCl, 150 mM NaCl; pH 7.5) and the final pellets were frozen a −20° C. until use. Each challenge group was inoculated intra-tracheally with an *M.-Hyopneumoniae* broth culture containing about $10^8$ CCU/ml of MH232.

Clinical Evaluation—

Pigs were monitored twice daily while the stalls were being cleaned, for a minimum of 15 min for clinical signs of illness, and observations were recorded on a scale of 0 (normal), 1 (mild abnormal) or 2 (severe abnormal) for general health, mobility, appetite and coughing at each inspection. The cumulative (total) coughing scores were calculated for each pig and a mean score per inspection was also determined. Pigs were weighed 3 days prior to challenge and again at 21 and 28 days post-challenge. Any pig that coughed more than once during that time was recorded as persistently coughing for that day. Pigs that would produce a short cough after putting their snout into the feed were not counted.

Necropsy—

The pigs were euthanatized by electrocution and exsanguination, and the lungs were removed quickly for evaluation. The lungs were evaluated for macroscopic lesions and scored using the Goodwin lung scoring system[8-9, 22, 39]. In addition, the percentage of affected lung was calculated by weighing all grossly consolidated lesions and comparing with the weight of the entire lung. The entire right lung was lavaged with four 50 ml aliquots of PBS. The total cells within the lavage fluid were counted manually by use of a hemocytometer. The remaining fluid was centrifuged, and the supernatant was stored for determination of antibody titer.

Quantitative Culture of Mycoplasmas—

The presence of *M. hyopneumoniae* in the lung mycoplasmal fluid was determined by use of immunohistochemistry (IHC) assay.

Immunohistochemical detection of *M. hyopneumoniae*-specific antigen on selected lung tissues was done using the heat-induced epitope retrieval technique. Paraffin-embedded tissue sections were dewaxed and rehydrated, covered with 1:10 ethylenediaminetetraacetic acid butter solution, pH 6.0, placed in a microwave, and boiled for 5 minutes. After cooling for 20 minutes, the slides were rinsed, and *M. Hyopneumoniae* monoclonal antibody (identification number D79DI-7 was applied in a 1:500 dilution for 2 hours at room temperature and further processed by using a labeled streptavidin-biotin detection kit (DAKO). Specificity of the *M. hyopneumoniae* IHC procedure was evaluated by testing sections from formalin-fixed paraffin-embedded blocks from pigs known positive for other pathogens (SIV, PRRSV). Specificity was determined to be 100%. There was no evidence of cross-reaction with any of the pathogens tested. Sensitivity was evaluated by comparing the IHC results with those obtained with *M. hyopneumoniae* culture, which is considered the gold standard for *M. Hyopneumoniae* detection. Known *M. hyopneumoniae*-positive tissue sections as well as known *M. hyopneumoniae*-negative tissue sections were used as controls for each IHC run. Slides were scored ranging from 0 to 3 (0, no signal detectable; 1, weak labeling lining the ciliated epithelium of at least one airway; 2, weak-to-moderate labeling on the surface of a low number of airways; 3, intense labeling on the surface of several airways).

ELISA Procedure—

All serum samples were assayed for antibodies to *M. hyopneumoniae* using the IDEXX ELISA test kits and according to the manufacturer's instructions (IDEXX, *M. hyo.* Ab Test Part number: 99-06733). Known positive and negative sera were included as controls in each plate. Briefly, 100 ml of 1:40 diluted individual sample was added into the *M. hyo* antigen-coated ELISA plates. After incubation of the sample in the coated well and washing out any unbound material from the wells, goat anti-swine IgG conjugate was added to detect the bound antibodies. Test results were determined on the basis of the sample-positive (S/P) ratio: positive 5 S/P. 0.4, negative 5 S/P, 0.3, and suspect 5 S/P from 0.3 to 0.4. Although the sensitivity of the IDEXX-ELISA was considered high, the specificity of the assay was low.

Statistical Analysis—

The results for the 3-treatment groups were compared using the Scheffé's method for multiple comparisons, with $\alpha = 0.05$. Logarithmic transformation was used to normalize the percentage of the pneumonia and ELISA data.

Results—Clinical Observations:

The aptamers delivered in aerosol (APT3 group) did not cause any irritation to the pigs and did not cause coughing, sneezing or other signs of proximal or distal respiratory track irritation. Appetite did not appear to be affected, and rate of gain was similar for pigs of all 3-treatment groups during this study.

Persistent coughing began in pigs of all 3-treatment groups about 2 weeks after the challenge exposure. All pigs in the PBS and CV groups were observed coughing over the next 2 weeks. Mean number of days of persistent coughing (4.6 and 3.7 days, respectively) was similar for both groups. Only 4 of 7 pigs in the APT3 group were observed coughing during the study. Additionally, mean numbers of days with persistent coughing (1.0 day) was lower in the APT3 than in the CV group (see Table 2).

Gross lesions of pneumonia between the PBS and the CV groups were 15.3% (means) and 5.3% (means) respectively. In contrast, gross lesions of pneumonia were less severe in pigs of the APT3 group (mean 1.6% of lung affected) than in pigs of the CV group (see Table 2).

TABLE 2

Clinical results of post-challenge exposure

| Group | # pigs | Weight gain (Kg) | Persistent cough (day) | Lesion on lungs (%) | Titer (CCU/g) |
|---|---|---|---|---|---|
| PBS | 7 | 27.6 ± 3.2 | 4.6 ± 1.9 | 15.3 ± 10.3 | $10^{6.2} \pm 1.4$ |
| CV | 7 | 28.2 ± 3.1 | 2.7 ± 1.2 | 5.3 ± 4.4 | $10^{4.3} \pm 2.0$ |
| APT3 | 7 | 30.0 ± 2.8 | $1.2 \pm 1.2^a$ | $1.6 \pm 2.6^a$ | $10^{3.7} \pm 1.3$ |

$^a$Significantly different from the PBS-control group with $\alpha = 0.05$ (Scheffé's method)

Results—*Mycoplasma* Titers at Necropsy:

All pigs were positive for *M. hyopneumoniae* by the IHC tests. Titer of pulmonary mycoplasmal organisms were similar in the PBS, (mean $10^{6.2}$ CCU; range $10^{4.8}$ to $10^{7.6}$), and in the CV-group (mean $10^{4.3}$ CCU; range $10^{2.3}$ to $10^{6.3}$).

As shown in Table 2, they were systematically lower for the APT3 group (mean $10^{3.7}$ CCU; range $10^{2.4}$ to $10^{5.0}$).

Results—Antibodies (ELISA) Responses to Treatments:

The antibody levels of the mean pre-vaccination, post-vaccination, and post-challenge exposure to M. hyopneumoniae was determined for each treatment group (Table 3). The sera were assayed at a dilution of 1:5. This low dilution, several pigs in each group had detectable antibody activity against M. hyopneumoniae prior to vaccination. Serum antibody was not increased in either of the vaccinated groups 2 weeks after the last aerosol vaccination (4 weeks after the last CV vaccination). Similar results were obtained fin the study of Murphy et al.[68] (data not shown).

At necropsy (4 weeks after the challenge exposure), antibody was detected in serum of all pigs. Serum antibody activity in pigs of the CV-group (mean O.D. 1.1.89) was significantly higher than that in pigs of the PBS (0.759) and APT3 (0.663) groups. Indicating that the CV vaccination may have primed the pigs ability to immunologically respond to the MH232 challenge. However, the fact that antibody activity did not increase after vaccination, and that post-vaccination antibody activity in the vaccinated CV-group pigs was not different from the control pigs, indicates that the Suvaxyn®MH One vaccine (CV-group) was inducing a weak antibody response.

Overall Evaluation of Aerosol Vaccination—

Under the conditions of this study, the aerosol vaccination (APT3) did not induce a full protective immunity in pigs. However, aerosol vaccination with the APT3Cooc10 aptamers, perform much better than the "standard" intra-muscular vaccination with Suvaxyn®MH One (CV-group) that has been used for more than 30 years. Weight gains were higher with the APT3 vaccination while the mycoplasma titers, and the lung lesions were much lower with the APT3 vaccination than with the CV. In fact, the markedly reduced pulmonary lesions with the APT3 vaccination confirmed the efficacy of the APT3Cooc10 used in this study. The primary function of the APT3 aptamers is to bind the cilia of Mycoplasma Hyopneumoniae, not to trigger the immune system. In fact, APT3Cooc10, APT3Cooc3, and APT3Histo1 are aptamers and do not act as antigen, and have no effect on the pulmonary epithelial cells (see FIG. 8).

As pointed-out by Murphy et al.[68], possible reasons to explain the results for the aerosol APT3Cooc10 vaccine may include (i) failure of the aptamer to deposit in the lungs, (ii) rapid clearance of the aptamer from the lungs by the mucociliary apparatus, (iii) inadequate vaccination frequency, and (iv) inadequate dose of aptamers.

Location of aerosol particle deposition in the respiratory tract may be dependent on the size of the aerosol particles. Deposition of aerosol in bronchioles and alveoli is maximal when the aerosol droplets size is 0.5 to 3 μm diameter. The medical nebulizer used in this study was manufactured to produce aerosol droplets in the range of 3.1 μm, which is the upper side of the optimal range of particles to penetrate deep inside the pulmonary alveoli.

Although clearance of mycoplasmal vaccine from the respiratory tract of pigs was not measured in this study, clearance of microbial organism from the respiratory tract is known to be a remarkably rapid process[69]. The mucociliary mechanism of clearance might especially diminish the immune response to the larger particulates antigen in the upper respiratory tract. The local immune response to intra-nasally administered particulate antigen (e.g. sheep RBC) in rats is well-known to be lower than the local immune response to intra-nasally administered soluble antigen (e.g. lipopolysaccharide), suggesting that particulate antigen might be more easily entrapped in the mucus layer before contacting the underlying epithelial cells[70]. Rapid clearance of antigen from the respiratory tract might reduce the total antigenic mass exposed to the immune system, and might reduce the duration of antigenic exposure. In other words, the APT3Cooc10 aptamers were cleared from the respiratory tract before having the opportunity to meet and bind with the MH232. On the other hand, the same clearance mechanism might have helped to remove the MH232 cells that have been neutralized by the APT3Cooc10 aptamers, and this would explain the lower titers of MH232 observed in the APT3 group (compared to CV and PBS groups).

The optimal time interval for aerosol vaccine administration may be obtained using methodologies known to those skilled-in-the-art. In previous studies of a variety of vaccines in a variety of species, aerosol vaccines have been administered once[69], or were repeated at 7, 14, and to 28 days intervals[68-71]. In general, repeated vaccination at a 14-day interval resulted in an increase clearance of the virulent pathogen. But repeating the vaccination at an interval of 20 to 40 days did not results in increased bacterial clearance[68-72]. Three doses at 14-day intervals were used in our study because a similar schedule was reportedly efficacious when killed mycoplasmal bacterin was administered as an aerosol in chicken[68-72]. The frequency of vaccination may depend on the efficiency of the clearance mechanism (mucociliary apparatus). The greater the efficiency, the greater the frequency to insure continuous exposure of the APT3Cooc10 with the M.-Hyopneumoniae.

The appropriate dose for aerosol vaccination with APT3Cooc10 can be determined, for example, by determining the dose per cubic meter of air space (mole/m³-air or Kg/m³-air) within the chamber or barn-space into which the pigs are confined for 30 to 45 minutes. To assess the proper dosage of aptamers in aerosol (mole/m³-air), one may take into account the respiratory tract volume of the pigs (depends on the age), the loss associated with the mucosal clearance mechanisms (depends on the age and the gaseous environment), the loss associated with the particle size distribution (not only the Mass Median Average Diameter/MMAD) of the nebulized particles, and the loss average loss due to condensation, for example.

TABLE 3

Mean O.D. (M. Hyopneumoniae antibody) for serum from pigs vaccinated by APT3 and CV injection. Control pigs were sham-vaccinated with nebulized PBS.

| Group | # pigs | Pre-vaccination Serum IgG | Post-vaccination Serum IgG | Post-challenge Serum IgG |
| --- | --- | --- | --- | --- |
| PBS | 7 | 0.397 ± 0.287 | 0.166 ± 0.089 | 0.759 ± 0.217 |
| CV | 7 | 0.320 ± 0.259 | 0.134 ± 0.053 | 1.189$^b$ ± 0.256 |
| APT3 | 7 | 0.419 ± 0.286 | 0.313 ± 0.156 | 0.663 ± 0.353 |

$^b$Significantly different from the PBS-control group with α = 0.05 (Scheffé's method)

REFERENCES

[1] R. Desrosiers, Transmission of swine pathogens: Different means, different needs. Animal Health Res. Rev, 2011, vol. 12, pp. 1-13. Also, P. Whittleston. Porcine Mycoplasmas, pp. 133-166. In The Mycoplasmas, vol. II, 1979, pp. 133-166, Ed. by J. G. Tully and R. F. Whitcomb, Academic Press, Inc., NY. Also Etiology and epidemiology, in ENZOOTIC PNEUMONIA: THE DISEASE, produced by Hipra Inc.

[2] M. Tajima &T. Yagihashi. Interaction of *Mycoplasma Hyopneumoniae* with the Porcine Respiratory Epithelium as Observed by Electron-Microscopy. *Infection and Immunity*, 1982, vol. 37, pp. 1162-1169.

[3] C. Deblanc et al., Pre-infection of pigs with *Mycoplasma Hyopneumoniae* modifies outcomes of infection with European swine influenza virus of H1N1, but not H1N2 subtype. *Veterinary Microbiology*, 2012, vol. 157, pp. 96-105.

[4] E. L. Thacker et al., *Mycoplasma Hyopneumoniae*: Potentiation of Porcine Reproductive and Respiratory Syndrome Virus-Induced Pneumonia, *J. of Clini. Microbiol.*, 1999, vol. 37, pp. 620-627. Also, H. Nathues et al. Occurrence of *Mycoplasma Hyopneumoniae* infections in suckling and nursery pigs in region of high pig density. *Veterinary Records*, 2010, vol. 166, pp. 194-198.

[5] T. Meyuns et al., Quantification of the spread of *Mycoplasma Hyopneumoniae* in nursery pigs using transmission experiments, *Prev. Vet. Med.*, 2004, vol 66, pp. 265-275. Also see L. K. Clark, et al., Investigating the transmission of *Mycoplasma Hyopneumoniae* in a swine herd with enzootic pneumonia. Veterinary Medicine, 1991, vol. 86, pp. 543-550.

[6] K. D. C. Stark. Epidemiological investigation of the influence of environmental risk Factors on respiratory diseases in Swine—A literature review. *Veterinary J.*, 2000, vol. 159, pp. 37-56. Also F. C. Minion, Molecular pathogenesis of *mycoplasma* animal respiratory pathogens. *Frontiers in Bioscience*, 2002, vol. 7, pp. 1410-1422. Also S. Otake et al. Long-distance transport of infectious PRRSV and *Mycoplasma Hyopneumoniae* from a swine population infected with multiple viral variants. *Vet. Microbiol.*, 2010, vol. 145, pp. 198-208.

[7] P. Thongkamkoon et al. In Vitro susceptibility of *Mycoplasma Hyopneumoniae* field isolates and occurrence of Fluoroquinolone, Macrolides and Lincomycin resistance. *J. Vet. Med. Sci.*, 2013, vol. 75(8), pp. 1067-1070. Also L. L. Carrou et al., Persistence of *Mycoplasma Hyopneumoniae* in experimentally infected pigs after Marboflooxacin treatment and detection of mutation in the parC Gene, *Antimicrobial, Agents and Chemotherapy*, 2006, vol. 50, no. 6, pp. 1959-1966. Also J. et al. Resistance mechanism against fluoroquinolones in *Mycoplasma Hyopneumoniae* field isolates. *Microbial. Drug Resistance*, 2007, vol. 13, pp. 166-170.

[8] S. Beutinger et al., Local and systemic immune responses in pigs intramuscularly injected with an inactivated *Mycoplasma Hyopneumoniae* vaccine. *Vaccine*, 2013, vol. 31, pp. 1305-1311. S. Wilson et al., Vaccination of piglets at 1 week of age with an inactivated *Mycoplasma Hyopneumoniae* vaccine reduces lung lesions and improves average daily gain in body weight. *Vaccine*, 2012, vol. 30, pp. 7625-7629. P. D. Tassis et al., Clinical evaluation of intradermal vaccination against porcine enzootic pneumonia (*Mycoplasma Hyopneumoniae*), *Veterinary Records*, 2012, vol. 170, pp. 261-267. Also, M. Pieters et al. An Experimental model to evaluate *Mycoplasma Hyopneumoniae* transmission from asymptomatic carriers to unvaccinated and vaccinated sentinel pigs, *Can. J. Vet. Res*, 2012, vol. 74, pp. 157-160. Also, F. Haesebrouck, et al., Efficacy of vaccines against bacterial diseases in swine: what can we expect?, *Vet. Microbiology*, 2004, vol. 100, pp. 255-268. I. Villarreal et al., Effect of challenge of pigs previously immunised with inactivated vaccines containing homologous and heterologous *Mycoplasma Hyopneumoniae* strains. *BMC Vet. Res.*, 2012, vol. 8, 8 pages. A. Elsbernd et al. A Review on the Impact of *Mycoplasma Hyopneumoniae* Vaccination on Average Daily Gain in Swine. Iowa State University Animal Industry Report, (Leaflet R2672) 2012, 3 pages.

[9] E. L Thacker, Mycoplasmal Diseases, in Diseases of Swine, $9^{th}$ Ed., 2006, vol. 42, pp. 701-717.

[10] R. Erlinger, Glycosaminoglycans in porcine lung: An ultrastructural study using cupromeronic blue. *Cell Tissue Res.*, 1995, vol. 281, pp. 473-483.

[11] F. C. Minion et al., The genome sequence of *Mycoplasma Hyopneumoniae* strain 232 the agent of swine mycoplasmosis. *J. of Bacteriology*, 2004, vol. 186, pp. 7123-7133. Also, A. T. Vasconcelos et al. Swine and poultry pathogens: the complete genome sequences of two strains of *Mycoplasma Hyopneumoniae* and a strain of *Mycoplasma synoviae. J. of Bacteriology.* 2005, vol. 187, pp. 5568-5577.

[12] T. Hsu, S. Artiushin, & F. C. Minion, Cloning and functional analysis of P97 Swine cilium adhesin gene of *Mycoplasma Hyopneumoniae. J. of Bacteriol.*, 1997, vol. 179, pp. 1317-1323. Also F. C. Minion et al., R1 region of P97 mediates adherence of *Mycoplasma Hyopneumoniae* to swine cilia. *Infection and Immunity*, 2000, vol. 68, pp. 3056-3060. Also S. P. Djordjevic et al., Proteolytic processing of the *Mycoplasma Hyopneumoniae* cilium adhesin. *Infection and Immunity*, 2004, vol. 72, pp. 2791-2802.

[13] D. Maes et al., Control of *Mycoplasma Hyopneumoniae* infections in Pigs, *Veterinary Microbiology*, 2008, vol. 126, pp. 297-309. Also L. A. de Castro et al., Variable numbers of tandem aminoacid repeats in adhesion-related CDS products in *Mycoplasma Hyopneumoniae* strains. *Vet. Microbio.*, 2006, vol. 116, pp. 258-269. Also A. T. Deutscher et al., *Mycoplasma Hyopneumoniae* surface proteins *M. hyopneunoniae*p385 and *M. hyopneunoniae*p384 bind host cilia and glycosaminoglycans and are endopreteolytically processed by proteases that recognize different cleavage motifs. *J. of Proteome Res.*, 2012, vol. 11, pp. 1924-1936. Also J. Wilton et al., *M. hyopneunoniae*p493 (P216) is a proteolytically processed, cilium and heparin binding protein of *Mycoplasma Hyopneumoniae. Molecular Microbiology*, 2009, vol. 71, pp. 566-582. Also L. M. Seymour et al., *M. hyopneunoniae*p182 (P102) binds fibronectin and contribute to the recruitment of plasminogen to the *Mycoplasma Hyopneumoniae* cell surface. *Cellular Microbiology*, 2012, vol. 14, pp. 81-94. Also L. M. Seymour et al., *M. hyopneunoniae*p107 is a member of the multifunctional adhesin family of *Mycoplasma Hyopneumoniae. J. of Biol. Chem.*, 2011, vol. 286, pp. 10097-110104. Also L. M. Seymour et al., A processed multidomain *Mycoplasma Hyopneumoniae* adhesin binds fibronectin, plasminogen, and swine respiratory cilia. *J. of Biol. Chem.*, 2010, vol. 285, pp. 33971-33978. Also A. T. Deutscher et al., Repeat regions R1 and R2 in the P97 paralogue *M. hyopneunoniae*p271 of *Mycoplasma Hyopneumoniae* bind heparin, fibronectin and porcine cilia. *Molecular Microbiology*, 2010, vol. 78, pp. 444-458. Also D. R. Bogema et al., Characterization of cleavage events in the multifunctional cilium adhesin *M. hyopneunoniae*p684 (P146) reveals a mechanism by which *Mycoplasma Hyopneumoniae* regulates surface topography. *mBio*, 2012, vol. 3(2), pp. e00282-11. Also D. R. Bogema et al., Sequence TTKF↓LQE defines the site of proteolytic cleavage in *M. hyopneunoniae*p683 protein, a novel glycosaminoglycan and cilium adhesin of *Mycoplasma Hyopneumoniae. J. of Biol. Chem.*, 2011, vol. 286, pp. 41217-41229. Also T. A. Burnett et al., P159 is proteolytically processed, surface adhesin of *Mycoplasma Hyopneumoniae: Defined domains of P159 bind heparin and promote adherence to eukaryote cells. *Molecular Microbiology*, 2006, vol. 60, pp. 669-686.

[14] T. Hsu & F. C. Minion, Identification of the Cilium Binding Epitope of the Mycoplasma Hyopneumoniae P97 Adhesin, *Infection & Immunity*, 1998, vol. 66, pp. 4762-4766. Also Q. Zhang, T. F. Young, and R. F. Ross, Identification and Characterization *of a Mycoplasma Hyopneumoniae Adhesin. Infection and Immunity*, 1995, vol. 63, pp. 1013-1019.

[15] C. Jenkins et al., Two domains within the *Mycoplasma Hyopneumoniae* cilium adhesin bind heparin. *Infection and Immunity*, 2006, vol. 74, pp. 481-487.

[16] Plasminogen and fibronectin are highly abundant multifunctional glycoproteins that circulate in body fluids. They are deposited on cell surfaces and are extra-cellular matrix components. Fibronectin is also important in wound repair of respiratory epithelial cells and plasminogen is present in airway of healthy pigs. See L. M. Seymour et al., *M. hyopneunoniae*p182 (P102) binds fibronectin and contribute to the recruitment of plasminogen to the *Mycoplasma hyoponeumoniae* cell surface. *Cellular Microbiology*, 2012, vol. 14, pp. 81-94. Also see M. Swaisgood et al., Plasminogen is an important regulator in the pathogenesis of a murine model of asthma. *Am. J. of Respir. Crit. Care Med.* 2007, vol. 176, pp. 333-342. Also see C. Coraux et al., Epithelial extracellular matrix interactions and stem cells in airway epithelial regeneration. *Proc. Am. Thoracic Soc.*, 2008, vol. 5, pp. 689-694).

[17] GenBank accession number U50901. Protein id="AAB47806.1"

[18] S. B. Marchioro, S. Simionatto, et al., Production and characterization of recombinant transmembrane proteins from *Mycoplasma Hyopneumoniae. Veterinary Microbiology*, 2012, vol. 155, pp. 44-52.

[19] Also A. T. Deutscher et al., Repeat regions R1 and R2 in the P97 paralogue *M. hyopneunoniae*p271 of *Mycoplasma Hyopneumoniae* bind heparin, fibronectin and porcine cilia. *Molecular Microbiology*, 2010, vol. 78, pp. 444-458.

[20] Q. Zhang, T. F. Young, and R. F. Ross, Microtiter Plate Adherence Assay and receptor analogs for *Mycoplasma Hyopneumoniae. Infection & Immunity*, 1994, vol, 62, pp. 1616-1622.

[21] I. Dobrescu et al., In vitro and ex-vivo analyses of co-infections with swine PRRS and porcine reproductive and respiratory syndrome viruses. *Vet. Microbiol.*, 2014, vol. 169, pp. 18-32.

[22] M. Sibila et al. Current perspectives on the diagnosis and epidemiology of *Mycoplasma Hyopneumoniae* infection. *Vet. J.*, 2009, vol. 181, pp. 221-231. Also E. L. Thacker, Diagnosis of *Mycoplasma Hyopneumoniae. J of Swine Health & Prod.*, 2004, vol. 12, pp. 252-254. Also R. Desrosiers, A review of some aspects of the epidemiology, diagnosis, and control of *Mycoplasma Hyopneumoniae* infections. J of Swine Health and Prod. 2001, vol. 9, pp. 233-237.

[23] V. Sorensen et al., *Mycoplasma Hyopneumoniae* infection in pigs: Duration of the disease and evaluation of four diagnostic assays, *Vet. Microbiol.*, 1997, vol. 54, pp. 23-33

[24] L. Moorkamp et al. Detection of respiratory pathogens in porcine lung tissue and lavage fluid. *Vet. J.*, 2008, vol. 175, pp. 273-275.

[25] K. T. Kurth et al. Use of a *Mycoplasma Hyopneumoniae* nested polymerase chain reaction test to determine the optimal sampling sites in swine. J. of Veterinary Diagnostic Invest. 2002, vol. 14, pp. 463-469.

[26] M. Pieters & C. Pijoan, Detection of *Mycoplasma Hyopneumoniae* DNA in experimentally infected pigs. In the *Proc. of the 19$^{th}$ Int. Pig Veterinary Society* (IPVS), Copenhagen, 2006, p. 209.

[27] SciFinder, P. Dua, S. Kim, & DK Lee, Patents on SELEX and therapeutic aptamers, in *Recent Pat. DNA Gene Seq.* 2008, vol. 2, pp. 172-186. Also S. Missailids & A. Hardy. Aptamers as inhibitors of target proteins, in *Expert Opinion on Therapeutics Patents*, 2009, vol. 19, pp. 1073-1082.

[28] D. S. Wilson & J. W. Szostak. In vitro selection of functional nucleic acids. *Annual Rev. Biochem.*, 1999, vol. 68, pp. 611-647. Also A. Cibiel et al. Methods to identify aptamers against cell surface biomarkers. *Pharmaceuticals*, 2011, vol. 4, pp. 1216-1235. Also B. Hall et al. Design, synthesis, and amplification of DNA pools for in vitro selection. *Current Protocols in Molecular Biology*, 2009, vol. 88, pp. 24.2.1-24.2.27. Also S. Chandra & B. Gopinath. Methods developed for SELEX. *Anal. Bioanal. Chem.*, 2007, vol. 387, pp. 171-182.

[29] G. Mayer. The chemical biology of aptamers: A Review. *Angew. Chem. Int. Ed.*, 2009, vol. 48, pp. 2672-2689.

[30] S. Balamuragan et al. Surface immobilisation methods for aptamer diagnostic applications. *Anal. Bioanal. Chem.*, 2008, vol. 390, pp. 1009-1021. Also X. Fang & W. Tan. Aptamers generated from Cell-SELEX for molecular medicine: A chemical biology approach, in *Accounts of Chem. Res.*, 2010, vol. 43, pp. 48-57. Also J. Liu et al. Recent developments in protein and cell-targeted aptamer selection and applications, in *Curr. Medi. Chem.*, 2011, vol. 18, pp. 4117-4125.

[31] Y. Zhang et al. Tumor-targeted drug delivery with aptamers. *Curr. Med. Chem.*, 2011, vol. 18, pp. 4185-4194. Also A. D. Keefe et al, Aptamers as therapeutics, *Nature Reviews: Drug discoveries*, 2010, vol. 9 pp. 537-550. Also Z. Zhang et al. Nucleic acid aptamers in human viral disease. *Arch. of Immunol. Ther. Exp.*, 2004, vol. 52, pp. 307-315.

[32] W. Zhao et al. Cell-surface sensors for real-time probing of cellular environments, in *Nature Nanotechnology*, 2011, vol. 6, pp. 524-531. Also K. Sefah et al. Nucleic acid aptamers for biosensors and bio-analytical applications, *Analyst*, 2009, vol. 134, pp. 1765-1775. Also E. Torres-Chavolla & E. C. Alocilja. Aptasensors for detection of microbial and viral pathogens. *Biosensors & Bioelect*, 2009, vol. 24, pp. 3175-3182. Also M. N. Velasco-Garcia & S. Missailidis. New trends in aptamer-based electrochemical biosensors. *Gene Therapy & Mole. Biol.*, 2009, vol. 13, pp. 1-9. Also Y. Xiao et al. Preparation of electrode-immobilized, redox-modified oligonucleotides for electrochemical DNA and aptamer-based sensing. *Nature Protocols*, 2007, vol. 2, pp. 2875-2880. I. Willner and M. Zayats. Electronic Aptamer-Based Sensors. *Angew. Chem., Int. Ed.*, 2007, vol. 46, pp. 6408-6418. Also S. Song et al. Aptamer-based biosensors. *Trends in Anal. Chem.*, 2008, vol. 27, pp. 108-117.

[33] D. G. Burch, Controlling Mycoplasmal (Enzootic) Pneumonia, in in Farmers Guide, UK, February 2004. Also D. Maes, *Mycoplasma Hyopneumoniae* infections in pigs: Update on epidemiology and control, in *Proc. of the 21$^{st}$ IPVS Congress*, Vancouver, 2010, pp. 30-35.

[34] Mypravac Suis® (Hipra, Spain), Porcilis® (Merk Animal Health), MycoFlex® (Boerhringer Ingelheim), Suvaxyn *M. HYOPNEUNONIAE*-One® (Zoetis), etc

[35] D. G. Burch, *Mycoplasma* vaccines-Comparative studies, in Pig World Magazine, UK, 2001

[36] D. Maes et al. Effect of vaccination against *Mycoplasma hyopneumoniae* in pig herds with an all-in/all-out production system. *Vaccine,* 1999, vol. 17, pp. 1024-1034.

[37] J. Vicca et al., In Vitro Susceptibilities of *Mycoplasma Hyopneumoniae* Field Isolates, *Antimicrobial Agents & Chemotherapy,* 2004, vol. 48, pp. 4470-4472. Also Inamoto et al., 1994

[38] T. Meyns et al., Comparison of transmission of *Mycoplasma Hyopneumoniae* in vaccinated and non-vaccinated populations, *Vaccine,* 2006, vol. 24, pp. 7981-7086.

[39] M. Sibila et al., Chronological study of *Mycoplasma Hyopneumoniae* infection, sero-conversion and associated lung lesions in vaccinated and non-vaccinated pigs, *Vet. Microbiol.,* 2007, vol. 122, pp. 197-201.

[40] I. Villarreal et al., The effect of vaccination on the transmission of *Mycoplasma Hyopneumoniae* in pigs under field conditions, *Veterinary Journal,* 2011, vol. 188, pp. 48-52.

[41] E. Roulet et al., High-throughput SELEX-SAGE method for quantitative modeling of transcription-factor. *Nature Biotechnology,* 2002, vol. 20, pp. 831-835. Also A. B. Iliuk et al., Aptamers in bioanalytical applications. *Anal. Chem.,* 2011, vol. 83, pp. 4440-4452.

[42] T. F. Young et al. A tissue culture system to study respiratory ciliary epithelial adherence of selected swine mycoplasmas. *Vet. Microbiol,* 2000, vol. 71, pp. 269-279.

[43] G. C. Zielinski & R. F. Ross, Adherence of *Mycoplasma Hyopneumoniae* to porcine ciliated respiratory tract cells. *Am. J. of Vet. Res.,* 1993, vol. 54, pp. 1262-1269.

[44] M. DeBey & R. F. Ross, Ciliostasis and loss of cilia induced by *Mycoplasma Hyopneumoniae* in porcine tracheal organ cultures. *Infection & Immunity,* 1994, vol. 62, pp. 5312-5318.

[45] D. Calus et al. In vivo virulence of *Mycoplasma Hyopneumoniae* isolates does not correlate with in vitro adhesion assessed by a microtitre plate adherence assay. *J. of Appl. Microbiol.,* 2009, vol. 106, pp. 1951-1956.

[46] M. Yamaya et al., Differentiated structure and function of cultures from human tracheal epithelium. *Am. J. of Physiology: Lung & Cell. Mol. Physiol.,* 1992, vol. 262, no. 6, pp. L713-L724

[47] A. B. Clarke et al., Regulation of ciliated cell differentiation in cultures of rat tracheal epithelial cells. *Am. J. of Resp. Cell & Mole. Biol.,* 1995, vol. 12, pp. 329-338.

[48] A. D. Keefe & S. T. Cload, SELEX with modified nucleotides. *Curr. Opinion in Chem. Biol.,* 2008, vol. 12, pp. 448-456. Also J. Wang & G. Li. Aptamers against cell surface receptors: Selection, modifications and application. *Curr. Medi. Chem.,* 2011, vol. 18, pp. 4107-4116. R. E. Wang et al. Improving the stability of aptamers by chemical modifications. *Curr. Medi. Chem.,* 2011, vol. 18, pp. 4126-4138.

[49] *The Concise Encyclopedia of Polymer Science And Engineering,* pp. 858-859, J. I. Kroschwitz, ed. By John Wiley & Sons, 1990. Also U. Englisch & D. H. Gausset, Chemically Modified Oligonucleotides as Probes and Inhibitors. *Angewandte Chemie, Int. Edition,* 1991, vol. 30, pp. 613-722. Also Y. S. Sanghvi, Chapter 15, *Antisense Research and Applications,* pp. 273-288, ed. by S. T. Crooke and B. Lebleu, published by CRC Press, Boca Raton, 1993.

[50] Y. S. Sanghvi, Chapter 15, *Antisense Research and Applications,* see pp. 276-278. Ed. by S. T. Crooke and B. Lebleu, published by CRC Press, Boca Raton, 1993.

[51] See U.S. Pat. No. 6,303,374 (Antisense modulation of caspase 3 expression).

[52] F. Szoka & D. Papahadjopoulos. Comparative properties and methods of preparation of lipid vesicles (liposomes). *Annual review of biophysics and bioengineering,* 1980, vol. 9, pp. 467-508. Also A. Gomezhens & J. Fernandezromero. Analytical methods for the control of liposomal delivery systems. *TrAC Trends in Analytical Chemistry,* 2006, vol. 25, pp. 167-178. Also M. R. Mozafari. Liposomes: an overview of manufacturing techniques. *Cell Mol Biol Lett.,* 2005, vol. 10, pp. 711-719.

[53] A. Jesorka & O. Orwar, Liposomes: Technologies and Analytical Applications. in *Annual Rev. Anal. Chem.,* 2008, vol. 1, pp. 801-832. Also B. Maherani et al. Liposomes: A Review of Manufacturing Techniques and Targeting Strategies, in *Current Nanoscience,* 2011, vol. 7, pp. 436-452.

[54] see Remington's Pharmaceutical Sciences, Mack Publishing Co., Easton, Pa., latest edition. Also Advanced Drug Delivery: Perspectives and prospects. In *Advanced Drug Delivery Reviews,* 2013, vol. 65, no 1, pp. 1-148. Also see *Drug Delivery Journal.* Copyright by Informa Healthcare USA, Inc. ISSN 1071-7544 print/ISSN 1521-0464 online. Also J. S. Patil & S. Sarasija. Pulmonary drug delivery strategies: A concise, systematic review. *Lung India,* 2012, vol. 29, pp. 44-49.

[55] W. Rojanarat et al. Inhaled pyrazinamide proliposome for targeting alveolar macrophages. *Drug Delivery,* 2012, vol. 19, pp. 334-345.

[56] S. Parasuraman, Toxicolological screening. *J. of Pharmaco & Pharmacotherapeutics,* 2011, vol 2(2), pp. 74-79.

[57] A. Noonberg et al., *Nucleic Acids Res,* 1994, vol. 22, pp. 2830-2836. L. Thompson et al., *Nucleic Acids Res,* 1995, vol. 23, pp. 2259-2268.

[58] A. Kunkel & Pederson, *Nucleic Acids Res,* 1989, vol. 17, pp. 7371-7379. Also Kunkel et al., *Proc. Natl. Acad. Sci. USA,* 1986, vol. 83, pp. 8575-8579. Also Reddy et al., *J. Biol. Chem.,* 1987, vol. 262, pp. 75-81.

[59] Hall et al., *Cell,* 1982, vol. 29, pp. 3-5. Also Nielsen et al., *Nucleic Acids Res.,* 1993, vol. 21, pp. 3631-3636. Fowlkes & Shenk, *Cell,* 1980, vol. 22, pp. 405-413. Also Gupta & Reddy, *Nucleic Acids Res.,* 1991, vol. 19, pp. 2073-2075. Kickhoefer et al., *J. Biol. Chem.,* 1993, vol. 268, pp. 7868-7873. Romero & Blackburn, *Cell,* 1991, vol. 67, pp. 343-353.

[60] L. M. Khachigian. DNAzymes: cutting a path to a new class of therapeutics. *Curr. Opin. Mol. Ther.,* 2002, vol. 4, pp. 119-121.

[61] https://en.wikipedia.org/wiki/Fluorescent_tag#Methods_for_tracking_biomolecules

[62] *PCR Protocols: A Guide to Methods and Applications.* Editors M. A. Innis, D. H. Gelfand, J. J. Sninsky, & T. J. White. Academic Press, 1990.

[63] see Rational Drug Design: Novel Methodology and Practical Application, Editors A. L. Parrill & M. R. Reddy, Oxford University Press, 1999. Also *Advances In Antiviral Drug Design,* Editor De Clerq. Elsevier Science & Tech, 2007. Also *Textbook of Drug Design and Discovery.* Editors U. Madsen, P. Krogsgaard-Larsen & T. Liljefors. Taylor & Francis, 2002. ISBN 0-415-28288.

[64] V. Lounnas et al. Current progress in Structure-Based Rational Drug Design marks a new mindset in drug discovery, *Compu. & Struc. Biotech. J.,* 2013, vol. 5, e201302011. Also 65 http://en.wikipedia.org/wiki/Rational_drug_design
66 Aptamers specific for biomolecules and methods of making (U.S. Pat. No. 5,756,291). Also *Affinity Chromatography*, Editor H. Schott, Marcel Dekker, Inc., New York, 1984.
67 *Current Protocols in Molecular Biology*, ed. by F. M. Ausubel et al., John Wiley & Sons, 1999-2014 (DOI: 10.1002/0471142727).
68 D. A. Murphy et al., Aerosol vaccination of pigs against *Mycoplasma Hyopneumoniae* infection. Am. J. Vet. Res., 1993, vol. 54(11), pp 1874-1880.
69 A. T. M. Bosch et al., Viral and Bacterial Interactions in the Upper Respiratory Tract. PLoS Pathog, 2013, vol. 9(1), paper e1003057. Also R. J. Boyton and P. J. Openshaw, Pulmonary Defenses to acute respiratory infections. Brit. Med. Bull., 2002, vol. 61(1), pp. 1-12. Also G. A. Laurenzi et al., Clearance of bacteria in the lower respiratory, Science, 1963, vol. 142, pp. 1572-1573.
70 D. M. H. Hameleers et al., Mucosal and systemic antibody formation in the rat after intranasal administration of three different antigens. Immuno. Cell. Biol., 1991, vol. vol. 69, pp. 119-125.
71 S. Morgan et al., Aerosol Delivery of a Candidate Universal Influenza Vaccine Reduces Viral Load in Pigs Challenged with Pandemic H1N1 Virus. J. of Immunology, 2016 (May), doi:10.4049/jimmunol.1502632
72 E. Hayatsu et al., Local immunization in chicken respiratory tract with killed *Mycoplasma* Gallisepticum vaccine. *Japan J. of Vet. Sci.*, 1974, vol. 36, pp. 311-319.

The invention claimed is:

1. A nucleic acid molecule comprising at least one polynucleotide sequence aptamer capable of specifically binding to binding motifs on cleaved segments of surface proteins on *M. hyopneumoniae*, wherein the at least one polynucleotide sequence is selected from the group consisting of APT3Cooc10 (SEQ ID NO: 1), APT3Cooc4 (SEQ ID NO: 2), APT3Cooc2 (SEQ ID NO: 3), APT3Histo1 (SEQ ID NO: 4), APT3Cooc3 (SEQ ID NO: 5), APT3Histo2 (SEQ ID NO: 6), APT3Histo4 (SEQ ID NO: 7), APT3Histo5 (SEQ ID NO: 8), APT3Histo9 (SEQ ID NO: 9), APT3Cooc7 (SEQ ID NO: 10), and combinations thereof.

2. The nucleic acid molecule of claim 1, wherein the polynucleotide sequences are capable of:
   a) binding to a surface protein of *M. hyopneumoniae* carrying a motif |AAKPE| AAKPV|AAKPE| TTKPV| (SEQ ID NO. 19) or a motif that has at least an 80%, 85%, 90%, or 95% identity with said motif; or
   b) binding to P97, P102, P116, P146, P216, or P159 surface proteins of *M. hyopneumoniae* or a fragment having at least 80%, 85%, 90%, or 95% sequence identity with the P97, P102, P116, P146, P216, and P159 surface proteins, that control binding of *M. hyopneumoniae* onto the cilia.

3. The nucleic acid molecule of claim 1, wherein the surface proteins are the P97 and/or P102 proteins that control initial adherence of *M. hyopneumoniae* on to cilia.

4. The nucleic acid molecule of claim 1, wherein the polynucleotide sequences include FDG ([$^{18}$F]-2-fluoro-2-deoxy-D-glucose) and/or polyalkylene glycol and polyethylene glycol (PEG) modified nucleotides.

5. A pharmaceutical composition comprising the nucleic acid molecule of claim 1 and a physiologically acceptable carrier.

6. A composition comprising the nucleic acid molecule of claim 1 and an additional agent.

7. The composition of claim 6, wherein the additional agent is an immunomodulatory agent, an anti-microbial agent, an antisense molecule, or a ribozyme, and wherein the anti-microbial agent is conjugated to the nucleic acid molecule.

8. The nucleic acid molecule according to claim 1 for treating *M. hyopneumoniae* infection in a subject in need thereof, and wherein the subject is a pig.

9. An antiviral agent comprising the nucleic acid molecule according to claim 1 for treating *M. hyopneumoniae* infection in a subject in need thereof, and wherein the subject is a pig.

* * * * *